(12) United States Patent
Morgan et al.

(10) Patent No.: US 7,115,407 B2
(45) Date of Patent: Oct. 3, 2006

(54) RECOMBINANT TYPE II RESTRICTION ENDONUCLEASES, MMEI AND RELATED ENDONUCLEASES AND METHODS FOR PRODUCING THE SAME

(75) Inventors: Richard D. Morgan, Middletown, MA (US); Tanya Bhatia, Peabody, MA (US); Theodore Davis, Boxford, MA (US); Lindsay Lovasco, Salem, MA (US)

(73) Assignee: New England BioLabs, Inc., Ipswich, MA (US)

( * ) Notice: Subject to any disclaimer, the term of this patent is extended or adjusted under 35 U.S.C. 154(b) by 325 days.

(21) Appl. No.: 10/616,624

(22) Filed: Jul. 10, 2003

(65) Prior Publication Data

US 2004/0091911 A1    May 13, 2004

(51) Int. Cl.
*C12N 9/22* (2006.01)
*C12N 15/55* (2006.01)

(52) U.S. Cl. ............... 435/199; 435/320.1; 435/252.3; 536/23.2

(58) Field of Classification Search ............ None
See application file for complete search history.

(56) References Cited

U.S. PATENT DOCUMENTS

| 5,200,333 A | 4/1993 | Wilson ............ 435/172.3 |
| 6,383,770 B1 | 5/2002 | Roberts et al. ........... 435/19 |

FOREIGN PATENT DOCUMENTS

| EP | 0066994 A2 | 12/1982 |
| EP | 1199365 A2 | 4/2002 |

OTHER PUBLICATIONS

Endow, et al., J. Mol. Biol. 112:521 (1977).
Waalwijk, et al. Nucleic Acids Res. 5:3231 (1978).
Gingeras and Brooks, Proc. Natl. Acad. Sci. USA 80:402 (1983).
Altschul, et al., Nucleic Acids Res. 25:3389-3402 (1997).
Tocholski, Gene 223:293-302 (1998).
Aravind, et al., Nucleic Acids Res. 28:3417-3432 (2000).
Matsudaira, et al. J. Biol. Chem. 262-10035-10038 (1987).
Looney, et al., Gene 80:193-208 (1989).
Waite-Rees, et al., J. Bacteriol. 173:5207-5219 (1991).
Lin, et al. Proc. Natl. Acad. Sci. USA 98:2740-2745 (2001).
Boyd, Nucleic Acids Res. 14:5255 (1986).
Schildkraut, In Genet. Eng. 6:117-140 (1984).
Skoglund, Gene 88:1-5 (1990).
Devereux, et al. Nucleic Acids Res. 12:387-395 (1984).
Altschul, et al. J. Mol. Biol. 215:403-410 (1990).
Gish, et al., Nature Genet. 3:266-722 (1993).
Tucholski, et al., Gene 223:293-302 (1998).
Jeltsch, et al., Gene 157:157-162 (1995).
Boyd, et al., Nucleic Acids Res. 14:5255-5275 (1986).
European Patent Office, International Search Report dated Jan. 14, 2004 re PCT/US03/21570.

*Primary Examiner*—Charles L. Patterson, Jr.
(74) *Attorney, Agent, or Firm*—Harriet M. Strimpel

(57) ABSTRACT

In accordance with the present invention, there is provided a DNA (deoxyribonucleic acid) fragment which encodes the MmeI type II restriction endonuclease enzyme. This one polypeptide possesses two related enzymatic functions; namely an endonuclease activity which recognizes the DNA sequence 5'-TCC(Pu)AC-3' and cleaves as indicated by the arrows:

```
5'-TCCRAC(N20)↓-3'

3'-AGGYTG(N18)↑-5'
``` and a second enzymatic activity that recognizes the same DNA sequence, 5'-TCC(Pu)AC-3', but modifies this sequence by the addition of a methyl group to prevent cleavage by the MmeI endonuclease activity.

6 Claims, 16 Drawing Sheets

MmeI DNA CLEAVAGE

FIG. 2A

```
   1  GAATTCCAGA TAGGTAGTCC TTTGGTACTT CCATCCCAAC CAGTGTCACG
  51  TTCCGCGCCA AACCAATCGG TTAAAGTGTA AGAAAGTCTT GCACTGAAGT
 101  AGCTGTAGGA CAAACCGAAG TTAACCTCTG TGGTATCCCA GCGACCACCT
 151  TTAGGTGTTT GACGGAAGCC TGCTGCGTCA CCTGCCAAGT TATATTTCTT
 201  CCATGAACCA CCTGGGTACA GGTAGCTGAT CAAACCAGCA GTCCAACCCA
 251  AGCCTTCAAT AGCAGGAATA GTTCCGTTAT ACCCACCATA AATATCAATT
 301  TCGGCAGTTG CATCAGGGAA GGTATTTGGT GTCACGTTTG AACCCCATGC
 351  ACCGACATAA AAGCCGCTGT CATGAGTAAT ATCAATACCG CCTTGAACGG
 401  CAGGTTTGTG CCAGTTTTGT GAAATACCAC GAGCATAGTA ATCTGAAACA
 451  AATCCAACGT TTGCAGTAGC AGCCCAGGCT GATTTTTCTT CTTTAGCCTC
 501  TTCAGCTGCG TATGAAACTT GGGCAAAAGA TAATGTGCTT AACACTGCTG
 551  TGAGCAATAT AGATTGACGC ATTATGAGTC CTCTCTCTGT GAAATCTTTG
 601  ATTAAGTTGT TGTAAACGAG AATGAAACAA CAACCACAAA GCAAAGCACG
 651  TGCCAAACTA TAAATAACAT TATAATCAAT TATTTAAAAT ATATTTATAA
 701  TCTAAAATAT TAAATTAATT ATTTAATAAA CTGTTTTTTA TTGATTTAAC
 751  TCTAAAACAT ATGGGTGCAA CCACCCTTTT TACTCACTGA TAATGCTAAN
 801  ATAGCCAACA AAGGAGCCTT CACCATGCTG ATTTCAAATG AAAAAATTCA
 851  GGAATTATCT TTAAAAATCA AACAACTAAT CGAATCAAGC CCCATTTCAG
 901  AGCTAAATAA CAACTTGCAT GCACTAATTC AGGGCGCACT CACCAAAATG
 951  GAACTTGTTT CGCGTGAAGA ATTCGATATC CAATCTGCAT TATTAGCGCG
1001  CACGCAAGAG CAATTAAAAC GTCTTGAAGA AAAAATCAGC CAGCTTGAAG
1051  AAGGGCAGGC ATCCAGAAAG TAAAAATTAA TTTACAATTG TTAGCATTCC
1101  ATTATTGAGG AGTGCGCTAT GAGTCTGGCG GTGTTATACA GTCGCGCGTT
1151  AAGCGGCATG GAGGCGCCAG AAGTGGTGGT AGAAGTCCAC TTGGCGAATG
1201  GACTACCCAG CTTTACCATT GTTGAAACAT ATTGAAACTT TAAGCCTTAG
1251  CATTTTTTCA AATATACAAA TGCCCCAAGC TGGTGCATTA AGAAGAATGT
```

FIG. 2B

```
1301  AACAACTCCC TGCAGACTAG GAATAACTTC ATGATTTAAC GAACATCCCT
1351  GAGTTTCAAA GTCGAATCTT CTCGTGTTGC AAATTTCTAC AGCTTCCTTT
1401  CTGACCCTCT TGCACCAAAT TGCACTATGG CGCTAATAAA TCTTCTGCTA
1451  TCCAATAATG TCCAACTAAC CCTTTATGGA CTCTTAAAAA AGATTTAATA
1501  AATGATTAAG ATGAATTCAA GGAATTTGAT GCCTGGAAAT ATGGCAAAAG
1551  CAAAAAGGCA GCCCAGTGCT GACTTTTTTG TTTTAACATT GGCCCATATA
1601  TCCAATTTCA AATAATTTAA AAATTATCGG GAGCTAATCT GTGGCTTTAA
1651  GCTGGAACGA GATAAGAAGA AAAGCTATTG AGTTTCTAA AGATGGGAA
1701  GACGCCTCAG ATGAAAACAG TCAAGCCAAA CCCTTTTTAA TAGATTTTTT
1751  CGAAGTTTTT GGAATAACTA ATAAGAGAGT TGCAACATTT GAGCATGCTG
1801  TGAAAAAGTT CGCCAAGGCC CATAAGGAAC AATCTCGAGG ATTCGTAGAT
1851  TTGTTTTGGC CTGGCATTCT TCTTATTGAA ATGAAAAGCA GAGGTAAAGA
1901  CCTCGACAAA GCGTATGACC AGGCACTTGA TTACTTTTCT GGCATTGCAG
1951  AAAGAGACTT ACCCAGATAC GTTTTAGTTT GCGACTTCCA GCGTTTCAGA
2001  TTAACAGACC TAATAACAAA AGAGTCAGTT GAATTTCTTT TAAAGGACTT
2051  ATACCAAAAT GTGAGGTCTT TTGGTTTTAT AGCTGGTTAT CAAACTCAAG
2101  TAATCAAGCC ACAAGACCCT ATTAATATTA AGGCGGCTGA ACGGATGGGT
2151  AAGCTTCATG ACACCCTGAA GTTGGTTGGA TATGAGGGAC ACGCTTTAGA
2201  ACTTTATCTA GTGCGTTTAC TTTTTTGCTT ATTCGCAGAA GACACAACTA
2251  TTTTTGAGAA AAGTTTATTC CAAGAATATA TCGAGACAAA GACGCTAGAG
2301  GACGGCAGTG ACCTTGCACA TCATATCAAT ACACTTTTTT ATGTTCTCAA
2351  TACCCCAGAA CAAAAAAGAT TAAAGAATCT AGACGAACAC CTTGCTGCAT
2401  TTCCATATAT CAATGGAAAA CTTTTCGAGG AGCCACTTCC GCCAGCTCAG
2451  TTTGATAAAG CAATGAGAGA GGCATTGCTT GACTTGTGCT CATTAGATTG
2501  GAGCAGGATT TCACCAGCAA TATTTGGAAG TTTATTCCAA AGCATTATGG
2551  ATGCTAAAAA GAGAAGAAAT CTTGGGGCAC ACTACACCAG CGAAGCAAAT
2601  ATTCTCAAGT TAATCAAGCC ATTGTTTCTT GACGAGCTCT GGGTAGAGTT
2651  CGAGAAAGTT AAAAATAATA AAAATAAATT ACTAGCGTTC CACAAAAAAC
2701  TAAGAGGACT TACATTTTTC GACCCTGCAT GCGGTTGCGG AAATTTTCTT
```

FIG. 2C

```
2751 GTAATCACAT ACCGAGAACT AAGACTTTTA GAAATTGAAG TGTTAAGAGG
2801 ATTGCATAGA GGTGGTCAAC AAGTTTTGGA TATTGAGCAT CTTATTCAGA
2851 TTAACGTAGA CCAGTTTTTT GGTATCGAAA TAGAGGAGTT TCCCGCACAG
2901 ATTGCTCAGG TTGCTCTCTG GCTTACAGAC CACCAAATGA ATATGAAAAT
2951 TTCAGATGAG TTTGGAAACT ACTTTGCCCG TATCCCACTA AAATCTACTC
3001 CTCACATTTT GAATGCTAAT GCTTTACAGA TTGATTGGAA CGATGTTTTA
3051 GAGGCTAAAA AATGTTGCTT CATATTAGGA AATCCTCCAT TTGTTGGTAA
3101 AAGTAAACAA ACACCGGGAC AAAAAGCGGA TTTACTATCT GTTTTTGGAA
3151 ATCTTAAATC CGCTTCAGAC TTAGACCTAG TTGCTGCTTG GTATCCCAAA
3201 GCAGCACATT ACATTCAAAC AAATGCAAAC ATACGCTGTG CATTTGTCTC
3251 AACGAATAGT ATTACTCAAG GTGAGCAAGT ATCGTTGCTT TGGCCGCTTC
3301 TGCTCTCATT AGGCATAAAA ATAAACTTTG CTCACAGAAC TTTCAGCTGG
3351 ACAAATGAGG CGTCAGGAGT AGCGGCGGTT CACTGCGTAA TTATCGGATT
3401 TGGGTTGAAG GATTCAGATG AAAAAATAAT CTATGAGTAT GAAAGTATTA
3451 ATGGAGAACC ATTAGCTATT AAGGCAAAAA ATATTAATCC ATATTTGAGA
3501 GACGGGGTGG ATGTGATTGC CTGCAAGCGT CAGCAGCCAA TCTCAAAATT
3551 ACCAAGCATG CGTTATGGCA ACAAACCAAC AGATGATGGA AATTTCCTAT
3601 TTACTGACGA AGAAAAAAAC CAATTTATTA CAAATGAGCC ATCTTCCGAA
3651 AAATACTTCA GACGGTTTGT GGGCGGGGAT GAGTTCATAA ACAATACAAG
3701 TCGATGGTGT TTATGGCTTG ACGGTGCTGA CATTTCAGAA ATACGAGCGA
3751 TGCCTTTGGT CTTGGCTAGG ATAAAAAAAG TCCAAGAATT CAGATTAAAA
3801 AGCTCGGCCA AACCAACTCG ACAAAGTGCT TCGACACCAA TGAAGTTCTT
3851 TTATATATCT CAGCCGGATA CGGACTATCT GTTGATACCT GAAACATCAT
3901 CTGAAAACAG ACAATTTATT CCAATTGGTT TTGTTGATAG AAATGTCATT
3951 TCAAGTAACG CAACGTATCA TATTCCTAGT GCTGAACCTT TGATATTTGG
4001 CCTGCTTTCA TCGACCATGC ACAACTGCTG GATGAGAAAT GTAGGAGGAA
4051 GGTTAGAAAG TCGTTATAGA TATTCTGCCA GCCTGGTTTA CAACACGTTT
4101 CCATGGATTC AACCCAACGA AAAACAATCG AAAGCGATAG AAGAAGCTGC
```

FIG. 2D

```
4151 ATTTGCGATT TTAAAAGCTA GAAGCAATTA TCCAAACGAA AGTTTAGCTG
4201 GTTTATACGA CCCAAAAACA ATGCCTAGTG AGCTTCTTAA AGCACATCAA
4251 AAACTTGATA AGGCTGTGGA TTCTGTCTAT GGATTTAAAG GACCAAACAC
4301 AGAAATTGCT CGAATAGCTT TTTTGTTTGA AACATACCAA AAGATGACTT
4351 CACTCTTACC ACCAGAAAAA GAAATTAAGA AATCTAAGGG CAAAAATTAA
4401 TTAATGTATT TAACATTAAA CCACCCTGAT TTATTTCGAA TAGTTCAAAT
4451 GCTTCCATGT GGACTAATCG CCTTCAATCA TATTAAAAAA CCGACGCTAG
4501 TAATAAAAAC TTCCAAAGAG GCCATATTAA CCGCCAAAAT TAATCGTGAA
4551 TTTAAAATAT ATCTTTATCA AACCACATCG GCTTGTGTTC TAGTAAGTGC
4601 ATTTTTTGAC GATTCTGATA GTCCACTATT CATTACAACA CCAATTGTTC
4651 GAGATGACCA ACACTCCTTA GACTTGTTAA GATTTTTAAT CAACAATGAT
4701 TTTACGATTT GCTTCTTTGA TGAACTGAAC CGAGAATTTC TTTCCGTTAA
4751 CGCAACTGGT AATTTAGTCT CTATCTTTGA GAGCATTCAC TTGATGCCAC
4801 TGCCGAGCCC AGAGGAAGCC CACAATGCAT TGAATGAAGC GGAATTTTGG
4851 TTCAGTTTAC GCTCAGCTGC TGATGATGAA TCATCTATCC AGGTTTCTTT
4901 ATTGGATAAT CTATTTCCTG ACGATTTTGT AATTTATGAC CTATCCTCAA
4951 ACAAAAACGA TATGACATCA TTGGTTAGAG AAACTAAACC AGGATACTAT
5001 CAGGAAGCAG ATATTGCAAA GTTACTAACA AGAGCTTTTA GTTTGGAAAG
5051 CATTTATCAG AATCCAGTGA AAACAAGCGA TTCAAAAGAG TTGGCAGACG
5101 TTGTGGTATT CGGCCAAAAG GAAATTTTAA TAATTCAAGC TAAAGATAGT
5151 GAAAACAATC AGAAACAAGT TTTAGAGGTT TCGTTAGACA AGAAATGCGC
5201 AAAGTCTTCA AAGAAACTTT CTGAAGCTTT GGCACAACTC ACCGACACTA
5251 TCTTAACAAT ATCCAATACA CCAATAGTTG ATGTTCGGGT TGGTAAGAAA
5301 AAATGCACTC TGAACTTTGA GGGAAAGCAG CTTATTGGTA TCGTCGTTGT
5351 TAAAGAGCTT TTTAATGATA TTTACGATAA ATACAGTCAA AAAGTTTTTG
5401 AGCATGTAGA GTTGTCTAAA GCACCCATTG TCTTCTTTGA CTATCCAGAA
5451 TTTGCAAGAA TGACATTTCA TTGTAATTCT GAGGAATTAT TACTTTATGC
5501 TTTGCATAGG ATATTTAGTT CTGCAATAGA AAATGGAATG TATAAACGAT
5551 TGAGATTTAC TCAACCTATC ATAACTGATG GTCATGACAG CTACTTCAGG
```

FIG. 2E

```
5601  ATACAAAACA GGCCCCATTC TGATGAGGCC TATTTAATTT GCACAGAGGA
5651  TGAAATGAAG CTCTCAAATA AGTTTAAAGA CTAAATTTAT ATTTTCCTCA
5701  GTATCTTAAA AACAATATTC ATTAAATTGG AAAGCCCGCA ATGATTGTTG
5751  CAGTATCAAT GCGGGCATCA GTATCCAGCT CTTGCAATAC ACGGAAGTAT
5801  CAAGAAGCGA ATCAGGATTC TAACCATACC TTTTTAATTG CAACAATCTA
5851  ATTTCCATAA CATGTGTAGC TACATCGAAA AAAAGACCTC GAAGAGGTTG
5901  CAAGAGCGTC CAGCTCGCGG CATCAAAAGA CCCTAGTCTT TTGACAAGGG
5951  GGAGCCAAAA AACTGAGGTG GAGGAGCTTG CCGACGAAGC CAGGAAGCCC
6001  CAGCGTCCGG
```

FIG. 3

```
  1  MALSWNEIRR KAIEFSKRWE DASDENSQAK PFLIDFFEVF GITNKRVATF
 51  EHAVKKFAKA HKEQSRGFVD LFWPGILLIE MKSRGKDLDK AYDQALDYFS
101  GIAERDLPRY VLVCDFQRFR LTDLITKESV EFLLKDLYQN VRSFGFIAGY
151  QTQVIKPQDP INIKAAERMG KLHDTLKLVG YEGHALELYL VRLLFCLFAE
201  DTTIFEKSLF QEYIETKTLE DGSDLAHHIN TLFYVLNTPE QKRLKNLDEH
251  LAAFPYINGK LFEEPLPPAQ FDKAMREALL DLCSLDWSRI SPAIFGSLFQ
301  SIMDAKKRRN LGAHYTSEAN ILKLIKPLFL DELWVEFEKV KNNKNKLLAF
351  HKKLRGLTFF DPACGCGNFL VITYRELRLL EIEVLRGLHR GGQQVLDIEH
401  LIQINVDQFF GIEIEEFPAQ IAQVALWLTD HQMNMKISDE FGNYFARIPL
451  KSTPHILNAN ALQIDWNDVL EAKKCCFILG NPPFVGKSKQ TPGQKADLLS
501  VFGNLKSASD LDLVAAWYPK AAHYIQTNAN IRCAFVSTNS ITQGEQVSLL
551  WPLLLSLGIK INFAHRTFSW TNEASGVAAV HCVIIGFGLK DSDEKIIYEY
601  ESINGEPLAI KAKNINPYLR DGVDVIACKR QQPISKLPSM RYGNKPTDDG
651  NFLFTDEEKN QFITNEPSSE KYFRRFVGGD EFINNTSRWC LWLDGADISE
701  IRAMPLVLAR IKKVQEFRLK SSAKPTRQSA STPMKFFYIS QPDTDYLLIP
751  ETSSENRQFI PIGFVDRNVI SSNATYHIPS AEPLIFGLLS STMHNCWMRN
801  VGGRLESRYR YSASLVYNTF PWIQPNEKQS KAIEEAAFAI LKARSNYPNE
851  SLAGLYDPKT MPSELLKAHQ KLDKAVDSVY GFKGPNTEIA RIAFLFETYQ
901  KMTSLLPPEK EIKKSKGKN*
``` pTBMmeI.1 IS RESISTANT TO MmeI CLEAVAGE

MmeI CLEAVAGE OF HEMI-METHYLATED SUBSTRATES

FIG. 6

| Top Strand:<br>5'-TCCG$\underline{A}$C-3' | / | Bottom strand:<br>5'-GTCGG$\underline{A}$-3' | $^3$H-COUNTS |
|---|---|---|---|
| unmethylated: | / | unmethylated | 19,972 |
| unmethylated: | / | methylated: | 14,447 |
| methylated: | / | unmethylated: | 1,266 |
| methylated: | / | methylated: | 917 |

'A' indicates position of N6-methyl adenine in the DNA substrate

FIG. 7A

```
PileUp of: @mme.list2

Symbol comparison table: GenRunData:blosum62.cmp  CompCheck: 1102

GapWeight: 6
                GapLengthWeight: 1

Name: mmelfeLORF3P = gi|28373198|ref|NP_783835.1|  (SEQ ID NO:3)
Name: mmeLre121P   = gi|27450519|gb|AA014619.1|AF465251_62 (SEQ ID NO:4)
Name: mme = MmeI amino acid sequence (SEQ ID NO:5)
Name: mmeNMA1791   = gi|15794682|ref|NP_284504.1|  (SEQ ID NO:6)
Name: mmeBSU0677   = gi|16077744|ref|NP_388558.1|  (SEQ ID NO:7)
Name: mmegcry      = gi|9945797|gb|AAG03371.1|  (SEQ ID NO:8)
Name: mmePflQ8     = gi|23451826|gb|AAN32874.1|AF461726_1 (SEQ ID NO:9)
Name: saro3834     = gi|23110638|gb|ZP_00096791.1|  (SEQ ID NO:10)
Name: mmeMSI135    = gi|20803963|emb|CAD31540.1| (SEQ ID NO:11)
Name: mmeCC0826    = gi|16125079|ref|NP_419643.1|  (SEQ ID NO:12)
Name: mmeDR0119.1  = gi|15807788|ref|NP_285443.1|  (SEQ ID NO:13)
Name: mmeDR2267    = gi|15807258|ref|NP_295988.1|  (SEQ ID NO:14)

1                                                    50
mmelfeLORF3P        ~~~~~~~~~~ ~~~~~~~MPT RQQAAREFVK TWS.SDKKGR EDADRQTFWN
mmeLre121P          ~~~~~~~~~~ ~~~~~~~~~~ ~~~~~~~~~~ ~~~~~~~~~~ ~~~~~~~~~~
         mme        ~~~~~~~~~~ ~~~MALSWNE IRRKAIEFSK RWE.DASD.. ENSQAKPFLI
   mmeNMA1791       ~~~~~~~~~~ ~~~~MKTLLQ LQTAAQNFAA YYK.DQTD.. ERREKDTF*N
   mmeBSU0677       ~~~~~~~~~~ ~~~~~MALID LEDKIAEIVN R.E.DHSD.. .......FLY
      mmegcry       MVMAPTTVFD RATIRHNLTE FKLRWLDRIK QWEAENRPAT ESSHDQQFWG
      mmePflQ8      ~~~~~~~~~~ ~~~~~~~~~~ ~~~~~~~~~~ ~~~~~~~~~~ ~~~~~~~~~~
      saro3834      ~~~~~~~~~~ ~~~~~~~~~~ ~~~~~~~~~~ ~~~~~~~~~~ ~~~~~~~~~~
     mmeMSI135      ~~~~~~~~~~ ~~MSLGAAGL TPITPAAFIK KWRKSELG.. ERQAAQEHFL
     mmeCC0826      ~~~~~~~~~~ ~~~~~~~~~~ ~~MTPAQFVK KWSDSQLR.. ERQASQEHFL
    mmeDR0119.1     ~~~~~~~~~~ ~~~~~~~~~~ ~~MHPQEFAD TWSRRALKAT ERDSYVQHWL
      mmeDR2267     ~~~~~~~~~~ ~~~~~MPQTE TAQRMEDFVA YW..RTLKGD EKGESQV.FL 51                                                   100
mmelfeLORF3P        DLLQRVYGID N.YYDYITYE KDVQVKADGK VTTRRIDGYI P.STKIMVEM
mmeLre121P          ~~~~~~~~~~ ~~~~~~~~~~ ~~~~~~~~~~ ~~~~~~~~~~ ~~~~~~~~~~
         mme        DFFE.VFGIT N.KR...VAT FEHAVKKFAK AHKEQSRGFV DL...FWPGI
   mmeNMA1791       EFFA.IFGID R.KN...VAH FEYPVKD..P ADNTQ...FV DI...FWEGI
   mmeBSU0677       ELLG.VYDVP R.AT...ITR ....LKK.GN QNLTKRVGEV HLKNKVW...
      mmegcry       DLLDC.FGV. N.ARDLYLY. .....QRSAK RASTGRTGKI DM...FMPGK
      mmePflQ8      ~~~~~~~~~~ ~~~~~~~~~~ ~~~~~~~~~~ ~~~~~~~~~~ ~~~~~~~~~~
      saro3834      ~~~~~~~~~~ ~~~~~~~~~~ ~~~~~~~~~~ ~~~~~~~~~~ ~~~~~~~~~M
     mmeMSI135      D.ICSLVGHP SP.SDEDPTG AFFAFEKGAN KLG.GGKGFA D.VWK..KGH
     mmeCC0826      D.LCRMLEVP TP.AEDDPLG ERYCFERGAA KTG.GGDGWA D.VWR..KGC
    mmeDR0119.1     D.LCQLLHHE APGADPD... ..YKFERRVT KVGTKDKGFA D.VFK..KAH
      mmeDR2267     DRLFQAFGH. ...AGYKEAG AE..LEYRVA KQG.GGKKFA DLLWR..PRV 101                                                  150
mmelfeLORF3P        KGKNIKDLSK PITQSGGD.. .......ELT PFEQAKRYAN FLPN...SEQ
mmeLre121P          ~~~~~~~~~~ ~~~~~~~~~~ ~~~~~~~~~~ ~~~~~~~~~~ ~~~~~~~~~~
         mme        LLIEMKSRGK DL:....D.. .......KAY D..QALDYFS GIAERD...L
   mmeNMA1791       FLAEHKSANK NL.....T.. .......KAK E..QAERYLQ EIGRTKPSAL
```

FIG. 7B

```
                151                                                    200
mmelfeLORF3P    PR........ WILVSNFNEI DIHDM..E... .RPLDEPKVI KL........
   mmeLre121P   ~~~~~~~~~~ ~~~~~~~~~~ ~~~~~~~~~~ ~~~~~~~~~~ ~~~~~~~~~~
          mme   PR........ YVLVCDFQRF RLTDLITK... .ESVE....F LL........
    mmeNMA1791  PE........ YYAVSDFAHF HLYRRVPE... .EGAENQWQF PL........
    mmeBSU0677  PR........ YLLVTDYDGV LAKDTKTL... .EALDVKF.. ..........
       mmegcry  PA........ YVVCSNFETL RVTRLNRTYV GDSADWDITF PL........
      mmePf1Q8  ~~~~~~~~~~ ~~~~~~~~~~ ~~~~~~~~~~ ~~~~~~~~~~ ~~~~~~~~~~
      saro3834  PGAVLQRNHI HIATCDAGNV DRTLAALRKS PKTASQKARF ILATDGVAFQ
    mmeMSI135   ....L..SPP LHIVCDIERL RIHTAWTNTV PSTY..VITL DDLAE.....
    mmeCC0826   ....Q..NPP YLVVSDMERI IVHTNWTNTI SRKI..EFTL DDLHE.....
   mmeDR0119.1  ....G..NPP LLLTSDFQRI EINTAFTGTS PKSY..LITL DDIAENRVVG
    mmeDR2267   ....VPDRPR YAVLCNFDEL .....WVYDF NQQ......L DEPMDRLRI.

201                                                    250
mmelfeLORF3P    .EDLPKKVKS L........E F.....MVDA NQQQVIDEKQ LSVDAGNLVA
   mmeLre121P   ~~~~~~~~~~ ~~~~~~~~~~ ~~~~~~~~~~ ~~~~~~~~~~ ~~~~~~~~~~
          mme   .KDLYQNV.R S......... FGFIA...GY QTQVIKPQDP INIKAAERMG
    mmeNMA1791  .EELPEYITR G........V FDFMF...GI EAKVRQIQEE ANIQAAATIG
    mmeBSU0677  .EELPQY... .......... FDFFLAWKGI EKVEFEKENP ADIKAAERFA
       mmegcry  .AEIDEHIEQ L........A F.....LADY ETSAYREEEK ASLEASRLMV
      mmePf1Q8  ~~~~~~~~~~ ~~~~~~~~~~ ~~~~~~~~~~ ~~~~~~~~~~ ~~~~~~~~~~
      saro3834  AEDMASGETV ACNYAAFPDK FAFFLPLAGI TTVQQIRESS FDIKATGRLN
    mmeMSI135   ....PSAREM LHNVFFSPEK .........L RPTR..TRAA VTKEAADKFS
    mmeCC0826   ....PEKLAM LRQVFDGSDS .........L KPKI..SPQE LTAKVAQRFG
   mmeDR0119.1  GNDVP.ALQI LHSALHQPYD .........L DPRL..FRER ITTDATRQVG
    mmeDR2267   .EELPERYTV LNFMFEQ..E .........R APLFGNNRVD VTREAADSVA 251                                                    300
mmelfeLORF3P    KIYNELTNAY AAGRGIDVN. ...EPRIQRS LN..MLIVRL VFLLYADDSN
   mmeLre121P   ~~~~~~~~~~ ~~~~~~~~~~ ~~~~~~~~~~ ~~~~~~~~~~ ~~~~~~~~~~
          mme   KLHDTL.K.. ......LVG. ....YE.GHA LE..LYLVRL LFCLFAEDTT
    mmeNMA1791  RLHDAL.K.. ......EEG. ....IYE.EHE LR..LFITRL LFLFFADDSA
    mmeBSU0677  RIYDVLRK.. ......ENN. ....IIETNRG LD..LFLIRL LFCFFAEDTD
       mmegcry  ELFRAMNGDD VDEAVGDDAP TTPEEEDERV MRTSIYLTRI LFLLFGDDAG
      mmePf1Q8  ~~~~~~~~~~ ~~~~~~~~~~ ~~~~~~~~~~ ~~~~~~~~~~ ~~~~~~~~~~
      saro3834  KLYVELLKDN PDWA...... ........SRS EDMNHFMARL IFCFFAEDTD
    mmeMSI135   AIALRVQGR. G.TPD..... .......... .EIAHFVNQL VFCFFAQSVS
    mmeCC0826   DLGRRLQER. GHHPR..... .......... .DVAHFLNRV VFCMFAEDAK
   mmeDR0119.1  LVARRLGERE GRT....... .......... .RAAHMMMRV VFALFAEDTG
    mmeDR2267   KVLNSVIAR. GEDRA..... .......... .RAQRFLLQC VMAMFAEDFE 301                                                    350
mmelfeLORF3P    LFGKEDIFQA FIER...REP RDIRRDLSEL FKVLDQP.EE QRDPYLDDEF
   mmeLre121P   ~~~~~~~~~~ ~~~~~~~~~~ ~~~~~~~~~~ ~~~~~~~~~~ ~~~~~~~~~~
          mme   IFEKS.LFQE YIETKTLEDG SDLAHHINTL FYVLNTP.EQ KRLKNLDEHL
    mmeNMA1791  VFRRNYLFQD FLE..NCKEA DTLGDKLNQL FEFLNTP.DQ KRSKTQSEKF
    mmeBSU0677  IFKRNS.FTN LIKTLTEEDG SNLNKLFADL FIVL.....DK NERDDVPSYL
```

(Top portion before position 151:)

```
    mmeBSU0677  .FKEAK.KGK LF.....D.. .......ALI DIEQQVEYL. ........SAK
       mmegcry  VIGEAKSLGV PLDDA..... .......... .YAQALDYLL G.GTIANSHM
      mmePf1Q8  ~~~~~~~~~~ ~~~~~~~~~~ ~~~~~~~~~~ ~~~~~~~~~~ ~~~~~~~~~~
      saro3834  NPVEIEEAVS DLARAPYDAS EFPFQFLAAF GNKQTTLQRL RAGNSNQSDL
    mmeMSI135   FAWEYKRKKG NLDEA..... .......... .LLQLMRYAP AL........
    mmeCC0826   FGWEYKGKHK NLDAA..... .......... .LRQLQAYAL DL........
   mmeDR0119.1  FITEYKRPGS DLGAA..... .......... .LQQATLYSR DL........
    mmeDR2267   LI.EMKKRGE KLANH..... .......... .YQQAFDYWL KL........
```

FIG. 7C

```
mmegcry      LWDTPHLFAD FVRNETTPE. .SLGPQLNEL FSVLNTA.PE KRPKRLPSTL
mmePf1Q8     ~~~~~~~~~~ ~~~~~~~~~~ ~~~~~~~~~~ ~~~~~~~~~~ ~~~~~~~~~~
saro3834     IFVGEGLFSR TVETMSARDA SDTHMVIAEI FRAMDTRLAD RAAAGIKSWA
mmeMSI135    LLPD.GLFTK LLK.RSARAP ERAMSYLDKL FEAME..... RGGEF...DL
mmeCC0826    LLPE.GLFTR LTRSMQMRPP AEAAPQFDAL FAMMR..... AGGMF...GA
mmeDR0119.1  MLER.GIVTR LLE.RARAPP GEDQLYFQDL FGAMK..... GGGEF...WG
mmeDR2267    LIPR.GFFTE LADD.ARAGR GSSFDLFGGL FRQMNTSERA RGGRF.....

351                                                400
mmelfeLORF3P NQFAYVNGGM FSDENVIIPQ FTDELKRLIV EDAGRGFDWS GISPTIFGAV
mmeLre121P   ~~~~~~~~~~ ~~~~~~~~~~ ~~~~~~~~~~ ~~~~~~~~~~ ~~~~~~~~~~
mme          AAFPYINGKL FEEPLPPA.Q FDKAMREALL .DLCS.LDWS RISPAIFGSL
mmeNMA1791   KGFEYVNGGL FKERLRTF.D FTAKQHRALI .DCGN.FDWR NISPEIFGTL
mmeBSU0677   KEFPYVNGQL FTEPHTEL.E FSAKSRKLII .ECGELLNWA KINPDIFGSM
mmegcry      AKFPYVNGAL FAEPLAS.EY FDYQMREALL AAC..DFDWS TIDVSVFGSL
mmePf1Q8     ~~~~~~~~~~ ~~~~~~~~~~ ~~~~~~~~~~ ~~~~~~~~~~ ~~~~~~~~~~
saro3834     DVFPYVNGQL FSGS..TECPR FSKIARSYLL H..IGSLDWQ KINPDIFGSM
mmeMSI135    TDITWFNGGL FDGR...RALR LDDGDIGLL. .VAADSLDWG LIDPTIFGTL
mmeCC0826    DIVHWFNGGL FDEK...PALP LERADIKLIH DTAAEH.DWS DLDPSVFGNM
mmeDR0119.1  TDIRHFNGGL FDSE...DALA LTSEDAAAL. .IIAAKLDWS EVEPSIFGTL
mmeDR2267    APIPYFNGGL FRAV...DPIE LNRDELYLLH KAALEN.NWA RIQPQIFGVL 401                                                450
mmelfeLORF3P FESTLN.PET RRSGGMHYTS IENIHKVIDP LFLNDLHDEF D.........
mmeLre121P   ~~~~~~~~~~ ~~~~~~~~~~ ~~~~~~~~~~ ~~~~~~~~~~ ~~~~~~~~~~
mme          FQSIMD.AKK RRNLGAHYTS EANILKLIKP LFLDELWVEF E.........
mmeNMA1791   FQSVMD.AQE RREAGAHYTE AANIDKVING LFLENLRAEF E.........
mmeBSU0677   IQAVAS.EES RSYLGMHYTS VPNIMKVIKP LFLDKLNQSF ..........
mmegcry      FQLVKS.KEA RRSDGEHYTS KANIMKTIGP LFLDELRAEA D.........
mmePf1Q8     ~~~~~~~~~~ ~~~~~~~~~~ ~~~~~~~~~~ ~~~~~~~~~~ ~~~~~~~~~~
saro3834     IQAVAD.DEE RGALGMHYTS VPNILKVLNP LFLDDLRAKL E.........
mmeMSI135    FERFLD.PEK RAQIGAHYTD PEKIMRLVDP VILRPLRQEW EQARREIVEL
mmeCC0826    FEEALKATRE RAALGAHYTD REKILKIIDP VITWPLMAQW ETALAEIRAA
mmeDR0119.1  FENSLDV.DT RSRRGAHYTS VNDIERIVDR VVMEPLWAEW D.........
mmeDR2267    FQSSMDKKEQ HAK.GAHYTS EADIMRVVLP TIVTPFQRQI EAATTQ....

451                                                500
mmelfeLORF3P .......... .......... .......... .......... ....KIQNMG
mmeLre121P   ~~~~~~~~~~ ~~~~~~~~~~ ~~~~~~~~~~ ~~~~~~~~~~ ~~~~~~~~~~
mme          .......... .......... .......... .......... ....KVK...
mmeNMA1791   .......... .......... .......... .......... ....AVK..A
mmeBSU0677   .......... .......... .......... .......... .........L
mmegcry      .......... .......... .......... .......... ....KL..VS
mmePf1Q8     ~~~~~~~~~~ ~~~~~~~~~~ ~~~~~~~~~~ ~~~~~~~~~~ ~~~~~~~~~~
saro3834     .......... .......... .......... .......... .........E
mmeMSI135    LNGN...... .......... ...RKPPMRR. ..QQSRR... ...MKREEAA
mmeCC0826    LDARAAAEAE RKAVLEAAAE AMRADPVKAK AGEAARRKTL TAIAKRSDAA
mmeDR0119.1  .......... .......... .......... ....ALRLSL PELKK.....
mmeDR2267    .......... .......... .......... .......... ..........

501                                                550
mmelfeLORF3P NRRQRVTRAK AFRDKLGKLK FFDPACGSGN FLTETYLSLR KMENECLRII
mmeLre121P   ~~~~~~~~~~ ~~~~~~~~~~ ~~~~~~~~~~ ~~~~~~~~~~ ~~~~~~~~~~
mme          ...NNKNKLL AFHKKLRGLT FFDPACGCGN FLVITYRELR LLEIEVL.RG
mmeNMA1791   LKRDKAKKLA AFYQKIQNLQ FLDPACGCGN FLIVAYDRIR ALEDDIIAEA
mmeBSU0677   DAYDDYTKLE NLLTRIGKIK FFDPACGSGN FLIITYKELR RMEINIIKRL
mmegcry      SPSTSVAALE RFRDSLSELV FADMACGSGN FLLLAYRELR RIETDIIVAI
mmePf1Q8     ~~~~~~~~~~ ~~~~~~~~~~ ~~~~~~~~~~ ~~~~~~~~~~ ~~~~~~~~~~
```

FIG. 7D

```
            saro3834  .AGDNSRKLL NLRNRMAKIR VFDPACGSGN FLVIAYKQMR ELEAEI....
            mmeMSI135 .AEVR.SR.. .FTERLRKLR ILDPACGSGN FLYLALQGVK DIEHRANLDC
            mmeCC0826 LGQAK.DRLE AFLSRLAAFR VLDPACGSGN FLYVALHALK DIERRALVDA
            mmeDR0119.1 ..NVRLERLF AFQDRLTAVR ILDPACGSGN FLFVALKKLL DLEYQVRMAA
            mmeDR2267 ......KELR AILDELASFQ VLDPACGSGN FLYVAYRELR RLEARALL..

551                                              600
        mmelfeLORF3P  VGNQGA..LA LTDESEPKVK IQNFYGIEIN DFAVSVARTA MWIAESQMWE
         mmeLre121P   ~~~~~~~~~~ ~~~~~~~~~~ ~~~~~~~~~~ ~~~~~~~~~~ ~~~~~~~~~~
                mme   LHRGGQ..QV LDIEHLIQIN VDQFFGIEIE EFPAQIAQVA LWLTDHQMNM
           mmeNMA1791 LKDKAD..GL FD.SPSVQCR LKQFHGIEID EFAVLIARTA MWLKNHQCNI
           mmeBSU0677 QELLGE..YL Y..VPSV..T LSQFYGIEIE DFAHDVAKLS LWIAEHQMNE
             mmegcry  RQRRGETGMS LNIEWEQKLS IGQFYGIELN WWPAKIAETA MFLVDHQANK
             mmePf1Q8 ~~~~~~~~~~ ~~~~~~~~~~ ~~~~~~~~~~ ~~~~~~~~~~ ~~~~~~~~~~
            saro3834  NRRRGEADRR SD......IP LTNFRGIELR NFPAEIARLA LIIAEYQCDV
            mmeMSI135 ..EM..LG.M PAQLP..LVG PEILRGIEIN MMAAELARTT IWIG.DIQWQ
            mmeCC0826 ..ER..LG.L EVPTP..RVG LACVRGIEIE EYAAELARVT LWIG.DLQWH
            mmeDR0119.1 ..VMNDIGEF EMP.P..LVH PQQMLGIEIE TFAHELASIT LWMG.YFQWK
            mmeDR2267 ..RLRDLSAP GTALPPARVS IRQMHGLEYD PFGVELAKVT LTLAKELAIR 601                                              650
        mmelfeLORF3P  QTKDI..TFA NKDFLP.LDS NDSIYEGNAL RMDWNDI... ......VKPY
         mmeLre121P   ~~~~~~~~~~ ~~~~~~~~~~ ~~~~~~~~~~ ~~~~~~~~~~ ~~~~~~~~~~
                mme   KISDEFGNYF A..RIP.LKS TPHILNANAL QIDWNDV... ......LEAK
           mmeNMA1791 RTQIRFDGEV ACHTLP.LED AAEIIHANSL RTPW...... ........QAA
           mmeBSU0677 ELKNEVHNAV R.PTLP.LHT AGDIRCANAI RVEWTEVCP. ......AQGS
             mmegcry  ELANAVGR.. PPERLP.IKI TAHIVHGNAL QLDWADILS. ......ASAA
             mmePf1Q8 ~~~~~~~~~~ ~~~~~~~~~~ ~~~~~~~~~~ ~~~~~~~~~~ ~~~~~~~~~~
            saro3834  LYRGQ..KEA LAEFLP.LDS QNWITCGNAL RLDWLSICPP TGTAVKLQAN
            mmeMSI135 IKNGIRS... ..KSIPILRK LDAIERRDAL VRQAQDVDTA RDAQG.....
            mmeCC0826 AKNNYRG... ..FAEPILSS LDQIECRDAL L......... .NADG.....
            mmeDR0119.1 RAHG.GH... ..WETPILQR LDNIQNRDAL L......... .NPDG.....
            mmeDR2267 EMHDLLGNTG LDFDQPL..P LDNLD..DRI V......... ...QG.....

651                                              700
        mmelfeLORF3P  EL........ .......... DYIMGNPPFV GYSLQTKEQK QDIKQEFFKY
         mmeLre121P   ~~~~~~~~~~ ~~~~~~~~~~ ~~~~~~~~~~ ~~~~~~~~~~ ~~~~~~~~~~
                mme   KC........ .......... CFILGNPPFV GKSKQTPGQK ADL.LSVFGN
           mmeNMA1791 D......... .......... .YIFGNPPFI GSTYQTKEQK NDL.ESICGH
           mmeBSU0677 EE........ .......... VYVFGNPPYL GSKKQNKEHK SDM.LSIFGK
             mmegcry  K......... .......... TYIFGNPPFL GHATRTAEQA QELR.DLWG.
             mmePf1Q8 ~~~~~~~~~~ ~~~~~~~~~~ ~~~~~~~~~~ ~~~~~~~~~~ ~~~~~~~~~~
            saro3834  DLFEMPLDQA EIDFENEGGE TYICGNPPYL GAKKKSSDQI EDMKRV...G
            mmeMSI135 DLLAALQPVS EDAEAEWPEA EFIVGNPPFV GVRLMRQALG DPTVDRLFDV
            mmeCC0826 .......... ..TEAQWPAV DVIVGNPPFL GSKRLRDGLG NDYVERLFST
            mmeDR0119.1 .......... ..TEATWPRA DFIVGNPPFL GDKMMRSQLG EAYTTQLRET
            mmeDR2267 DALF...... ....TPWPRV DAIVGNPPFQ SKNKLQREMG AAYVKKLRAH 701                                              750
        mmelfeLORF3P  TDKY..GKFD YVSGWYIKGA KYIQ.NSTIK VGFVSTDSII QGEQAPEIWK
         mmeLre121P   ~~~~~~~~~~ ~~~~~~~~~~ ~~~~~~~~~~ ~~~~~~~~~~ ~~~~~~~~~~
                mme   LKSA..SDLD LVAAWYPKAA HYIQTNANIR CAFVSTNSIT QGEQVSLLWP
           mmeNMA1791 IKGY..GLLD YVCNWYVKAA GIMAQHPQVQ TAFVSTNSIC QGQQVEILWG
           mmeBSU0677 VKNG..KMLD YISAWFYFGA KYAST.TNAK VAFVSTNSVT QGEQVSILWN
             mmegcry  TKDI..SRLD YVTGWHAKCL DFFKSREG.R FAFVTTNSIT QGDQVPRLFG
             mmePf1Q8 ~~~~~~~~~~ ~~~~~~~~~~ ~~~~~~~~~~ ~~~~~~~~~~ ~~~~~~~~~~
            saro3834  LDKA..QLLD YVSAFIVRGL PLVAQQ.RCD MALVSTSSIC QGEQVSLIWP
```

FIG. 7E

```
mmelfeLORF3P  YDGRVSREAD  LVCYWVEKSR  AAVAADRTRR  VGLVTTNSIR  GGANRR.VLD
mmeCC0826     YRGKVPAEAD  FVAYWIAKAW  ELVQAQQGRR  AGLVTTNSVR  GGASRK.VLD
mmeDR0119.1   FKDRLPGQSD  LVCYWPEKAR  ALIEAGVTTR  AGFVTTNSIR  GGKNRV.VLE
mmeDR2267     YPD.VPGRAD  YCVYWIRKAH  D..QLGSGQR  AGLVGTNTIR  QNDSRVGGLD 751                                                     800
mmelfeLORF3P  VLFNDFHIFI  NYGYRSFEWN  NEAANKAKVD  VVIVGFSTK.  .EDKNPTIYD
mmeLre121P    ~~~~~~~~~~  ~~~~~~~~~~  ~~~~~~~~~~  ~~~~~~~~~~  ~VNKDKILYN
mme           LLLS.LGIKI  NFAHRTFSWT  NEASGVAAVH  CVIIGFGLKD  ..SDEKIIYE
mmeNMA1791    SLLN.QGIEI  HFAHRTFQWT  SQAAGKAAVH  CIIVGFRQKP  PMPSEKTLYD
mmeBSU0677    ELFK.FGIQI  NFAYKSFKWA  NNAKNNAAVI  VVIVGFG...  PLDTKVNKYL
mmegcry       PIFKA.GWRI  RFAHRTFAWD  SEAPGKAAVH  CVIVGFDKES  ..QPRPRLWD
mmePf1Q8      ~~~~~~~~~~  ~~~~~~~~~~  ~~~~~~~~~~  ~~~~~~~~~~  ~~~~~~~~~~
saro3834      RILKSAN..V  KFAYRPFRWS  NSAANNAGVY  CTIIGLTGSE  VSNKK.....
mmeMSI135     RIIA.ES.RL  FEAWSDEPWV  VDG...AAVR  VSLICFGHG.  .EDPLCL...
mmeCC0826     PIAD.AG.AL  MEAWADEPWA  LEG...AAVR  VSMFGFGDG.  .FAERRL...
mmeDR0119.1   RIKA.TG.DL  FMAWPDEPWQ  QNG...AAVR  VSLFGFDNG.  .TETLRT...
mmeDR2267     YVVQHGG.TI  TDAVGTQVWS  GD....AAVH  VSIVNWVKGP  AEGPKHLAWQ 801                                                     850
mmelfeLORF3P  EQKIIS....  ..A.KHINQY  MYDSDNIFID  TTRKY.IEA.  MPKMKTGNRP
mmeLre121P    SSN*ISH...  ..C.KNINGY  LFDGNNIFV.  TNRPAPLSN.  VPRMHNGCKL
mme           YESINGEPLA  IKA.KNINPY  LRDGVDVIA.  CKRQQPISK.  LPSMRYGNKP
mmeNMA1791    YPDIKGEPEK  HAV.ANINPY  LIDAPDLII.  AKRSRPIHC.  EPDMVNGSKP
mmeBSU0677    FVD...ETKK  L.V.SNISPY  LTDGENILV.  SSRTKPISD.  LPKLHFGNMP
mmegcry       YPDVKGEPVS  VEVGQSINAY  LVDGPNVLVD  KSR.HPISSE  ISPATFGNMA
mmePf1Q8      ~~~~~~~~~~  ~~~~~~~~~~  ~~~~~~~~~~  ~~~~~P.ADE  RSQMDAGGKP
saro3834      ...LFGEGSV  VEC.SSIAPY  LVPGPEI.IC  APRQSSIS.G  FARMVMGSNP
mmeMSI135     ..DGRT....  ...VAQINAD  LTAGVTDLTK  ARRL.S..EN  QNVAFMGDTK
mmeCC0826     ..EGRK....  ...AEHLHSD  FRGASTDVTK  ALRL.K..EN  ASIAFMGDTK
mmeDR0119.1   LNDGH.....  ...VGVINAD  LNAG.TDVKQ  AQKL.P..EN  AGVSFIGTQK
mmeDR2267     VGDHRTSPWQ  STELPVINSA  LSAG.TDVTQ  AQKL.RVNMN  SGACYQGQTH 851                                                     900
mmelfeLORF3P  ADGGALILSP  KEAKEL.VNE  EPQSKQ...F  IKKLTGSKEF  IT.GKYRYCL
mmeLre121P    LDGGFYTLTS  QERKEA.ISK  DPYADK...F  IRPYLGAKNF  IH.GTARYCI
mme           TDDGNFLFTD  EEKNQF.ITN  EPSSEK...Y  FRRFVGGDEF  IN.NTSRWCL
mmeNMA1791    TEGGNLILST  AEKDAL.IAA  EPLAEQ...Y  IRPFIGADEF  LN.GKTRWCL
mmeBSU0677    NDGGGLLFTI  TEYTDA.INK  YPELVP...Y  FKKFIGSVEF  IN.GGLRYCL
mmegcry       RDGGNLLVEV  DEYDEV.MS.  DPVAAK...Y  VRPFRGSREL  MN.GLDRWCL
mmePf1Q8      VEGGNLLFAE  EEKQRL.VEG  NVDVVK...F  LKRVYGASEY  IR.GEVRFCL
saro3834      VDGKRLIFEQ  DEKESV.VAA  DPRSER...F  FKRYGGTQEL  VN.GVDRWCL
mmeMSI135     G.GAFDVPGS  LARAWLSMPM  NPNGRPNSDV  LRPWRNGMDV  ARRG...RDM
mmeCC0826     G.GAFDVSGE  IAREWLRLPL  NPNGRPNSDV  LKPWRNAMDM  TRRS...SDK
mmeDR0119.1   G.GAFDIPGD  LARSWLSVP.  NPDRVSNADV  LKPWVNGMDL  TRRP...SGR
mmeDR2267     GHKGFLLDGL  EAGQMLSAE.  ....RKNAEV  IFPYLTGDEL  LRTSPPHPTR 901                                                     950
mmelfeLORF3P  WLVNVTP...  .KQLR..SMP  L..VLKRVE.  QCKENR.LSG  APDROKLAAT
mmeLre121P    WLKDANP...  .KDIH..QSP  F..ILDRIN.  KVAEFRSQQK  SKDTQKYAKR
mme           WLDG.ADIS.  ..EIR..AMP  L..VLARIK.  KVQEFRLKSS  AKPTRQSAST
mmeNMA1791    WFHGVSDVKR  NHDLK..QMP  Q..VQARIQ.  AVKTMREASS  DKQTQKDAAT
mmeBSU0677    WLNE....AK  YEKIK..SNP  L..IQERIS.  ISKNHREKST  DKGTNKLALT
mmegcry       WLVDVAP...  .SDIA..QSP  V..LKKRLE.  AVKSFRADSK  AASTRKMAET
mmePf1Q8      WISD....SQ  EQEAK..SNS  D..INCKLN.  AVAAFRLKSP  KAATKKGAAW
saro3834      WIND....DQ  VDDAK..AIA  E..IAKVLE.  SCRSYR.QGA  GRDAQKAANR
mmeMSI135     WIVDFGWEMS  EQEAALYEAP  FQHIREHVFP  ........ER  SKN.......
```

FIG. 7F

```
   mmeCC0826  WIIDFGWTMS EADAALFETP FRHVLLHVKP ........ER DRN.......
  mmeDR0119.1  WIIDFA.QMD EGEARQYLQP MAYVEQKIRP ........ER ATN.......
   mmeDR2267  YVIDF.QPRD VFGARAYKLP FARIEREVLP TRQAAAAEEE ARNAEVLAAN 951                                           1000
 mmelfeLORF3P  P......... ........HL ......FREQ MNPDNYMIVP LVTGCRRKYV
  mmeLre121P   P......... ........ML PTRLAYYSHD EHTD.MLIVP ATSSQRREYL
         mme   P......... ........M. ..KFFYISQP .DTDY.LLIP ETSSENRQFI
   mmeNMA1791  P......... ........W. ..LFQKIRQP SDGNY.LIIP SVSSESRRFI
   mmeBSU0677  P......... ........W. ..KFRDTHE. .TTNYSIVVP SVSSENRFYI
     mmegcry   P......... ........HL FGQ....RSQ PDTDY.LCLP KVVSERRSYF
     mmePf1Q8  P......... ........H. ..KFEEVKQI GN.EVVTIVP KVSSESREYL
     saro3834  P......... ........HS FC.YRTFQE. ...NIGIHVG LTIGNGLSHV
   mmeMSI135   ....RRDAYR ...ERWWRHV EPRPAFHASL QGHSRYMATP RV.AKHRTFV
   mmeCC0826   ....NREMYR ...LNWWKHV EPROGLMKRV PALSRLLVTP EV.SKHRLFI
  mmeDR0119.1  ....SDRPSR ...ERWWLHQ RSRPELREAT IELDRFIGIP RV.AKHLLPV
   mmeDR2267   PKAKTNKHHR NFLNQWWALS YGRSEMIEKI SSLSRYIVCS RV.TKRQVFE 1001                                          1050
 mmelfeLORF3P  PFGYLG.NDI IPTNLATIIP EADHYAFGVL ESIVHMAWMR VVA...GRKG
  mmeLre121P   PIGYVSEKNI VSYSL.MLIP NASNFNFGIL ESKVHYIWLK NFC...GRLK
         mme   PIGFVDRNVI SS.NATYHIP SAEPLIFGLL SSTMHNCWMR NVG...GRLE
   mmeNMA1791  PIGYLSFETV VS.NLAFILP NATLYHFGIL SSTMHNAFMR TVA...GRLK
   mmeBSU0677  PMGLAGADTI LS.NLIYVIY DAEIYLLGIL MSRMHMTWVK AVA...GRLK
     mmegcry   TVQRYPSNVI AS.DLVFHAQ DPDGLMFALA SSSMFITWQK SIG...GRLK
     mmePf1Q8  PVGLLPRGSI VT.DLAFALY DAPLWNMALI ASRLHLVWIG ~~~~~~~~~~
     saro3834  PAD.LKSSGF VSSHTAYMIY GWHPVEFALL NSRLMLVWTE TVG...GRLG
   mmeMSI135   WLD....QAI VPDSRIFAFS RSDDVFFGIL HSRFHEAWSF GTCSWHGV.G
   mmeCC0826   WLD....ARV LPDHKLQVVT LDDDCSFGVL HSRFHEVWAL AAGSWHGS.G
  mmeDR0119.1  WLP....EGT LPDSQVVVIA RDDDFIFGVL ASTIHRSWAR MQGTYMGV.G
   mmeDR2267   FLD....NGI RPSDGLQIFA FEDDYSFGVI QSSVHWQWLI ARG...GTLT 1051                                          1100
 mmelfeLORF3P  TSYRYSKNLV YTNFPWPV.V DINQKEK... .......ITI TAQDILNARN
  mmeLre121P   SDYRYSNTII YNNFPWPT.V GDKQEQN... .......ISE TAQGILNTRK
         mme   SRYRYSASLV YNTFPWIQ.. ....PNEKQ. ....SKAIEE AAFAILKARS
   mmeNMA1791  SDYRYSNTVV YNNFPFPE.. SCRLPSENDR PDPLRAAVEA AAQTVLDARG
   mmeBSU0677  TDYRYSAGLC YNTFPIPE.L STRRKNE... ....IEE AILEILDLR.
     mmegcry   SDLRFANTLT WNTFPVPE.L DEKTRQR... ....IIK AGKKVLDARA
     mmePf1Q8  ~~~~~~~~~~ ~~~~~~~~~~ ~~~~~~~~~~ ~~~~~~~~~~ ~~~~~~~~~~
     saro3834  NGMRFSNTIV YNTFPVPS.L TDQNK..... .....ADLTR CAEDILLARE
   mmeMSI135   NDPTYNSAGV FETFPFPEGL TPDIPAVRYE KDSRAIAISK AAKRLDDIRN
   mmeCC0826   NDPRYTISTT FETFPFPEGL TPNIAAVDYE GDPRAQAIAA AAAELNRLRE
  mmeDR0119.1  NDLRYTPSTC FETFPVP... APT....... .DEQRAEIEK WAKYIVQLRE
   mmeDR2267   ARLMYTSDTV FDTFPWP*D. .PTLAQVR.. ......AVAA AAVKLRELRN 1101                                          1150
 mmelfeLORF3P  .......... .......... ...LY..... ....PDSSLA DLYDPLTMPI
  mmeLre121P   .......... .......... ...LY..... ....PDSSLA DLYDPLTMPV
         mme   .......... .......... ...NY..... ....PNESLA GLYDPKTMPS
   mmeNMA1791  .......... .......... ...QYRREAQ EAGLPEPTLA ELYAPDAGYT
   mmeBSU0677  .......... .......... .......... ..EE QGG....TLA ELYNPSTMPI
     mmegcry   .......... .......... ...LH..... ....PERSLA EHYNPLAMAP
     mmePf1Q8  ~~~~~~~~~~ ~~~~~~~~~~ ~~~~~~~~~~ ~~~~~~~~~~ ~~~~~~~~~~
     saro3834  .......... .......... ......SHFP ........ATIA DLYDPETMPE
   mmeMSI135   AWLNPSDLVQ IKPEVVPGYP DRILPKDIAS DAILRDRTLT NLYNR.....
   mmeCC0826   AWLNPPDLVR IEPEVVPGYP DRVLPVSPEA GAELKKRTLT NLYNQ.....
```

FIG. 7G

```
mmeDR0119.1    HLLN..... .......... ..........Q DA...KGTLT GIYNQLEKLR
mmeDR2267      KVMREQ.... ......GW. ...........SLR DLYRTLDMPG 1151                                                1200
mmelfeLORF3P   E......... .LRKAHEAND KAVLKAYGLK P.SATEPEI. .VQHLFKMYE
mmeLre121P     E......... .LRKAHEAND KAVLKAYGLS P.KATEQEI. .VEHLFKMYE
mme            E......... .LLKAHQKLD KAVDSVYGFK .GPNT..EIA RIAFLFETYQ
mmeNMA1791     A......... .LDKAHATLD KAVDKAYGYK TGKNTDDEAE RVAFLFELYR
mmeBSU0677     E......... .LKVAHEKLD GIVERAYRQK QFES..DE.E RLEVLLKLYQ
mmegcry        E......... .LIKAHDALD REVDKAFGAP RKLTTVRQ.. RQELLFANYE
mmePf108       ~~~~~~~~~~ ~~~~~~~~~~ ~~~~~~~~~~ ~~~~~~~~~~ ~~~~~~~~~~
saro3834       S......... .LRAAHDRND EVLERIY... IGRRFRNDTE RLEKLFELYT
mmeMSI135      ......RP.Q WLVDAHSDLD AAVAGAYGWP ADIS...EDE ALANLLELNL
mmeCC0826      ......RP.A WLDMAHQRLD AAVAAAYGWP DGLT...DDE ILERLFALNQ
mmeDR0119.1    NSPDAAHPVS ALATAHDKLD QAVATAYGWE WPLN...EDQ VLERLLALNL
mmeDR2267      KNP....... .LRDAQERLD AAVSAAYGLP AGA......D MLDFLLALNA 1201                                                1250
mmelfeLORF3P   KLTKKDW~~~ ~~~~~~~~~~ ~~~~~~~~~~ ~~~~~~~~~~ ~~~~~~~~~~
mmeLre121P     KLTKGER*~~ ~~~~~~~~~~ ~~~~~~~~~~ ~~~~~~~~~~ ~~~~~~~~~~
mme            KMTSLLPPEK EIKKSKGKN* ~~~~~~~~~~ ~~~~~~~~~~ ~~~~~~~~~~
mmeNMA1791     KAAAIA~~~~ ~~~~~~~~~~ ~~~~~~~~~~ ~~~~~~~~~~ ~~~~~~~~~~
mmeBSU0677     EMTER~~~~~ ~~~~~~~~~~ ~~~~~~~~~~ ~~~~~~~~~~ ~~~~~~~~~~
mmegcry        KLISHQP~~~ ~~~~~~~~~~ ~~~~~~~~~~ ~~~~~~~~~~ ~~~~~~~~~~
mmePf108       ~~~~~~~~~~ ~~~~~~~~~~ ~~~~~~~~~~ ~~~~~~~~~~ ~~~~~~~~~~
saro3834       KMTGGRSSEG GAA~~~~~~~ ~~~~~~~~~~ ~~~~~~~~~~ ~~~~~~~~~~
mmeMSI135      AREAFNEHAK SGLKTRKPRR RPTPEEVRRA PQMKLPIAGG RKSVVGPQQL
mmeCC0826      ERAAAGR~~~ ~~~~~~~~~~ ~~~~~~~~~~ ~~~~~~~~~~ ~~~~~~~~~~
mmeDR0119.1    ERCPA~~~~~ ~~~~~~~~~~ ~~~~~~~~~~ ~~~~~~~~~~ ~~~~~~~~~~
mmeDR2267      XVAAAEARGA AVTGPGLPAG LNTADFVTAD AVRPLG*~~~ ~~~~~~~~~~

1251       1273
mmelfeLORF3P   ~~~~~~~~~~ ~~~~~~~~~~ ~~~
mmeLre121P     ~~~~~~~~~~ ~~~~~~~~~~ ~~~
mme            ~~~~~~~~~~ ~~~~~~~~~~ ~~~
mmeNMA1791     ~~~~~~~~~~ ~~~~~~~~~~ ~~~
mmeBSU0677     ~~~~~~~~~~ ~~~~~~~~~~ ~~~
mmegcry        ~~~~~~~~~~ ~~~~~~~~~~ ~~~
mmePf108       ~~~~~~~~~~ ~~~~~~~~~~ ~~~
saro3834       ~~~~~~~~~~ ~~~~~~~~~~ ~~~
mmeMSI135      TTKDRENQPT SAERPRNTKR RTS
mmeCC0826      ~~~~~~~~~~ ~~~~~~~~~~ ~~~
mmeDR0119.1    ~~~~~~~~~~ ~~~~~~~~~~ ~~~
mmeDR2267      ~~~~~~~~~~ ~~~~~~~~~~ ~~~
```

RECOMBINANT TYPE II RESTRICTION ENDONUCLEASES, MMEI AND RELATED ENDONUCLEASES AND METHODS FOR PRODUCING THE SAME

BACKGROUND OF THE INVENTION

The present invention relates to a DNA (deoxyribonucleic acid) fragment, which fragment codes for one polypeptide possessing two related enzymatic functions, namely an enzyme which recognizes the DNA sequence 5'-TCC(Pu) AC-3' and cleaves the phosphodiester bond between the 20th and 21st residues 3' to this recognition sequence on this DNA strand, and between the 18th and 19th residues 5' to the recognition sequence on the complement strand 3'-AGG(Py) TG-5' to produce a 2 base 3' extension (hereinafter referred to as the MmeI restriction endonuclease), and a second enzymatic activity that recognizes the same DNA sequence, 5'-TCC(Pu)AC3', but modifies this sequence by the addition of a methyl group to prevent cleavage by the MmeI endonuclease. The present invention also relates to a vector containing the DNA fragment, a transformed host containing this DNA fragment, and an improved process for producing MmeI restriction endonuclease from such a transformed host. The present invention also relates to a process for identifying additional DNA fragments that encode enzymes having the same general properties as MmeI but potentially having unique DNA recognition sequences. This process depends on the use of the amino acid sequence of the MmeI enzyme presented in this application, or subsequently on the additional sequences identified through this process. The invention also relates to additional DNA fragments, identifiable through the process described, each of which encodes a polypeptide having significant amino acid sequence similarity to the MmeI polypeptide. The polypeptides encoded by these DNA fragments are predicted to perform similar functions to MmeI. Specifically, they are predicted to possess the dual enzymatic functions of cleaving DNA in a specific manner at a relatively far distance from the specific recognition sequence and also modifying their recognition sequences to protect the host DNA from cleavage by endonuclease activity. An example of such an enzyme identified by this process is CstMI (see U.S. application Ser. No. 10/616,689, filed concurrently herewith). CstMI was identified as a potential endonuclease because of its highly significant amino acid sequence similarity to MmeI. CstMI recognizes the sequence 5'-AAGGAG-3' and cleaves the phosphodiester bond between the 20th and 21st residues 3' to the recognition sequence on this DNA strand, and between the 18th and 19th residues 5' to the recognition sequence on the complement strand 5'-CTCCTT-3' to produce a 2 base 3' extension.

Restriction endonucleases are a class of enzymes that occur naturally in prokaryotes. There are several classes of restriction systems known, of which the type II endonucleases are the class useful in genetic engineering. When these type II endonucleases are purified away from other contaminating prokarial components, they can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, the type II endonucleases cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence; HaeII, which recognizes 5'-(Pu)GCGC(Py)-3' typifies restriction endonucleases having a degenerate or relaxed recognition sequence; while BspMI, which recognizes 5'-ACCTGC-3' typifies restriction endonucleases having an asymmetric recognition sequence. Type II endonucleases with symmetrical recognition sequences generally cleave symmetrically within or adjacent to the recognition site, while those that recognize asymmetric sequences tend to cleave at a distance of from 1 to 20 nucleotides to one side of the recognition site. The enzyme of this application, MmeI, (along with CstMI) has the distinction of cleaving the DNA at the farthest distance from the recognition sequence of any known type II restriction endonuclease. More than two hundred unique restriction endonucleases have been identified among several thousands of bacterial species that have been examined to date.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer cleaved by the restriction endonuclease. The DNA of a bacterial cell is modified by virtue of the activity of its modification methylase and it is therefore insensitive to the presence of the endogenous restriction endonuclease. It is only unmodified, and therefore identifiably foreign, DNA that is sensitive to restriction endonuclease recognition and cleavage. Modification methyltransferases are usually separate enzymes from their cognate endonuclease partners. In some cases, there is a single polypeptide that possesses both a modification methyltransferase function and an endonuclease function, for example, Eco57I. In such cases, there is a second methyltransferase present as part of the restriction-modification system. In contrast, the MmeI system of the present application has no second methyltransferase accompanying the endonuclease-methyltransferase polypeptide.

Endonucleases are named according to the bacteria from which they are derived. Thus, the species Haemophilus aegyptius, for example synthesizes 3 different restriction endonucleases, named HaeI, HaeII and HaeIII. These enzymes recognize and cleave the sequences 5'-(W)GGCC (W)-3',5'-(Pu)GCGC(Py)-3' and 5'-GGCC-3' respectively. Escherichia coli RY13, on the other hand, synthesizes only one enzyme, EcoRI, which recognizes the sequence 5'-GAATTC-3'.

While not wishing to be bound by theory, it is thought that in nature, restriction endonucleases play a protective role in the welfare of the bacterial cell. They enable bacteria to resist infection by foreign DNA molecules such as viruses and plasmids that would otherwise destroy or parasitize them. They impart resistance by binding to infecting DNA molecules and cleaving them in each place that the recognition sequence occurs. The disintegration that results inactivates many of the infecting genes and renders the DNA susceptible to further degradation by exonucleases.

More than 3000 restriction endonucleases have been isolated from various bacterial strains. Of these, more than 240 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

Restriction endonucleases have traditionally been classified into three major classes; type I, type II and type III. The type I restriction systems assemble a multi-peptide complex consisting of restriction polypeptide, modification polypeptide, and specificity, or DNA recognition, polypeptide. Type I systems require a divalent cation, ATP and S-adenosylmethionine (SAM) as cofactors. Type I systems cleave DNA at random locations up to several thousand basepairs away from their specific recognition site. The type III systems generally recognize an asymmetric DNA sequence and cleave at a specific position 20 to 30 basepairs to one side of the recognition sequence. Such systems require the cofactor ATP in addition to SAM and a divalent cation. The type III systems assemble a complex of endonuclease polypeptide and modification polypeptide that either modifies the DNA at the recognition sequence or cleaves. Type III systems produce partial digestion of the DNA substrate due to this competition between their modification and cleavage activities, and so have not been useful for genetic manipulation.

MmeI does not require ATP for DNA cleavage activity and it cleaves to completion; thus it can be classified as a type II endonuclease. Unlike other type II enzymes, however, MmeI consists of a single polypeptide that combines both endonuclease and modification activities and is sufficient by itself to form the entire restriction modification system. MmeI also cleaves the farthest distance from the specific DNA recognition sequence of any type II endonuclease (as does CstMI of this application). MmeI is quite large and appears to have three functional domains combined in one polypeptide. These consist of an amino-terminal domain which contains the endonuclease DNA cleavage motif and which may also be involved in DNA recognition, a DNA modification domain most similar to the gamma-class N6mA methyltransferases, and a carboxy-terminal domain presumed to be involved in dimer formation and possibly DNA recognition. The enzyme requires SAM for both cleavage and modification activity. The single MmeI polypeptide is sufficient to modify the plasmid vector carrying the gene in vivo to provide protection against MmeI cleavage in vitro, yet it is also able to cleave unmodified DNAs in vitro when using the endonuclease buffer containing Mg++ and SAM.

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel DNA fragment encoding a novel restriction endonuclease, obtainable from *Methylophilus methylotrophus* (NEB#1190). The endonuclease is hereinafter referred to as "MmeI", which endonuclease:

(1) recognizes the degenerate nucleotide sequence 5'-TCC(Pu)AC-3' in a double-stranded DNA molecule as shown below:

```
5'-TCC(Pu)AC-3'

3'-AGG(Py)TG-5'
```

(wherein G represents guanine, C represents cytosine, A represents adenine, T represents thymine, (Pu) represents a purine, either A or G, and (Py) represents a pyrimidine, either C or T);

(2) cleaves DNA in the phosphodiester bond following the 20th nucleotide 3' to the recognition sequence 5'-TCC(Pu)AC-3 and preceding the 18th nucleotide 5' to the complement strand of the recognition sequence 3'-AGG(Py)TG-5' to produce a 2 base 3' extension:

```
5'-TCC(Pu)AC(N20)/-3'

3'-AGG(Py)T(N18)/-5';
```

(3) methylates the recognition sequence specified in (1) in vivo to protect the host DNA from cleavage by the MmeI endonuclease activity.

The invention further relates to additional DNA fragments, each of which is identified to encode polypeptides which share significant sequence similarity to the MmeI restriction-modification polypeptide. The DNA fragment encoding the MmeI polypeptide enables the identification of these additional potential endonucleases by using similarity searching of the MmeI sequence against sequences available in databases, such as GENBANK, using a program such as BLAST (Altschul, et al. Nucleic Acids Res. 25:3389–3402 (1997)). These DNA fragments, as well as any other fragments with such similarity to MmeI that may be deposited in the databases in the future, are candidates which may encode polypeptides that are similar to MmeI, in that the polypeptides encoded act as both restriction endonuclease and methyltransferase. These polypeptides may, like MmeI, cleave DNA at a similarly far distance from the recognition sequence, in the range of 18 to 20 nucleotides or more, which character is unique and useful in certain molecular biology technologies. Specifically these polypeptides contain amino acid motifs common to N6mA DNA methyltransferases in the middle of the polypeptide, have a motif common to restriction endonucleases and located in the aminoterminal section of the polypeptides, consisting of the amino acids D/E(X8–X12)D/EXK, and have a region of several hundred amino acids following the conserved methyltransferase motifs which are significantly similar to this region of MmeI and are believed to serve as a dimerization and possibly a DNA sequence recognition domain. An example of such a polypeptide, CstMI, is presented. CstMI has been shown to recognize the 6 base pair asymmetric sequence 5'-AAGGAG-3' and to cleave the DNA in the same manner as MmeI; 5'-AAGGAGN20/N18-3'. The endonuclease encoded by these DNA fragments may be produced by the process used for MmeI, as described below.

The present invention further relates to a process for the production of the restriction endonuclease MmeI. This process comprises culturing a transformed host, such as E. coli, containing the DNA fragment encoding the MmeI restriction system polypeptide, collecting the cultured cells, obtaining a cell-free extract therefrom and separating and collecting the restriction endonuclease MmeI from the cell-free extract. The present invention further relates to a process for the production of the restriction endonucleases encoded by the DNA sequences identified as homologous to MmeI. This process comprises culturing a transformed host, such as E. coli, containing the gene for these restriction systems, collecting the cultured cells, obtaining a cell-free extract therefrom and separating and collecting the restriction endonuclease from the cell-free extract.

BRIEF DESCRIPTION OF THE FIGURES

FIGS. 7A–7G Multiple sequence alignment of MmeI amino acid sequence (SEQ ID NO:3 through SEQ ID NO:14) and homologous polypeptides from public databases.

DETAILED DESCRIPTION OF THE INVENTION

Figure 1:
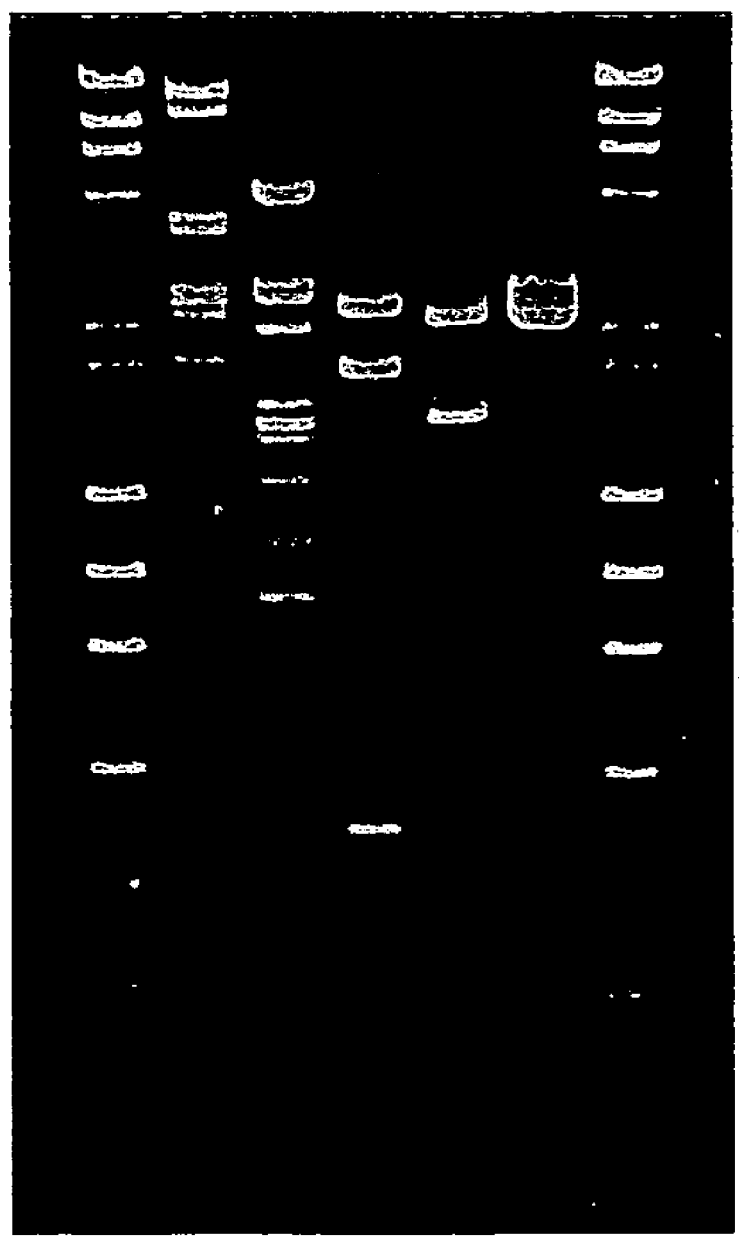
FIG. 1—Agarose gel showing MmeI cleavage of lambda, T7, phiX174, pBR322 and pUC19 DNAs.
  Lane 1: DNA size standards: lambda-HindIII, PhiX174-HaeIII
  Lane 2: lambda DNA+MmeI
  Lane 3: phage T7 DNA+MmeI
  Lane 4: PhiX174 DNA+MmeI
  Lane 5: pBR322 DNA+MmeI
  Lane 6: pUC19 DNA+MmeI
  Lane 7: DNA size standards: lambda-HindIII, PhiX174-HaeIII
FIGS. 2A–2E—DNA sequence of the MmeI gene locus
FIG. 3—Amino acid sequence of the MmeI gene locus
FIG. 4—Agarose gel showing MmeI cleavage of pTBMmeI.1 DNA and unmodified DNA substrates.
  Lane 1: DNA size standards: lambda-HindIII, PhiX174-HaeIII
  Lane 2: pTBMmeI.1 (not cut)
  Lane 3: pTBMmeI.1 digested with 2.5 units MmeI
  Lane 4: lane 3 plus 0.5 µg pRRS vector DNA
  Lane 5: lane 3 plus 0.5 µg pRRS PhiX174 DNA
  Lane 6: DNA size standards: lambda-HindIII, PhiX174-HaeIII
  Lane 7: PhiX174 DNA digested with 2.5 units MmeI
FIG. 5—Agarose gel showing MmeI cleavage of unmethylated, hemi-methylated and fully methylated DNA substrates.
  Lane 1: DNA size standards: lambda-BstEII, pBR322-MspI
  Lane 2: Unmethylated DNA (oligo1+oligo2) uncut
  Lane 3: Unmethylated DNA (oligo1+oligo2)+2.5 units MmeI
  Lane 4: Unmethylated DNA (oligo1+oligo2)+2.5 units Hpy188I
  Lane 5: Top methylated/bottom unmethylated DNA (oligo3+oligo2) uncut
  Lane 6: Top methylated/bottom unmethylated DNA (oligo3+oligo2)+MmeI
  Lane 7: Top methylated/bottom unmethylated DNA (oligo3+oligo2)+Hpy188I
  Lane 8: Top unmethylated/bottom methylated DNA (oligo2+oligo4) uncut
  Lane 9: Top unmethylated/bottom methylated DNA (oligo2+oligo4)+MmeI
  Lane 10: Top unmethylated/bottom methylated DNA (oligo2+oligo4)+Hpy188I
  Lane 11: Methylated DNA (oligo3+oligo4) uncut
  Lane 12: Methylated DNA (oligo3+oligo4)+MmeI
  Lane 13: Methylated DNA (oligo3+oligo4)+Hpy188I
  Lane 14: DNA size standards: lambda-BstEII, pBR322-MspI
FIG. 6—Incorporation of labeled methyl groups into unmethylated, hemi-methylated and fully methylated DNA substrates.

The recognition sequence and cleavage site of the endonuclease of the present invention were previously described (Boyd, Nucleic Acids Res. 14: 5255–5274 (1986)). However the MmeI enzyme proved difficult to produce from the native host, Methylophilus methylotrophus, due to very low yield of the enzyme and the relative difficulty of growing the M. methylotrophus host in large quantity. To overcome these limitations to producing MmeI, the present application describes the identification of the DNA sequence encoding the MmeI gene and the expression of this MmeI gene in a suitable host, in the present instance E. coli. This manipulation of the MmeI encoding DNA fragment results in both a significant increase in the amount of enzyme produced per gram of cells and a significant increase in ease of growth of large amounts of cells containing MmeI enzyme.

Several standard approaches typically employed by persons skilled in the art of cloning were applied to the task of cloning of MmeI without success. Specifically, the methylase selection approach (Wilson, et al., U.S. Pat. No. 5,200,333) was attempted unsuccessfully. Several random libraries of M. methylotrophus DNA were constructed in E. coli and challenged by digesting with MmeI, but no MmeI methylase containing clones were obtained.

A second approach was also attempted but failed. In this approach, antibodies specific for N6mA were used to screen a library of random clones constructed in a lambda phage replacement vector. The approach was successful in obtaining methylase positive clones, but all examined were found to express the methyltransferase of the second restriction system in M. methylotrophus, the MmeII methylase (recognition sequence 5'-GATC-3') rather than the desired MmeI methylase activity.

The successful approach to obtain the desired DNA fragment encoding the MmeI restriction system involved several steps. First a novel purification procedure was developed to purify the MmeI endonuclease peptide to homogeneity from M. methylotrophus. Once this ultra pure MmeI endonuclease polypeptide was successfully obtained in a significant amount, amino acid sequence from the amino terminus and from internal cyanogen-bromide degradation peptides was determined. Using the amino acid sequence obtained, degenerate DNA primers complementary to the DNA coding for the amino acid sequences were synthesized and used to PCR amplify a portion of the MmeI gene. The DNA sequence of this portion of the MmeI gene was determined. The entire MmeI endonuclease gene and surrounding DNA sequences were then obtained by applying the inverse PCR technique. A number of primers matching the DNA sequence obtained were designed, synthesized and used in combination with numerous different templates. The inverse PCR templates were produced by digesting *M. methylotrophus* genomic DNA with various restriction endonucleases and then ligating the cut *M. methylotrophus* DNA at low concentration to obtain circular molecules. The various primers were tried in combinations with the various templates to find primer-template combinations that produced a specific PCR amplification product. The products thus obtained were sequenced. Once the DNA sequence encoding the entire MmeI endonuclease gene was obtained, primers were designed to specifically amplify the gene from *M. methylotrophus* genomic DNA. The amplified gene was inserted into an expression vector and cloned into an *E. coli* host. The host was tested and found to both express MmeI endonuclease activity and to in vivo modify the recombinant expression vector such that it was protected against MmeI endonuclease activity in vitro.

This finding that the single polypeptide encoding the MmeI endonuclease also provided in vivo protection against MmeI is in contrast to the previously published information on MmeI (Tucholski, Gene 223:293–302 (1998)). Specifically, this reference taught that the MmeI endonuclease polypeptide did not provide protection against MmeI endonuclease cleavage. This reference reported a separate methyltransferase of 48 kD as required to modify the MmeI site on both strands and thus block cleavage by the MmeI endonuclease. Specifically, the reference teaches that the MmeI endonuclease polypeptide modifies the adenine in the top strand of the recognition sequence only, 5'-TCCRAC-3' and that such modified DNA is cut by the MmeI endonuclease. The DNA fragment of the present invention encodes the MmeI endonuclease gene, which when grown alone in an *E. coli* host renders the vector containing the MmeI endonuclease resistant to cleavage by the purified MmeI endonuclease. Further, the MmeI endonuclease produced from this fragment does not cleave a DNA fragment modified at the adenine of the top strand, 5'-TCCRAC-3' when no modification of the opposite, or bottom strand is present. This is in contrast to the teaching of the Tucholski reference. Also, the MmeI endonuclease of this application does cleave a DNA fragment in which the adenine residue in the bottom strand is modified 5'-GTYGGA-3' in contrast to the teaching of the Tucholski reference. When both the top strand and the bottom strand are modified at the adenine residues, the MmeI endonuclease does not cleave the DNA. No second methyltransferase gene, such as reported in the Tucholski reference, was found adjacent to the MmeI endonuclease gene. There is an open reading frame immediately 3' to the MmeI endonuclease gene which would encode a protein of approximately the reported size of such a second methyltransferase activity (48 kD). However, this potential polypeptide does not have the amino acid motifs found in methyltransferases, nor did it provide protection against MmeI endonuclease when cloned in *E. coli*. While the Tulchoski reference taught the necessity of a second methyltransferase polypeptide to provide protection against MmeI endonuclease activity for the host cell, it is demonstrated in the present application that the DNA fragment encoding the MmeI endonuclease polypeptide is sufficient to provide such protection. Additionally, the eleven DNA fragments described herein which encode amino acid sequences similar to MmeI are not flanked by any recognizable DNA methyltransferase genes. This indicates that these polypeptides are also likely to provide both protection for the host DNA and endonuclease activity against unmodified DNA substrates on their own, without having a second methyltransferase as part of the restriction modification system. This contrasts with other type II restriction modification systems.

The same group (Tucholski, Gene 223: 293–302 (1998), and Anna Podhajska, personal communication) had previously reported an amino acid sequence of eight residues for a single internal CnBr digestion fragment (sequence GRGRGVGV (SEQ ID NO:50)). PCR based on this sequence was attempted yet failed repeatedly. This sequence was found to be unrelated to MmeI once the actual MmeI amino acid sequence was determined in accordance with the present invention. Therefore correct internal amino acid sequences determination, which enabled the cloning of the MmeI gene, depended on the novel purification method described in this application for the production of sufficiently pure MmeI in large enough quantity to determine cyanogen bromide internal fragment amino acid sequences, as performed in this Application.

In Example II we obtained MmeI by culturing a transformed host carrying the MmeI gene, such as *E. coli* ER2683 carrying pTBMmeI.1 and recovering the endonuclease from the cells. A sample of *E. coli* ER2683 carrying pTBMmeI.1 (NEB#1457) has been deposited under the terms and conditions of the Budapest Treaty with the American Type Culture Collection (ATCC) on Jul. 3, 2002 and bears the Patent Accession No. PTA-4521.

For recovering the enzyme of the present invention *E. coli* carrying pTBMmeI.1 (NEB#1457) may be grown using any suitable technique. For example, *E. coli* carrying pTBMmeI.1 may be grown in Luria broth media containing 100 μg/ml ampicillin and incubated aerobically at 37° C. with aeration. Cells in the late logarithmic stage of growth are induced by adding 0.3 mM IPTG, grown for an additional 4 hours, collected by centrifugation and either disrupted immediately or stored frozen at −70° C.

The MmeI enzyme can be isolated from *E. coli* carrying pTBMmeI.1 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing MmeI. The MmeI endonuclease, along with its corresponding intrinsic methylase activity, is then purified from the cell-free extract by ion-exchange chromatography, affinity chromatography, molecular sieve chromatography, or a combination of these methods to produce the endonuclease of the present invention.

The present invention also relates to methods for identifying additional DNA fragments, each of which encodes a polypeptide having significant amino acid sequence similarity to the MmeI polypeptide. The polypeptides encoded by these DNA fragments are predicted to perform similar functions to MmeI. Specifically, they are predicted to possess the dual enzymatic functions of cleaving DNA in a specific manner at a relatively far distance from the specific recognition sequence and also modifying their recognition sequences to protect the host DNA from cleavage by their endonuclease activity. Once the amino acid sequence of the MmeI endonuclease was determined as described in this application, sequences deposited in databases can be compared to this MmeI sequence to find those few sequences that are highly significantly similar to MmeI. This method is similar to that of U.S. Pat. No. 6,383,770 (Roberts, et al.), except that here we are searching for similarity to the MmeI endonuclease sequence, rather than searching for sequences that match a database of methyltransferase or endonuclease proteins and then examining any unidentified open reading frames next to potential methyltransferase open reading frames. Prior to identifying the MmeI amino acid sequence, the DNA sequences coding for proteins related to MmeI had not been included in the database of restriction and methyltransferase gene sequences utilized by Roberts, et al., supra since these sequences had not been linked to any known endonuclease function. The method disclosed herein of identifying potential MmeI-like endonucleases is thus more specific than the method of U.S. Pat. No. 6,383,770 (Roberts, et al.).

Similarity searching of the MmeI sequence against sequences available in databases, such as GENBANK, is accomplished using a program such as BLAST (Altschul, et al. Nucleic Acids Res. 25:3389–3402 (1997)). A sequence with an expectation value (E) score of less than $E=e^{-10}$ is considered a potential candidate endonuclease. Sequences that give expectation values that are much lower, such as less than $E=e^{-30}$ is to be considered as highly likely to be endonucleases like MmeI. Such candidate MmeI-like peptides are further examined to see if they conform to the domain architecture that MmeI exhibits. A true candidate will contain an endonuclease fold motif, usually of the form (D/E)X8–X12(D/E)XK in the amino-terminal portion of the peptide, (Aravind et al. Nucleic Acid Res. 28:3417–3432 (2000)). A true candidate will contain methyltransferase motifs in the middle portion of the peptide similar to gamma class N6-methyl adenine methyltransferases, and sequences similar to the carboxyl portion of MmeI in the carboxyl portion of the candidate peptide. Such a BLAST search performed on Jun. 12, 2003 returned the following sequences as highly significantly similar to MmeI:

prove possible to express functional endonucleases by repairing the mutations that have inactivated these genes. Several of the MmeI homologs, such as #7 (SEQ ID NO:14)(Deinococcus radiodurans DR2267) and #8 (SEQ ID NO:13)(Deinococcus radiodurans DR0119.1) have disruptions in the open reading frames. DR2267 has a stop codon, TAG, which prematurely terminates the open reading frame, in a position where MmeI has a glutamate amino acid coded for by the codon GAG. By changing this TAG stop codon to GAG it may be possible to reactivate this potential endonuclease gene. DR0119.1 is also disrupted, in that it has a frameshift that disrupts open reading frame. The MmeI sequence may be used as a guide to direct where to repair this frameshift by maximizing the similarity of the DR0119.1 sequence to the MmeI sequence. This may well restore DR0119.1 endonuclease activity.

An alternative way to generate potential new endonucleases is to take advantage of their similar domain structure by performing domain swapping. One may be able to swap the amino terminal domain of an MmeI-like peptide, for the amino terminal domain in the MmeI protein, for example by swapping the sequence of the potential new gene up to the first methyltransferase motif (motif X, "Gly Ala His Tyr Thr Ser" into MmeI to replace this portion of MmeI up to the same sequence. This approach may be particularly useful when only a partial sequence is available or a potential gene has lost function due to multiple mutations. This approach will create a chimeric protein that potentially has endonuclease activity and cleaves at a distance away from the recognition sequence, like MmeI, but that recognizes a novel DNA sequence. One may also find sequences in the data-

| GENBANK ACCESSION NO. | DESCRIPTION | SCORE | E VALUE | SEQ ID NO: |
|---|---|---|---|---|
| 1. gi\|15794682\|ref\|NP_284504.1\| | hypothetical protein [Neisseri | 643 | 0.0 | 6 |
| 2. gi\|9945797\|gb\|AAG03371.1\| | GcrY [Corynebacterium striatum | 604 | e-171 | 8 |
| 3. gi\|16077744\|ref\|NP_388558.1\| | similar to hypothetical protei | 564 | e-159 | 7 |
| 4. gi\|28373198\|ref\|NP_783835.1\| | putative YeeA protein [Lactoba . . . | 531 | e-149 | 3 |
| 5. gi\|23110638\|gb\|ZP_00096791.1\| | hypothetical protein [Novosph . . . | 426 | e-118 | 10 |
| 6. gi\|27450519\|gb\|AAO14619.1\|AF465251_62 | unknown [Lactobacillus . . . | 217 | 9e-55 | 4 |
| 7. gi\|15807258\|ref\|NP_295988.1\| | DNA modification methyltransfe . . . | 213 | 1e-53 | 14 |
| 8. gi\|15807788\|ref\|NP_285443.1\| | conserved hypothetical protein . . . | 164 | 7e-39 | 13 |
| 9. gi\|21231551\|ref\|NP_637468.1\| | conserved hypothetical protein . . . | 142 | 2e-32 | N/A |
| 10. gi\|20803963\|emb\|CAD31540.1\| | PUTATIVE DNA METHYLASE PROTEIN . . . | 134 | 7e-30 | 11 |
| 11. gi\|23451826\|gb\|AAN32874.1\|AF461726_1 | unknown [Pseudomonas f . . . | 98 | 6e-19 | 9 |
| 12. gi\|16125079\|ref\|NP_419643.1\| | conserved hypothetical protein . . . | 92 | 3e-17 | 12 |
| 13. gi\|10954534\|ref\|NP_044172.1\| | M. jannaschii predicted coding . . . | 76 | 2e-12 | N/A |

Most of these proteins are labeled as hypothetical or putative in their database entries. A number of these appear to be full-length polypeptides, such as sequence #2 above: GcrY. Such candidates can be expressed as described in Roberts to identify the expected endonuclease activity. Some endonuclease genes may be inactive in the particular strain used for sequencing (Lin, et al. Proc. Natl. Acad. Sci. USA 98:2740–2745 (2001)). In such a circumstance it may bases that are highly similar to MmeI but that are partial. For example, sequence #11 (SEQ ID NO:9) above (Pseudomonas fluorescens) is from a small fragment of DNA sequence in the database. To obtain a functional endonuclease like MmeI from this sequence one can use inverse PCR or other techniques to obtain DNA sequence adjacent to the fragment reported, then use that sequence to obtain an intact endonuclease gene.

Once a sequence is identified the potential endonuclease can be expressed and characterized as described in Roberts, et al. supra. Here, however, there is no separate methyltransferase gene to express along with the endonuclease. Once such a potential endonuclease is cloned and expressed in a suitable host, such as in *E. coli*, a cell free extract is prepared and analyzed to detect any endonuclease activity. Such an endonuclease assay must include the SAM cofactor required by these endonucleases. Once specific DNA cleavage activity is found the recognition sequence and cleavage site may be determined by standard methods. (Schildkraut, (1984) In Genet. Eng. (N Y) Vol 6. (Setlow J. K., Hollaender, A. Ed.). pp 117–140. Plenum Press, New York. "Screening for and characterizing restriction endonucleases.")

The enzymes so identified can be isolated from *E. coli* cells carrying the DNA fragment in a suitable vector by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing the enzyme. The endonuclease, along with its corresponding intrinsic methylase activity, is then purified from the cell-free extract by ion-exchange chromatography, affinity chromatography, molecular sieve chromatography, or a combination of these methods to produce the endonuclease of the present invention.

These DNA fragments, as well as any other fragments with such similarity to MmeI that may be deposited in the databases in the future, are predicted to encode polypeptides that are similar to MmeI, in that the polypeptides encoded act as both restriction endonuclease and methyltransferase. These polypeptides may, like MmeI, cleave DNA at a similarly far distance from the recognition sequence, in the range of about 18 to 20 nucleotides or more, which character is unique and useful in certain molecular biology technologies.

An example of such an enzyme identified by this process is CstMI (see U.S. application Ser. No. 10/616,689, filed concurrently herewith). CstMI was identified as a potential endonuclease because of its highly significant amino acid sequence similarity to MmeI. CstMI is encoded by sequence #2 above (SEQ ID NO:8), which gave highly significant Expectation value of $e^{-171}$ when compared to MmeI by BLAST. CstMI recognizes the 6 base pair asymmetric sequence 5'-AAGGAG-3' and cleaves the DNA in the same manner as MmeI: it cleaves the phosphodiester bond between the 20th and 21st residues 3' to this recognition sequence on this DNA strand, and between the 18th and 19th residues 5' to the recognition sequence on the complement strand 5'-CTCCTT-3' to produce a 2 base 3' extension.

The present invention is further illustrated by the following Examples. These Examples are provided to aid in the understanding of the invention and are not construed as a limitation thereof.

The references cited above and below are herein incorporated by reference.

EXAMPLE I

Purification of MmeI Endonuclease

A single colony of *Methylophilus methylotrophus* (NEB#1190) was grown for 24 hrs in 1 liter of medium M (0.08 μM $CuSO_4$, 0.448 μM $MnSO_4$, 0.348 μM $ZnSO_4$, 6.0 μM $FeCl_3$, 18 μM $CaCO_3$, 1.6 mM $MgSO_4$, 9.0 μM $NaH_2PO_4$, 10.9 mM $K_2HPO_4$, 13.6 mM $(NH_4)_2SO_4$) for 24 hours. This culture was used to inoculate 100 liters of medium M. The cells were grown aerobically at 37° C., overnight, until stationary. Five 100-liter fermentations were required to harvest 752 grams of wet cell pellet.

750 gram of *M. methylotrophus* cell pellet was suspended in 2.25 liters of Buffer A (20 mM Tris-HCl (pH 8.0), 50 mM NaCl, 1.0 mM DTT, 0.1 mM EDTA, 5% Gycerol) and passed through a Gaulin homogenizer at ~12,000 psig. The lysate was centrifuged at −13,000×G for 40 minutes and the supernatant collected.

The supernatant solution was applied to a 500 ml Heparin Hyper-D column (BioSepra SA) which had been equilibrated in buffer A. A 1.0 L wash of buffer A was applied, then a 2 L gradient of NaCl from 0.05 M to 1 M in buffer A was applied and fractions were collected. Fractions were assayed for MmeI endonuclease activity by incubating with 1 μg Lambda DNA (NEB) in 50 μl NEBuffer 1, supplemented with 32 μM S-adenosyl-L-methionine (SAM) for 15 minutes at 37° C. MmeI activity eluted at 0.3 M to 0.4 M NaCl.

The Heparin Hyper-D column fractions containing the Mme I activity were pooled, diluted to 50 mM NaCl with buffer A (without NaCl) and applied to a 105 ml Source15 Q column (Amersham Biotech) which had been equilibrated with buffer A. A 210 ml wash with buffer A was applied followed by a 1.0 L gradient of NaCl from 0.05 M to 0.7 M in buffer A. Fractions were collected and assayed from Mme I endonuclease activity. The Mme I activity was found in the unbound fraction.

The Source15 Q pool was loaded onto a 22 ml AF-Heparin-TSK column (TosoHaas) which had been equilibrated with buffer A. A wash of 44 ml buffer A was applied, followed by a linear gradient of NaCl from 0.05 M to 1.0 M in buffer A. Fractions were collected and assayed from Mme I endonuclease activity. The Mme I activity eluted between 0.26 M and 0.29 M NaCl. The fractions containing activity were pooled and dialyzed against buffer B (20 mM $NaPO_4$ (pH 7.0), 50 mM NaCl, 1.0 mM DTT, 0.1 mM EDTA, 5% Glycerol).

The dialyzed AF-Heparin-TSK pool was loaded onto a 6 ml Resource15 S column (Amersham Biotech) which had been equilibrated with buffer B. A wash of 12 ml buffer B was applied, followed by a linear gradient of NaCl from 0.05 M to 1.0 M in buffer B. Fractions were collected and assayed for Mme I endonuclease activity. Mme I activity eluted between 0.14 M and 0.17 M NaCl.

This pool was applied to a 2 liter Superdex 75 sizing column (Amersham Biotech) which had been equilibrated with buffer C (20 mM Tris-HCl, pH 8.0, 500 mM NaCl, 1.0 mM DTT, 0.1 mM EDTA, 5% Glycerol). Fractions were collected between 500 and 1500 ml elution with buffer C, then assayed by Mme endonuclease assay and polyacrylamide gel electrophoresis on 4–20% gradient gel, followed by protein staining with Coomassie Brilliant Blue dye. Fractions eluting between 775 and 825 ml corresponded to Mme I activity and a protein band of 105 kDa. These fractions were pooled and dialyzed against buffer D (20 mM $NaPO_4$ (pH 7.0), 50 mM NaCl, 1 mM DTT, 5% Glycerol).

The dialyzed sizing pool was applied to a 16 ml Ceramic HTP column (BioRad) which had been equilibrated with buffer D. A 32 ml wash with buffer D was followed by a linear gradient from 0.02 M to 1.0 M $NaPO_4$ in buffer D. Fractions were collected and assayed by Mme endonuclease assay and polyacrylamide gel electrophoresis on a 4–20% gradient gel, followed by protein staining with Coomassie Brilliant Blue dye. Mme I eluted between 0.26 M and 0.3 M $NaPO_4$. A portion of several fractions containing a single homogeneous protein band of 105 kDa were used for protein sequencing. The rest of the purified MmeI fractions were pooled (6 ml @0.36 mg/ml) and dialyzed against storage buffer (10 mM Tris (pH 7.9), 50 mM KCl, 1 mM DTT, 0.1 mM EDTA, 50% glycerol). The purified MmeI enzyme was stored at −20° C.

Activity Determination:

Samples from 1–4 μl were added to 50 μl substrate solution consisting of 1×NEBuffer 1, 32 μM S-adenosyl-L-methionine, and 1 μg DNA (lambda, PhiX174 or pUC19 DNAs). Reactions were incubated for 15 minutes at 37°, received 20 μl stop solution and were analyzed by electrophoresis on a 1% agarose gel.

Optimized Endonuclease Activity

Following purification of MmeI from *M. methylotrophus*, experiments were performed to determine the optimal reaction conditions for DNA cleavage. Endonuclease activity was found to be significantly enhanced by the presence of potassium in the reaction buffer. Reactions were performed at 4° C. to 37° C. and from 5 to 60 minutes with no appreciable change in the amount of DNA cleavage. Enzyme concentrations at or near stoichiometric equivalence to DNA sites were required for maximal cleavage. Large excess of enzyme blocked cleavage. These findings were used to reassess the activity of MmeI and to define a workable endonuclease unit.

Unit Definition

One unit of MmeI is defined as the amount of MmeI required to completely cleave 1 μg of PhiX174 DNA in 15 minutes at 37° C. in NEBuffer 4 (20 mM Tris-acetate, 10 mM magnesium acetate, 50 mM potassium acetate, 1 mM dithiothreitol (pH7.9 at 25° C.)) supplemented with 80 μM S-adenosyl-L-methionine (SAM).

EXAMPLE II

Cloning the MmeI Endonuclease

1. DNA purification: Total genomic DNA of *Methylophilus methylotrophus* was prepared. 5 grams of cell paste was suspended in 20 ml of 25% sucrose, 0.05 M Tris-HCl pH 8.0, to which was added 10 ml of 0.25 M EDTA, pH 8.0. Then 6 ml of lysozyme solution (10 mg/ml lysozyme in 0.25 M Tris-HCl, pH 8.0) was added and the cell suspension was incubated at 4° C. for 16 hours. 25 ml of Lytic mix (1% Triton-X100, 0.05 M Tris, 62 mM EDTA, pH 8.0) and 5 ml of 10% SDS was then added and the solution incubated at 37° C. for 5 minutes. The solution was extracted with one volume of equilibrated phenol:chloroform:isoamyl alcohol (50:48:2, v/v/v) and the aqueous phase was recovered and extracted with one volume of chloroform:isoamyl alcohol (24:1, v/v) two times. The aqueous solution was then dialysed against four changes of 2 L of 10 mM Tris, 1 mM EDTA, pH 8.0. The dialysed DNA solution was digested with RNase (100 μg/ml) at 37° C. for 1 hour. The DNA was precipitated by the addition of ¹/₁₀th volume 5 M NaCl and 0.55 volumes of 2-propanol and spooled on a glass rod. The DNA was briefly rinsed in 70% ethanol, briefly air dried and dissolved in 20 ml TE (10 mM Tris, 1 mM EDTA, pH 8.0) to a concentration of approximately 500 μg/ml and stored at 4° C.

2. The MmeI endonuclease was purified to homogeneity as described in Example I above.

3. Amino acid sequences of the MmeI endonuclease were obtained for the amino terminus and for several internal cyanogen bromide digestion products of the MmeI polypeptide. The MmeI restriction endonuclease, prepared as described in Example I above, was subjected to electrophoresis and electroblotted according to the procedure of Matsudaira (Matsudaira. J. Biol. Chem. 262:10035–10038, 1987)), with modifications as previously described (Looney, et al. Gene 80:193–208 (1989)). The membrane was stained with Coomassie blue R250 and the protein band of approximately 105 kD was excised and subjected to sequential degradation on an ABI Procise 494 Protein/Peptide Sequencer with gas-phase delivery (Waite-Rees, et al. J. Bacteriol. 173:5207–5219 (1991)). The amino acid sequence of the first 14 amino terminal residues obtained was the following:

ALSWNEIRRKAIEF (SEQ ID NO:15).

An additional sample of the MmeI endonuclease, 20 μg in 20 μl, was treated with 2 μg of cyanogen bromide (Sigma) dissolved in 200 μl of 88% distilled formic acid for 24 hours in the dark at room temperature. This reaction mixture was evaporated to dryness and resuspended in 20 μl of loading buffer (1.5M Tris-HCl, pH 8.5, 12% glycerol, 4% SDS, 0.05% Serva Blue G, 0.05% Phenol Red) at 100° C. for 5 minutes. This sample was subjected to electrophoresis on a Tris-Tricine 10 to 20% polyacrylamide gradient gel (Invitrogen) for three hours and then transferred to a polyvinylidene difluoride (PVDF) membrane (Problott, Applied Biosystems Inc.) using 10 mM CAPS buffer (10 mM 3-[cyclohexylamino]-1propanesulfonic acid, 10% methanol, 0.05% SDS, 0.005% dithiotheritiol, adjusted to pH 11.0 with NaOH) for 18 hours at 200 volts in a tank electroblotter (TE52, Hoeffer). The membrane was stained with Coomassie blue R-250 and major bands of 25 kilodaltons (kD), 14 kD, 7.5 kD and 6 kD were observed, as well as smaller bands. These stained protein bands were excised from the membrane and each subjected to sequential degradation. The fragments other than the amino terminal fragment are derived from internal cleavage by cyanogen bromide at methionine residues from within the protein and thus should be preceded by a methionine. The first 29 residues of the 25 kD peptide corresponded to (M)KISDEFGNYFARIPLK-STXXIXEXNALQ (SEQ ID NO:16). Residues 20, 21, 23 and 25, labeled X, were not identified. The first 40 amino acid residues obtained from the 14 kD fragment were: (M)DAKKRRNLGAHYTSEANILKLI KPLLLDELWV-VFXKVKN (SEQ ID NO:17). Residue 36 was not determined. The first 25 residues of the 7.5 kD peptide corresponded to (M)KSRGKDLDKAYDQALDYFSGIAER (SEQ ID NO:18). The 6 kD fragment was found to contain a mixture of three sequences.

4. Amplification of a portion of the MmeI endonuclease: The peptide sequence data from the amino terminus, 25 kD, 14 kD and 7.5 kD peptides was used to construct a series of degenerate PCR primers corresponding to the codons for the amino acid residues. The order of the internal peptide fragments was unknown, so both forward (sense strand) and reverse (antisense strand) primers were made for these fragments. The primers were:

25 kD fragment: residues DEFGNYFA (SEQ ID NO:19)

```
Forward:
1)   5'-GARTTYGGNAAYTAYTTYGC-3'      (SEQ ID NO:20)

Reverse:
2)   5'-AARTARTTNCCRAAYTCRTC-3'      (SEQ ID NO:21)
```

14 kD fragment: residues MDAKKR (SEQ ID NO:22)

```
Forward A:
3)   5'-ATGGAYGCNAARAARCG-3'            (SEQ ID NO:23)

Forward B:
4)   5'-ATGGAYGCNAARAARAG-3'            (SEQ ID NO:24)

Reverse:
5)   5'-CGNCGYTTYTTNGCRTCCAT-3'         (SEQ ID NO:25)
```

7.5 kD fragment: residues DKAYDQA (SEQ ID NO:26)

```
Forward:
6)   5'-GAYAARGCNTAYGAYCARGC-3'         (SEQ ID NO:27)

Reverse:
7)   5'-GCYTGRTCRTANGCYTTRTC-3'         (SEQ ID NO:28)
``` where
Y=T,C
R=A,G
H=A,T,C
S=G,C
N=A,C,G,T

Primers 1 and 2 are derived from the MmeI 25 kD CNBr peptide and were prepared to prime on the sense strand (1) or the antisense strand (2) of the gene. Primers 3 through 5 are derived from the 14 kD CNBr peptide and were prepared to prime on the sense strand (3 and 4) or the antisense strand (5) of the gene, with 3 and 4 differing in the codon usage for the arginine residue. Primers 6 and 7 are derived from the 7.5 kD CNBr peptide and were prepared to prime on the sense strand (6) or the antisense strand (7) of the gene.

PCR amplification reactions were performed using the primer combinations of 1 with 5, 1 with 7, 3 with 2, 3 with 7, 4 with 2, 4 with 7, 6 with 2 and 6 with 7. A portion of the MmeI gene was amplified in a PCR reaction by combining:
80 μl 10×Thermopol buffer (NEB)
50 μl 4 mM DNTP solution (NEB)
4 μl MmeI genomic DNA (500 μg/ml stock)
16 μl 100 mM $MgSO_4$
586 μl $dH_2O$
16 μl (32 units) Vent® exo-DNA polymerase (NEB).

This master mix was divided into 8 aliquots of 90 μl, to which was added 5 μl forward primer (10 μM stock) and 5 μl reverse primer (10 μM stock). The cycling parameters were 95° C. for 3 minutes for one cycle, then 95° C. for 30 seconds, 46° C. for 30 seconds, 72° C. for 2 minutes, for 25 cycles.

The amplification reactions were electrophoresed on a 1% agarose gel and analyzed. Major DNA amplification products of 450 base pairs (bp) (primers 2 with 4), 650 bp (primers 5 with 6) and 1100 bp (primers 2 with 6) were obtained. These fragment sizes are consistent with the 7.5 kD CnBr fragment being located nearest the amino end of the protein and approximately 650 bp away from the 14 kD CnBr fragment, with the 14 kD fragment between the 7.5 kD and the 25 kD fragment and adjacent to the 25 kD fragment. The amplified DNA fragments were gel purified and sequenced using the primers that were used for the amplification. A translation of the DNA sequence obtained matched the amino acid sequence derived from the purified MmeI endonuclease, indicating that a portion of the MmeI endonuclease gene DNA sequence had been successfully obtained.

5. Determining the DNA sequence for the entire MmeI gene and adjacent DNA: The inverse PCR technique was used to extend the DNA sequence from both sides of the 1060 bp of the MmeI gene obtained above. To accomplish this a series of primers matching the MmeI gene DNA sequence and oriented for inverse PCR were designed and synthesized. MmeI genomic DNA was cut with a number of restriction endonucleases and ligated at low concentration to generate circular DNA templates.

A. MmeI genomic DNA was digested with ten different restriction endonucleases and then circularly ligated to obtain DNA templates to amplify using the inverse PCR technique. The restriction enzymes used were:

| | |
|---|---|
| BspHI | (T/CATGA) |
| EcoRI | (G/AATTC) |
| HindIII | (A/AGCTT) |
| HinP1I | (G/CGC) |
| MspI | (C/CGG) |
| NlaIII | (CATG/) |
| PstI | (CTGCA/G) |
| SacI | (GAGCT/C) |
| SphI | (GCATG/C) |
| XbaI | (T/CTAGA) |

Restriction enzyme digests were performed by combining:
5 μl 10×NEBuffer recommended for the enzyme (varied with enzyme)
2 μM. methyloptrophus genomic DNA (1 μg)
43 μl $dH_2O$
1 μl (10–20 units) restriction enzyme.

The reactions were incubated for 1 hour at 37° C. The restriction endonuclease was inactivated by heating the reaction to 65° C. (80° C. for PstI) for 20 minutes. The digested DNA was then ligated into circular fragments by adding 50 μl 10×T4 DNA ligase buffer, 400 μl $dH_2O$ and 3 μl concentrated T4 DNA ligase (6000 units, New England Biolabs, Inc.) and incubating at 16° C. for 16 hours. The ligated DNA was then extracted with phenol and chloroform, precipitated with 2-propanol and resuspended in 100 μl TE buffer.

B. Amplification of DNA adjacent to the 1060 bp fragment of the MmeI endonuclease gene: Two pairs of PCR primers were designed, one near each end of the 1060 bp sequence obtained from direct PCR with degenerate primers. The primer sequences were:

```
primer IP 1:
5'-GTTGGATCCCGCACAGATTGCTCAGG-3'        (SEQ ID NO:29)

primer IP 2:
5'-GTTGGATCCTACGTTAATCTGAATAAGATG-3'    (SEQ ID NO:30)

primer IP 3:
5'-GTTGGATCCTGTTAATCTGAAACGCTGG-3'      (SEQ ID NO:31)

primer IP 4:
5'-GTTGGATCCTTATACCAAAATGTGAGGTC-3'     (SEQ ID NO:32)
```

Inverse PCR reactions were performed on the 10 circularized templates produced above with the primer pairs of IP 1 with IP 2, IP 3 with IP 4, and IP 1 with IP 3. The amplification reactions were assembled by combining:
80 µl 10×Thermopol buffer (NEB)
50 µl 4 mM DNTP solution (NEB)
40 µl IP primer (forward)
40 µl IP primer (reverse)
16 µl 100 mM MgSO₄
534 µl dH₂O
16 µl (32 units) Vent® exo-DNA polymerase (NEB).

The master mix was aliquoted into ten tubes of 76 µl, to which was added 4 µl of the appropriate digested, circularly ligated template. The cycling parameters were 95° C. for 3 minutes for one cycle, then 95° C. for 30 seconds, 56° C. for 30 seconds, 72° C. for 3 minutes, for 25 cycles. Amplification products were analyzed by agarose gel electrophoresis.

For primers IP 1 and IP 2 with the SphI template and the NlaIII template a product of approximately 825 bp was obtained. For primers IP 3 and IP 4 with the BspHI template a product of approximately 800 bp was obtained. For primers IP 1 and IP 3 with the EcoRI template a product of approximately 1500 bp was obtained. These amplified DNA fragments were gel purified, sequenced and assembled with that previously obtained. The assembled sequence did not contain the entire MmeI endonuclease open reading frame. The assembled sequence was used to direct synthesis of a second group of inverse PCR primer pairs. The sequences of these primers were:

```
primer IP 5:
5'-TTCAGAAATACGAGCGATGC-3'      (SEQ ID NO:33)

primer IP 6:
5'-GTCAAGCCATAAACACCATC-3'      (SEQ ID NO:34)

primer IP 7:
5'-GAGGGTCAGAAAGGAAGCTG-3'      (SEQ ID NO:35)

primer IP 8:
5'-GTCCAACTAACCCTTTATGG-3'      (SEQ ID NO:36)
```

Inverse PCR amplification reactions were performed as above. Using primers IP 5 and IP 6, products were obtained from the NlaIII template (approximately 450 bp) and the MspI template (approximately 725 bp), but not from the other circular ligation templates. Using primers IP 7 and IP 8, products were obtained from the EcoRI template (approximately 500 bp), the SphI template (approximately 825 bp) and the BspHI template (approximately 750 bp). These DNA fragments were sequenced and the sequence was assembled with that previously obtained. The assembled sequence did not yet contain the entire MmeI endonuclease open reading frame, so another round of primer synthesis and inverse PCR was performed. Additional DNA templates were generated as above, but using the restriction enzymes ApoI (R/AATTY), AseI (AT/TAAT), BsaHI (GR/CGYC), MfeI (C/AATTG), SspI (AAT/ATT) and EcoRV (GAT/ATC) to digest *M. methylotrophus* genomic DNA. The sequences of this third round of primers were:

```
primer IP 9:
5'-TTCCTAGTGCTGAACCTTTG-3'      (SEQ ID NO:37)

primer IP 10:
5'-GTTGCGTTACTTGAAATGAC-3'      (SEQ ID NO:38)

primer IP 11:
5'-CCAAAATGGAACTTGTTTCG-3'      (SEQ ID NO:39)

primer IP 12:
5'-GTGAGTGCGCCCTGAATTAG-3'      (SEQ ID NO:40)
```

Inverse PCR amplification reactions were performed as above. Using primers IP 9 and IP 10, products were obtained from the NlaIII template (approximately 425 bp), the MfeI template (approximately 750 bp), the ApoI template (approximately 800 bp) and the MspI template (approximately 2100 bp). Using primers IP 11 and IP 12, products were obtained from the SphI template (approximately 875 bp), the BspHI template (approximately 925 bp) and the EcoRI template (approximately 950 bp). These DNA fragments were sequenced and the sequence was assembled with the sequences previously obtained. Further sequencing was performed on the IP 9, IP10 MspI 2100 bp product using three additional primers:

```
primer S1:
5'-GCTTCATTTCATCCTCTGTGC-3'     (SEQ ID NO:41)

primer S2:
5'-TAACCGCCAAAATTAATCGTG-3'     (SEQ ID NO:42)

primer S3:
5'-CCACTATTCATTACAACACC-3'      (SEQ ID NO:43)
```

The final assembled sequence (FIGS. 2A–2E) contained the entire MmeI restriction gene, as well as 1640 bp of sequence preceding the gene and 1610 bp of sequence following the gene.

6. Cloning the MmeI endonuclease gene in *E. coli*: The putative MmeI endonuclease open reading frame was identified from the DNA sequence assembly obtained from sequencing the various inverse PCR amplified DNA fragments. The beginning of the open reading frame was identified on the basis of the match of the predicted amino acid sequence at the amino terminus of the open reading frame with the sequence determined from the MmeI endonuclease protein. The predicted end of the open reading frame would allow for the coding of an approximately 105 kD polypeptide, which matched the observed size of the native MmeI endonuclease. The amino acid sequence deduced from translation of this open reading frame contained conserved sequence motifs of N6mA DNA methyltransferases. However, no open reading frame containing sequence motifs conserved among DNA methyltransferases was observed adjacent to the MmeI endonuclease gene, as had been expected. It was decided to try to express the MmeI endonuclease in *E. coli* without having a second methyltransferase present to protect the *E. coli* host DNA from cleavage. Oligonucleotide primers were synthesized to specifically amplify the MmeI gene from *M. methylotrophus* genomic DNA for expression in the cloning vector pRRS (Skoglund, Gene 88:1–5 (1990)). The forward primer contained a PstI site for cloning, a stop codon in frame with the lacZ gene of the vector, a consensus *E. coli* ribosome binding site, the ATG start codon for translation (changed from the GTG used by *M. methylotrophus* to facilitate greater expression in *E. coli*) and 20 nucleotides that matched the *M. methylotrophus* DNA sequence:

5'-GTTCTGCAGTTAAGGATAACATATG-
GCTTTAAGCTGGAACGAG-3' (SEQ ID NO:44)

The reverse primer contained a BamHI site for cloning and 22 nucleotides that matched the *M. methylotrophus* DNA sequence 3' to the end of the MmeI open reading frame:

5'-GTTGGATCCGTCGACATTAAT-
TAATTTTTGCCCTTAG-3' (SEQ ID NO:45)

The MmeI gene was amplified in a PCR reaction by combining:
50 µl 10×Thermopol buffer (NEB)
30 µl 4 mM DNTP solution
12.5 µl forward primer (10 µM stock)
12.5 µl reverse primer (10 µM stock)
5 µl MmeI genomic DNA (500 µg/ml stock)
387 µl dH$_2$O
3 µl (6 units) Vent® DNA polymerase The reaction was mixed and aliquoted into 5 tubes of 80 µl each. MgSO$_4$ was added (100 mM stock) to bring the final concentration of Mg++ions to 2 mM, 3 mM, 4 mM, 5 mM and 6 mM respectively. The cycling parameters were 95° C. for 30 seconds, 60° C. for 30 seconds, 72° C. for 3 minutes, for 24 cycles. The reactions were analyzed by gel electrophoresis and the 3 mM through 6 mM Mg++reactions were found to contain a DNA band of the desired size of 2.8 kb. These reactions were pooled and the 2.8 kb band was gel purified. The 2.8 kb amplified MmeI gene fragment was digested with BamHI and PstI endonucleases (NEB) in the following reaction conditions:
15 µl 10×BamHI reaction buffer (NEB)
1.5 µl BSA (NEB)
50 µl MmeI gene 2.8 kb amplified DNA fragment
80 µl dH$_2$O
5 µl BamHI endonuclease (100 units)
5 µl PstI endonuclease (100 units)

The reaction was mixed and incubated for 1 hour at 37° C. The small fragments cleaved off the ends of the 2.8 kb DNA fragment were removed, along with the endonucleases, by purification on a Qiagen QiaPrep spin column according to the manufacturer's instructions.

The cleaved MmeI gene DNA fragment was ligated to the pRRS vector as follows: 10 µl of the digested, purified 2.8 kb MmeI fragment was combined with 5 µl pRRS vector previously cleaved with BamHI and PstI and purified, 5 µl dH$_2$O, 20 µl 2×QuickLigase Buffer (NEB), the reaction was mixed, and 2 µl of QuickLigase was added. The reaction was incubated at room temperature for 5 minutes. 5 µl of the ligation reaction was transformed into 50 µl chemical competent E. coli ER2683 cells and the cells were plated on L-broth plates containing 100 µg/ml ampicillin and incubated at 37° C. overnight. Approximately 200 transformants were obtained and 18 representatives were analyzed as follows: plasmid from each colony was isolated by miniprep procedures and digested with AlwNI and NdeI endonucleases to determine if they contained the correct size insert. 2 of the 18 transformants had the correct size insert of approximately 2800 bp. Both clones were tested to see if they produced MmeI endonuclease activity. The clones were grown overnight at 37° C. in 500 mL L-broth containing 100 µg/ml ampicillin. The cells were harvested by centrifugation, suspended in 10 mL sonication buffer (20 mM Tris-HCl, 1 mM DTT, 0.1 mM EDTA, pH7.5) and broken by sonication. The crude lysate was cleared by centrifugation and the supernatant was recovered. The lysate was assayed for endonuclease activity by serial dilution of the lysate in 1×reaction buffer NEBuffer 1 (New England Biolabs) containing 20 µg/ml lambda DNA substrate and supplemented with SAM at 100 µM final concentration. The reactions were incubated for 1 hour at 37° C. The reaction products were analyzed by agarose gel electrophoresis on a 1% agarose gel in 1× TBE buffer. One of the two clones had MmeI endonuclease activity. This active clone was designated strain NEB1457 and was used for subsequent production of MmeI. The plasmid construct expressing MmeI activity in this clone was designated pTBMmeI.1.

EXAMPLE III

The MmeI Endonuclease Provides In Vivo Protection Against MmeI Cleavage

The plasmid pTBMmeI.1 was purified from NEB1457 using the Qiagen miniprep protocol. This plasmid has two MmeI sites in the vector backbone, and one site within the MmeI gene. The plasmid was digested with MmeI to test whether this DNA was resistant to MmeI endonuclease activity, which would indicate that the single MmeI gene was able to methylate DNA in vivo to protect the host DNA against its endonuclease activity. To test this the following were combined:
10 µl pTBMmeI.1 miniprep DNA
15 µl 10×NEBuffer 4
15 µl SAM (1 mM stock solution)
110 µl dH20
1 µl MmeI endonuclease (15 units)

Figure 4:
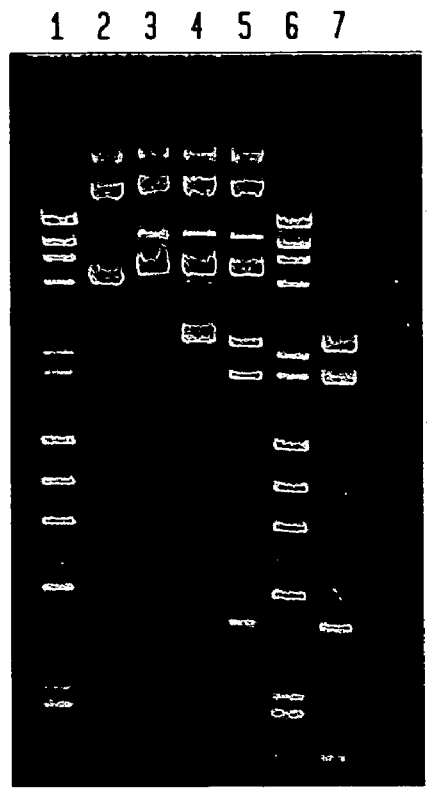

The reaction was mixed and split in thirds. To one third was added 0.5 µl dH$_2$O, to the second was added 0.5 µl pRRS vector and to the third was added 0.5 µl PhiX174 DNA as a positive control. The pTBMmeI.1 was not cleaved by the MmeI endonuclease activity, while the Phix174 and pRRS DNAs in the same reaction were cleaved, indicating that the three MmeI sites in the pTBMmeI.1 DNA are resistant to MmeI endonuclease activity (FIG. 4).

EXAMPLE IV

MmeI Endonuclease Sensitivity to Methylation

The prior literature reports that MmeI endonuclease methylates just one strand of its recognition sequence, and that this hemi-methylation does not block subsequent cleavage of the DNA by the endonuclease (Tucholski, Gene 223 (1998) 293–302). To test this a set of four oligonucleotides were synthesized so that a DNA substrate could be formed that was either unmethylated (oligo 1+oligo 2), methylated in the top strand only (oligo 3+oligo 2), methylated in the bottom strand only (oligo 1+oligo 4), or methylated on both strands (oligo 3+oligo 4). The oligos synthesized were:

```
Oligo 1:
5'-FAM-GTTTGAAGACTCCGACGCGATGGCCAGCGATCGGCGCCTCAGCTTTTG-3'        (SEQ ID NO:46)

Oligo 2:
5'-FAM-CAAAAGCTGAGGCGCCGATCGCTGGCCATCGCGTCGGAGTCTTCAAAC-3'        (SEQ ID NO:47)

Oligo 3:
5'-FAM-GTTTGAAGACTCCG(6mA)CGCGATGGCCAGCGATCGGCGCCTCAGCTTTTG-3'    (SEQ ID NO:48)
```

-continued

Oligo 4:
5'-FAM-CAAAAGCTGAGGCGCCGATCGCTGGCCATCGCGTCGG(6mA)GTCTTCAAAC-3'    (SEQ ID NO:49)

Figure 5:
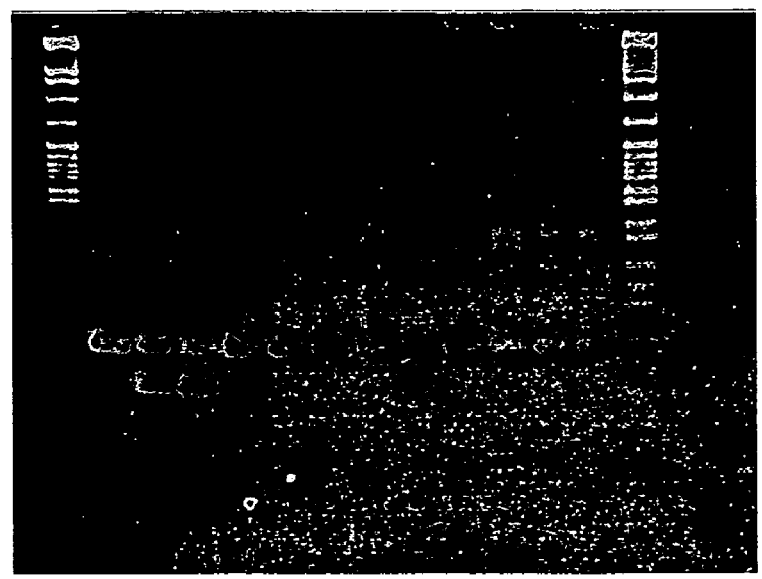

(Other nucleotides outside the MmeI recognition sequence were also methylated for other studies, but since MmeI does not have any sequence specifity for these nucleotides this does affect MmeI activity and these other methylations are omitted here for clarity.) Duplex DNA was formed by mixing 100 µl top strand oligo (14 µM stock) with 100 µl bottom strand oligo (14 µM stock), heating to 85° C. and cooling slowly to 30° C. over a time of 20 minutes. MmeI was then used to cleave the oligo pairs in a 30 µl reaction of 1×NEBuffer4, 2.5 µM oligo, 100 µM SAM and 2.5 units MmeI. As a control, restriction endonuclease Hpy188I was also used to cleave the oligo DNA. The Hpy188I recognition sequence overlaps the first 5 nucleotides of the MmeI recognition sequence in this DNA, 5'-TCNGA-3' and is blocked by methylation at the adenine in either strand of the DNA. MmeI was found to cleave unmethylated DNA as expected. In contrast to previous teaching (Tucholski, Gene 223:293–302 (1998)) MmeI did not cleave the hemi-methylated DNA when the top strand only was methylated: 5'-TCCG(N6mA)C-3'. When the bottom strand only was methylated MmeI did cleave the DNA. When both strands were methylated MmeI did not cleave the DNA. (FIG. 5) This finding is consistent with both the observed ability of the single MmeI enzyme to protect host DNA against cleavage in vivo and the observation that MmeI methylates only the top strand of its recognition sequence. We confirmed the report that MmeI enzyme methylates only the top strand of its recognition sequence by methylating the oligo pairs above with tritium labeled $H^3$-SAM, washing away the unincorporated SAM and counting the radioactivity in the DNA. Both the unmethylated oligo DNA and the top unmethylated, bottom methylated DNAs had greater than 10-fold more counts than background, while the bottom unmethylated, top methylated DNA and the DNA with both strands methylated had counts near background (FIG. 6). These findings indicate that MmeI is a novel type of restriction modification system which does not require a separate methyltransferase enzyme to modify the host DNA to provide protection against the activity of the endonuclease, as is the case for the type IIG (also called type IV) enzymes such as Eco57I.

EXAMPLE V

DNA Sequencing and Analysis

DNA Sequencing: DNA sequencing was performed on double-stranded templates on an ABI 373 or ABI 377 automated sequencer. Amplified DNA fragments and individual clones were sequenced with primers synthesized as above or from universal primers located in the vector.

Computer analyses: Computer analyses of the DNA sequences obtained were performed with the Genetics Computer Group programs (Deverenx, et al., Nucleic Acids Res. 12:387–395 (1984)) and database similarity searches were performed via the internet at the National Center for Biotechnology Information site (http://www.ncbi.nlm.nih.gov/BLAST/) using the BLASTX and the BLASTP algorithms (Altschul, et al., J. Mol. Biol 215:403–410 (1990) and Gish, et al., Nature Genet. 3:266–722 (1993)).

What is claimed is:

1. Isolated DNA coding for the MmeI restriction enzyme, wherein the isolated DNA is obtainable from *Methylophilus methylotrophus*.

2. A recombinant DNA vector comprising a vector into which a DNA segment coding for the MmeI restriction enzyme has been inserted.

3. Isolated DNA coding for the MmeI endonuclease and methyltransferase, wherein the isolated DNA is obtainable from ATCC Accession No. PTA-4521.

4. A cloning vector that comprises the isolated DNA of claim 3.

5. A host cell transformed by the vector of claim 2 or 4.

6. A method of producing recombinant MmeI restriction endonuclease and MmeI methylase comprising culturing a host cell transformed with the vector of claims 2 or 4 under conditions suitable for expression of said endonuclease and methylase.

* * * * *

UNITED STATES PATENT AND TRADEMARK OFFICE
CERTIFICATE OF CORRECTION

PATENT NO.       : 7,115,407 B2
APPLICATION NO.  : 10/616624
DATED            : October 3, 2006
INVENTOR(S)      : Tanya Bhatia et al.

It is certified that error appears in the above-identified patent and that said Letters Patent is hereby corrected as shown below:

(column 7, line 30) change 5'-TCCRAC-3' to 5'-TCCR<u>A</u>C-3'

(column 7 line 38) change 5'-TCCRAC-3' to 5'-TCCR<u>A</u>C-3'

(column 7, line 43) change 5'-GTYGGA-3' to 5'-GTYGG<u>A</u>-3'

Signed and Sealed this
Tenth Day of May, 2011

David J. Kappos
*Director of the United States Patent and Trademark Office*

SEQUENCE LISTING

<160> NUMBER OF SEQ ID NOS: 50

<210> SEQ ID NO 1
<211> LENGTH: 6010
<212> TYPE: DNA
<213> ORGANISM: Methylophilus methylotrophus
<220> FEATURE:
<221> NAME/KEY: misc_feature
<222> LOCATION: (800)..(800)
<223> OTHER INFORMATION: n is a, c, g, or t

<400> SEQUENCE: 1
gaattccaga taggtagtcc tttggtactt ccatcccaac cagtgtcacg ttccgcgcca      60
aaccaatcgg ttaaagtgta agaaagtctt gcactgaagt agctgtagga caaaccgaag     120
ttaacctctg tggtatccca gcgaccacct ttaggtgttt gacggaagcc tgctgcgtca     180
cctgccaagt tatatttctt ccatgaacca cctgggtaca ggtagctgat caaaccagca     240
gtccaaccca agccttcaat agcaggaata gttccgttat acccaccata aatatcaatt     300
tcggcagttg catcagggaa ggtatttggt gtcacgtttg aaccccatgc accgacataa     360
aagccgctgt catgagtaat atcaataccg ccttgaacgg caggtttgtg ccagttttgt     420
gaaataccac gagcatagta atctgaaaca aatccaacgt ttgcagtagc agcccaggct     480
gatttttctt ctttagcctc ttcagctgcg tatgaaactt gggcaaaaga taatgtgctt     540

-continued

| | | |
|---|---|---|
| aacactgctg tgagcaatat agattgacgc attatgagtc ctctctctgt gaaatctttg | 600 |
| attaagttgt tgtaaacgag aatgaaacaa caaccacaaa gcaaagcacg tgccaaacta | 660 |
| taaataacat tataatcaat tatttaaaat atatttataa tctaaaatat taaattaatt | 720 |
| atttaataaa ctgttttta ttgatttaac tctaaaacat atgggtgcaa ccacccttt | 780 |
| tactcactga taatgctaan atagccaaca aaggagcctt caccatgctg atttcaaatg | 840 |
| aaaaaattca ggaattatct ttaaaaatca aacaactaat cgaatcaagc cccatttcag | 900 |
| agctaaataa caacttgcat gcactaattc agggcgcact caccaaaatg gaacttgttt | 960 |
| cgcgtgaaga attcgatatc caatctgcat tattagcgcg cacgcaagag caattaaaac | 1020 |
| gtcttgaaga aaaatcagc cagcttgaag aagggcaggc atccagaaag taaaaattaa | 1080 |
| tttacaattg ttagcattcc attattgagg agtgcgctat gagtctggcg gtgttataca | 1140 |
| gtcgcgcgtt aagcggcatg gaggcgccag aagtggtggt agaagtccac ttggcgaatg | 1200 |
| gactacccag ctttaccatt gttgaaacat attgaaactt taagccttag cattttttca | 1260 |
| aatatacaaa tgccccaagc tggtgcatta agaagaatgt aacaactccc tgcagactag | 1320 |
| gaataacttc atgatttaac gaacatccct gagtttcaaa gtcgaatctt ctcgtgttgc | 1380 |
| aaatttctac agcttccttt ctgaccctct tgcaccaaat tgcactatgg cgctaataaa | 1440 |
| tcttctgcta tccaataatg tccaactaac cctttatgga ctcttaaaaa agatttaata | 1500 |
| aatgattaag atgaattcaa ggaatttgat gcctggaaat atggcaaaag caaaaaggca | 1560 |
| gcccagtgct gacttttttg ttttaacatt ggcccatata tccaatttca aataatttaa | 1620 |
| aaattatcgg gagctaatct gtggctttaa gctggaacga gataagaaga aaagctattg | 1680 |
| agttttctaa aagatgggaa gacgcctcag atgaaaacag tcaagccaaa cccttttaa | 1740 |
| tagattttt cgaagttttt ggaataacta ataagagagt tgcaacattt gagcatgctg | 1800 |
| tgaaaaagtt cgccaaggcc cataaggaac aatctcgagg attcgtagat ttgttttggc | 1860 |
| ctggcattct tcttattgaa atgaaaagca gaggtaaaga cctcgacaaa gcgtatgacc | 1920 |
| aggcacttga ttactttct ggcattgcag aaagagactt acccagatac gttttagttt | 1980 |
| gcgacttcca gcgtttcaga ttaacagacc taataacaaa agagtcagtt gaatttcttt | 2040 |
| taaaggactt ataccaaaat gtgaggtctt ttggttttat agctggttat caaactcaag | 2100 |
| taatcaagcc acaagaccct attaatatta aggcggctga acggatgggt aagcttcatg | 2160 |
| acaccctgaa gttggttgga tatgagggac acgctttaga actttatcta gtgcgtttac | 2220 |
| ttttttgctt attcgcagaa gacacaacta tttttgagaa aagtttattc caagaatata | 2280 |
| tcgagacaaa gacgctagag gacggcagtg accttgcaca tcatatcaat acactttttt | 2340 |
| atgttctcaa taccccagaa caaaaagat taaagaatct agacgaacac cttgctgcat | 2400 |
| ttccatatat caatggaaaa ctttcgagg agccacttcc gccagctcag tttgataaag | 2460 |
| caatgagaga ggcattgctt gacttgtgct cattagattg gagcaggatt tcaccagcaa | 2520 |
| tatttggaag tttattccaa agcattatgg atgctaaaaa gaagaaat cttggggcac | 2580 |
| actacaccag cgaagcaaat attctcaagt taatcaagcc attgtttctt gacgagctct | 2640 |
| gggtagagtt cgagaaagtt aaaaataata aaaataaatt actagcgttc cacaaaaaac | 2700 |
| taagaggact tacattttc gaccctgcat gcggttgcgg aaattttctt gtaatcacat | 2760 |
| accgagaact aagactttta gaaattgaag tgttaagagg attgcataga ggtggtcaac | 2820 |
| aagtttggga tattgagcat cttattcaga ttaacgtaga ccagtttttt ggtatcgaaa | 2880 |
| tagaggagtt tcccgcacag attgctcagg ttgctctctg gcttacagac caccaaatga | 2940 |

-continued

```
atatgaaaat ttcagatgag tttggaaact actttgcccg tatcccacta aaatctactc    3000
ctcacatttt gaatgctaat gctttacaga ttgattggaa cgatgtttta gaggctaaaa    3060
aatgttgctt catattagga aatcctccat ttgttggtaa aagtaaacaa acaccgggac    3120
aaaaagcgga tttactatct gtttttggaa atcttaaatc cgcttcagac ttagacctag    3180
ttgctgcttg gtatcccaaa gcagcacatt acattcaaac aaatgcaaac atacgctgtg    3240
catttgtctc aacgaatagt attactcaag gtgagcaagt atcgttgctt tggccgcttc    3300
tgctctcatt aggcataaaa ataaactttg ctcacagaac tttcagctgg acaaatgagg    3360
cgtcaggagt agcggcggtt cactgcgtaa ttatcggatt tgggttgaag gattcagatg    3420
aaaaaataat ctatgagtat gaaagtatta atggagaacc attagctatt aaggcaaaaa    3480
atattaatcc atatttgaga gacggggtgg atgtgattgc ctgcaagcgt cagcagccaa    3540
tctcaaaatt accaagcatg cgttatggca acaaaccaac agatgatgga aatttccctat   3600 ttactgacga agaaaaaaac caatttatta caaatgagcc atcttccgaa aaatacttca    3660
gacggtttgt gggcggggat gagttcataa acaatacaag tcgatggtgt ttatggcttg    3720
acggtgctga catttcagaa atacgagcga tgcctttggt cttggctagg ataaaaaaag    3780
tccaagaatt cagattaaaa agctcggcca aaccaactcg acaaagtgct tcgacaccaa    3840
tgaagttctt ttatatatct cagccggata cggactatct gttgatacct gaaacatcat    3900
ctgaaaacag acaatttatt ccaattggtt ttgttgatag aaatgtcatt tcaagtaacg    3960
caacgtatca tattcctagt gctgaacctt tgatatttgg cctgctttca tcgaccatgc    4020
acaactgctg gatgagaaat gtaggaggaa ggttagaaag tcgttataga tattctgcca    4080
gcctggttta caacacgttt ccatggattc aacccaacga aaaacaatcg aaagcgatag    4140
aagaagctgc atttgcgatt ttaaaagcta gaagcaatta ccaaacgaa agtttagctg    4200 gtttatacga cccaaaaaca atgcctagtg agcttcttaa agcacatcaa aaacttgata    4260
aggctgtgga ttctgtctat ggatttaaag gaccaaacac agaaattgct cgaatagctt    4320
ttttgtttga aacataccaa aagatgactt cactcttacc accagaaaaa gaattaaga    4380 aatctaaggg caaaaattaa ttaatgtatt taacattaaa ccaccctgat ttatttcgaa    4440
tagttcaaat gcttccatgt ggactaatcg ccttcaatca tattaaaaaa ccgacgctag    4500
taataaaaac ttccaaagag gccatattaa ccgccaaaat taatcgtgaa tttaaaatat    4560
atctttatca aaccacatcg gcttgtgttc tagtaagtgc atttttgac gattctgata     4620 gtccactatt cattacaaca ccaattgttc gagatgacca acactcctta gacttgttaa    4680
gatttttaat caacaatgat tttacgattt gcttctttga tgaactgaac cgagaatttc    4740
tttccgttaa cgcaactggt aatttagtct ctatctttga gagcattcac ttgatgccac    4800
tgccgagccc agaggaagcc cacaatgcat gaatgaagc ggaattttgg ttcagtttac     4860
gctcagctgc tgatgatgaa tcatctatcc aggtttcttt attggataat ctatttcctg    4920
acgattttgt aatttatgac ctatcctcaa acaaaaacga tatgacatca ttggttagag    4980
aaactaaacc aggatactat caggaagcag atattgcaaa gttactaaca agagctttta    5040
gtttggaaag catttatcag aatccagtga aacaagcga ttcaaaagag ttggcagacg      5100
ttgtggtatt cggccaaaag gaaatttta taattcaagc taaagatagt gaaaacaatc     5160
agaaacaagt tttagaggtt tcgttagaca agaaatgcgc aaagtcttca agaaactttt    5220
ctgaagcttt ggcacaactc accgacacta tcttaacaat atccaataca ccaatagttg    5280
```

```
atgttcgggt tggtaagaaa aaatgcactc tgaactttga gggaaagcag cttattggta    5340
tcgtcgttgt taaagagctt tttaatgata tttacgataa atacagtcaa aaagtttttg    5400
agcatgtaga gttgtctaaa gcacccattg tcttctttga ctatccagaa tttgcaagaa    5460
tgacatttca ttgtaattct gaggaattat tactttatgc tttgcatagg atatttagtt    5520
ctgcaataga aaatggaatg tataaacgat tgagatttac tcaacctatc ataactgatg    5580
gtcatgacag ctacttcagg atacaaaaca ggccccattc tgatgaggcc tatttaattt    5640
gcacagagga tgaaatgaag ctctcaaata agtttaaaga ctaaatttat attttcctca    5700
gtatcttaaa aacaatattc attaaattgg aaagcccgca atgattgttg cagtatcaat    5760
gcgggcatca gtatccagct cttgcaatac acggaagtat caagaagcga atcaggattc    5820
taaccatacc tttttaattg caacaatcta atttccataa catgtgtagc tacatcgaaa    5880
aaaagacctc gaagaggttg caagagcgtc cagctcgcgg catcaaaaga ccctagtctt    5940
ttgacaaggg ggagccaaaa aactgaggtg gaggagcttg ccgacgaagc caggaagccc    6000
cagcgtccgg                                                           6010
```

<210> SEQ ID NO 2
<211> LENGTH: 919
<212> TYPE: PRT
<213> ORGANISM: Methylophilus methylotrophus

<400> SEQUENCE: 2

```
Met Ala Leu Ser Trp Asn Glu Ile Arg Arg Lys Ala Ile Glu Phe Ser
1               5                   10                  15

Lys Arg Trp Glu Asp Ala Ser Asp Glu Asn Ser Gln Ala Lys Pro Phe
            20                  25                  30

Leu Ile Asp Phe Phe Glu Val Phe Gly Ile Thr Asn Lys Arg Val Ala
        35                  40                  45

Thr Phe Glu His Ala Val Lys Lys Phe Ala Lys Ala His Lys Glu Gln
    50                  55                  60

Ser Arg Gly Phe Val Asp Leu Phe Trp Pro Gly Ile Leu Leu Ile Glu
65                  70                  75                  80

Met Lys Ser Arg Gly Lys Asp Leu Asp Lys Ala Tyr Asp Gln Ala Leu
                85                  90                  95

Asp Tyr Phe Ser Gly Ile Ala Glu Arg Asp Leu Pro Arg Tyr Val Leu
            100                 105                 110

Val Cys Asp Phe Gln Arg Phe Arg Leu Thr Asp Leu Ile Thr Lys Glu
        115                 120                 125

Ser Val Glu Phe Leu Leu Lys Asp Leu Tyr Gln Asn Val Arg Ser Phe
    130                 135                 140

Gly Phe Ile Ala Gly Tyr Gln Thr Gln Val Ile Lys Pro Gln Asp Pro
145                 150                 155                 160

Ile Asn Ile Lys Ala Ala Glu Arg Met Gly Lys Leu His Asp Thr Leu
                165                 170                 175

Lys Leu Val Gly Tyr Glu Gly His Ala Leu Glu Leu Tyr Leu Val Arg
            180                 185                 190

Leu Leu Phe Cys Leu Phe Ala Glu Asp Thr Thr Ile Phe Glu Lys Ser
        195                 200                 205

Leu Phe Gln Glu Tyr Ile Glu Thr Lys Thr Leu Glu Asp Gly Ser Asp
    210                 215                 220

Leu Ala His His Ile Asn Thr Leu Phe Tyr Val Leu Asn Thr Pro Glu
225                 230                 235                 240
```

-continued

```
Gln Lys Arg Leu Lys Asn Leu Asp Glu His Leu Ala Ala Phe Pro Tyr
            245                 250                 255

Ile Asn Gly Lys Leu Phe Glu Glu Pro Leu Pro Ala Gln Phe Asp
            260                 265                 270

Lys Ala Met Arg Glu Ala Leu Leu Asp Leu Cys Ser Leu Asp Trp Ser
            275                 280                 285

Arg Ile Ser Pro Ala Ile Phe Gly Ser Leu Phe Gln Ser Ile Met Asp
    290                 295                 300

Ala Lys Lys Arg Arg Asn Leu Gly Ala His Tyr Thr Ser Glu Ala Asn
305                 310                 315                 320

Ile Leu Lys Leu Ile Lys Pro Leu Phe Leu Asp Glu Leu Trp Val Glu
                325                 330                 335

Phe Glu Lys Val Lys Asn Asn Lys Asn Lys Leu Leu Ala Phe His Lys
                340                 345                 350

Lys Leu Arg Gly Leu Thr Phe Phe Asp Pro Ala Cys Gly Cys Gly Asn
                355                 360                 365

Phe Leu Val Ile Thr Tyr Arg Glu Leu Arg Leu Leu Glu Ile Glu Val
    370                 375                 380

Leu Arg Gly Leu His Arg Gly Gly Gln Gln Val Leu Asp Ile Glu His
385                 390                 395                 400

Leu Ile Gln Ile Asn Val Asp Gln Phe Phe Gly Ile Glu Ile Glu Glu
                405                 410                 415

Phe Pro Ala Gln Ile Ala Gln Val Ala Leu Trp Leu Thr Asp His Gln
                420                 425                 430

Met Asn Met Lys Ile Ser Asp Glu Phe Gly Asn Tyr Phe Ala Arg Ile
            435                 440                 445

Pro Leu Lys Ser Thr Pro His Ile Leu Asn Ala Asn Ala Leu Gln Ile
    450                 455                 460

Asp Trp Asn Asp Val Leu Glu Ala Lys Lys Cys Cys Phe Ile Leu Gly
465                 470                 475                 480

Asn Pro Pro Phe Val Gly Lys Ser Lys Gln Thr Pro Gly Gln Lys Ala
                485                 490                 495

Asp Leu Leu Ser Val Phe Gly Asn Leu Lys Ser Ala Ser Asp Leu Asp
            500                 505                 510

Leu Val Ala Ala Trp Tyr Pro Lys Ala Ala His Tyr Ile Gln Thr Asn
            515                 520                 525

Ala Asn Ile Arg Cys Ala Phe Val Ser Thr Asn Ser Ile Thr Gln Gly
530                 535                 540

Glu Gln Val Ser Leu Leu Trp Pro Leu Leu Leu Ser Leu Gly Ile Lys
545                 550                 555                 560

Ile Asn Phe Ala His Arg Thr Phe Ser Trp Thr Asn Glu Ala Ser Gly
                565                 570                 575

Val Ala Ala Val His Cys Val Ile Ile Gly Phe Gly Leu Lys Asp Ser
                580                 585                 590

Asp Glu Lys Ile Ile Tyr Glu Tyr Glu Ser Ile Asn Gly Glu Pro Leu
            595                 600                 605

Ala Ile Lys Ala Lys Asn Ile Asn Pro Tyr Leu Arg Asp Gly Val Asp
        610                 615                 620

Val Ile Ala Cys Lys Arg Gln Gln Pro Ile Ser Lys Leu Pro Ser Met
625                 630                 635                 640

Arg Tyr Gly Asn Lys Pro Thr Asp Asp Gly Asn Phe Leu Phe Thr Asp
            645                 650                 655

Glu Glu Lys Asn Gln Phe Ile Thr Asn Glu Pro Ser Ser Glu Lys Tyr
```

-continued

```
                            660                 665                 670
        Phe Arg Arg Phe Val Gly Gly Asp Glu Phe Ile Asn Asn Thr Ser Arg
                        675                 680                 685
        Trp Cys Leu Trp Leu Asp Gly Ala Asp Ile Ser Glu Ile Arg Ala Met
                        690                 695                 700
        Pro Leu Val Leu Ala Arg Ile Lys Lys Val Gln Glu Phe Arg Leu Lys
        705                 710                 715                 720
        Ser Ser Ala Lys Pro Thr Arg Gln Ser Ala Ser Thr Pro Met Lys Phe
                        725                 730                 735
        Phe Tyr Ile Ser Gln Pro Asp Thr Asp Tyr Leu Leu Ile Pro Glu Thr
                        740                 745                 750
        Ser Ser Glu Asn Arg Gln Phe Ile Pro Ile Gly Phe Val Asp Arg Asn
                        755                 760                 765
        Val Ile Ser Ser Asn Ala Thr Tyr His Ile Pro Ser Ala Glu Pro Leu
                        770                 775                 780
        Ile Phe Gly Leu Leu Ser Ser Thr Met His Asn Cys Trp Met Arg Asn
        785                 790                 795                 800
        Val Gly Gly Arg Leu Glu Ser Arg Tyr Arg Tyr Ser Ala Ser Leu Val
                        805                 810                 815
        Tyr Asn Thr Phe Pro Trp Ile Gln Pro Asn Glu Lys Gln Ser Lys Ala
                        820                 825                 830
        Ile Glu Glu Ala Ala Phe Ala Ile Leu Lys Ala Arg Ser Asn Tyr Pro
        835                 840                 845
        Asn Glu Ser Leu Ala Gly Leu Tyr Asp Pro Lys Thr Met Pro Ser Glu
        850                 855                 860
        Leu Leu Lys Ala His Gln Lys Leu Asp Lys Ala Val Asp Ser Val Tyr
        865                 870                 875                 880
        Gly Phe Lys Gly Pro Asn Thr Glu Ile Ala Arg Ile Ala Phe Leu Phe
                        885                 890                 895
        Glu Thr Tyr Gln Lys Met Thr Ser Leu Leu Pro Glu Lys Glu Ile
                        900                 905                 910
        Lys Lys Ser Lys Gly Lys Asn
                        915

<210> SEQ ID NO 3
<211> LENGTH: 932
<212> TYPE: PRT
<213> ORGANISM: unknown
<220> FEATURE:
<223> OTHER INFORMATION: GenBank No. gi[28]373198f[]_783835.1

<400> SEQUENCE: 3

Met Pro Thr Arg Gln Gln Ala Arg Glu Phe Val Lys Thr Trp Ser
        1               5                   10                  15

Ser Asp Lys Lys Gly Arg Glu Asp Ala Asp Arg Gln Thr Phe Trp Asn
                        20                  25                  30

Asp Leu Leu Gln Arg Val Tyr Gly Ile Asp Asn Tyr Tyr Asp Tyr Ile
                        35                  40                  45

Thr Tyr Glu Lys Asp Val Gln Val Lys Ala Asp Gly Lys Val Thr Thr
                50                  55                  60

Arg Arg Ile Asp Gly Tyr Ile Pro Ser Thr Lys Ile Met Val Glu Met
        65                  70                  75                  80

Lys Gly Lys Asn Ile Lys Asp Leu Ser Lys Pro Ile Thr Gln Ser Gly
                        85                  90                  95

Gly Asp Glu Leu Thr Pro Phe Glu Gln Ala Lys Arg Tyr Ala Asn Phe
```

-continued

```
            100                 105                 110
Leu Pro Asn Ser Glu Gln Pro Arg Trp Ile Leu Val Ser Asn Phe Asn
        115                 120                 125
Glu Ile Asp Ile His Asp Met Glu Arg Pro Leu Asp Glu Pro Lys Val
    130                 135                 140
Ile Lys Leu Glu Asp Leu Pro Lys Lys Val Lys Ser Leu Glu Phe Met
145                 150                 155                 160
Val Asp Ala Asn Gln Gln Val Ile Asp Glu Lys Gln Leu Ser Val
                165                 170                 175
Asp Ala Gly Asn Leu Val Ala Lys Ile Tyr Asn Glu Leu Thr Asn Ala
            180                 185                 190
Tyr Ala Ala Gly Arg Gly Ile Asp Val Asn Glu Pro Arg Ile Gln Arg
        195                 200                 205
Ser Leu Asn Met Leu Ile Val Arg Leu Val Phe Leu Leu Tyr Ala Asp
    210                 215                 220
Asp Ser Asn Leu Phe Gly Lys Glu Asp Ile Phe Gln Ala Phe Ile Glu
225                 230                 235                 240
Arg Arg Glu Pro Arg Asp Ile Arg Arg Asp Leu Ser Glu Leu Phe Lys
                245                 250                 255
Val Leu Asp Gln Pro Glu Gln Arg Asp Pro Tyr Leu Asp Asp Glu
            260                 265                 270
Phe Asn Gln Phe Ala Tyr Val Asn Gly Gly Met Phe Ser Asp Glu Asn
        275                 280                 285
Val Ile Ile Pro Gln Phe Thr Asp Glu Leu Lys Arg Leu Ile Val Glu
    290                 295                 300
Asp Ala Gly Arg Gly Phe Asp Trp Ser Gly Ile Ser Pro Thr Ile Phe
305                 310                 315                 320
Gly Ala Val Phe Glu Ser Thr Leu Asn Pro Glu Thr Arg Arg Ser Gly
                325                 330                 335
Gly Met His Tyr Thr Ser Ile Glu Asn Ile His Lys Val Ile Asp Pro
            340                 345                 350
Leu Phe Leu Asn Asp Leu His Asp Glu Phe Asp Lys Ile Gln Asn Met
        355                 360                 365
Gly Asn Arg Arg Gln Arg Val Thr Arg Ala Lys Ala Phe Arg Asp Lys
    370                 375                 380
Leu Gly Lys Leu Lys Phe Phe Asp Pro Ala Cys Gly Ser Gly Asn Phe
385                 390                 395                 400
Leu Thr Glu Thr Tyr Leu Ser Leu Arg Lys Met Glu Asn Glu Cys Leu
                405                 410                 415
Arg Ile Ile Val Gly Asn Gln Gly Ala Leu Ala Leu Thr Asp Glu Ser
            420                 425                 430
Glu Pro Lys Val Lys Ile Gln Asn Phe Tyr Gly Ile Glu Ile Asn Asp
        435                 440                 445
Phe Ala Val Ser Val Ala Arg Thr Ala Met Trp Ile Ala Glu Ser Gln
    450                 455                 460
Met Trp Glu Gln Thr Lys Asp Ile Thr Phe Ala Asn Lys Asp Phe Leu
465                 470                 475                 480
Pro Leu Asp Ser Asn Asp Ser Ile Tyr Glu Gly Asn Ala Leu Arg Met
                485                 490                 495
Asp Trp Asn Asp Ile Val Lys Pro Tyr Glu Leu Asp Tyr Ile Met Gly
            500                 505                 510
Asn Pro Pro Phe Val Gly Tyr Ser Leu Gln Thr Lys Glu Gln Lys Gln
        515                 520                 525
```

-continued

```
Asp Ile Lys Gln Glu Phe Phe Lys Tyr Thr Asp Lys Tyr Gly Lys Phe
    530                 535                 540

Asp Tyr Val Ser Gly Trp Tyr Ile Lys Gly Ala Lys Tyr Ile Gln Asn
545                 550                 555                 560

Ser Thr Ile Lys Val Gly Phe Val Ser Thr Asp Ser Ile Ile Gln Gly
                565                 570                 575

Glu Gln Ala Pro Glu Ile Trp Lys Val Leu Phe Asn Asp Phe His Ile
                580                 585                 590

Phe Ile Asn Tyr Gly Tyr Arg Ser Phe Glu Trp Asn Asn Glu Ala Ala
            595                 600                 605

Asn Lys Ala Lys Val Asp Val Ile Val Gly Phe Ser Thr Lys Glu
        610                 615                 620

Asp Lys Asn Pro Thr Ile Tyr Asp Glu Gln Lys Ile Ile Ser Ala Lys
625                 630                 635                 640

His Ile Asn Gln Tyr Met Tyr Asp Ser Asp Asn Ile Phe Ile Asp Thr
                645                 650                 655

Thr Arg Lys Tyr Ile Glu Ala Met Pro Lys Met Lys Thr Gly Asn Arg
                660                 665                 670

Pro Ala Asp Gly Gly Ala Leu Ile Leu Ser Pro Lys Glu Ala Lys Glu
            675                 680                 685

Leu Val Asn Glu Glu Pro Gln Ser Lys Gln Phe Ile Lys Lys Leu Thr
    690                 695                 700

Gly Ser Lys Glu Phe Ile Thr Gly Lys Tyr Arg Tyr Cys Leu Trp Leu
705                 710                 715                 720

Val Asn Val Thr Pro Lys Gln Leu Arg Ser Met Pro Leu Val Leu Lys
                725                 730                 735

Arg Val Glu Gln Cys Lys Glu Asn Arg Leu Ser Gly Ala Pro Asp Arg
                740                 745                 750

Gln Lys Leu Ala Ala Thr Pro His Leu Phe Arg Glu Gln Met Asn Pro
            755                 760                 765

Asp Asn Tyr Met Ile Val Pro Leu Val Thr Gly Cys Arg Arg Lys Tyr
    770                 775                 780

Val Pro Phe Gly Tyr Leu Gly Asn Asp Ile Ile Pro Thr Asn Leu Ala
785                 790                 795                 800

Thr Ile Ile Pro Glu Ala Asp His Tyr Ala Phe Gly Val Leu Glu Ser
                805                 810                 815

Ile Val His Met Ala Trp Met Arg Val Val Ala Gly Arg Lys Gly Thr
                820                 825                 830

Ser Tyr Arg Tyr Ser Lys Asn Leu Val Tyr Thr Asn Phe Pro Trp Pro
            835                 840                 845

Val Val Asp Ile Asn Gln Lys Glu Lys Ile Thr Ile Thr Ala Gln Asp
    850                 855                 860

Ile Leu Asn Ala Arg Asn Leu Tyr Pro Asp Ser Ser Leu Ala Asp Leu
865                 870                 875                 880

Tyr Asp Pro Leu Thr Met Pro Ile Glu Leu Arg Lys Ala His Glu Ala
                885                 890                 895

Asn Asp Lys Ala Val Leu Lys Ala Tyr Gly Leu Lys Pro Ser Ala Thr
            900                 905                 910

Glu Pro Glu Ile Val Gln His Leu Phe Lys Met Tyr Glu Lys Leu Thr
    915                 920                 925

Lys Lys Asp Trp
    930
```

```
<210> SEQ ID NO 4
<211> LENGTH: 354
<212> TYPE: PRT
<213> ORGANISM: unknown
<220> FEATURE:
<223> OTHER INFORMATION: GenBank No.
      gi[27]450519β´014619.1⁼465251_62

<400> SEQUENCE: 4
```

Val Leu Phe Asn Asp Phe His Ile Phe Ile Asn Tyr Gly Tyr Arg Ser
1               5                   10                  15

Phe Glu Trp Asn Glu Ala Ala Asn Lys Ala Lys Val Asp Val Val
            20                  25                  30

Ile Val Gly Phe Ser Thr Lys Glu Asp Lys Asn Pro Thr Ile Tyr Asp
            35                  40                  45

Ser Ser Asn Ile Ser His Cys Lys Asn Ile Asn Gly Tyr Leu Phe Asp
        50                  55                  60

Gly Asn Asn Ile Phe Val Thr Asn Arg Pro Ala Pro Leu Ser Asn Val
65                  70                  75                  80

Pro Arg Met His Asn Gly Cys Lys Leu Leu Asp Gly Gly Phe Tyr Thr
                85                  90                  95

Leu Thr Ser Gln Glu Arg Lys Glu Ala Ile Ser Lys Asp Pro Tyr Ala
                100                 105                 110

Asp Lys Phe Ile Arg Pro Tyr Leu Gly Ala Lys Asn Phe Ile His Gly
            115                 120                 125

Thr Ala Arg Tyr Cys Ile Trp Leu Lys Asp Ala Asn Pro Lys Asp Ile
        130                 135                 140

His Gln Ser Pro Phe Ile Leu Asp Arg Ile Asn Lys Val Ala Glu Phe
145                 150                 155                 160

Arg Ser Gln Gln Lys Ser Lys Asp Thr Gln Lys Tyr Ala Lys Arg Pro
                165                 170                 175

Met Leu Pro Thr Arg Leu Ala Tyr Tyr Ser His Asp Glu His Thr Asp
            180                 185                 190

Met Leu Ile Val Pro Ala Thr Ser Ser Gln Arg Arg Glu Tyr Leu Pro
        195                 200                 205

Ile Gly Tyr Val Ser Glu Lys Asn Ile Val Ser Tyr Ser Leu Met Leu
        210                 215                 220

Ile Pro Asn Ala Ser Asn Phe Asn Phe Gly Ile Leu Glu Ser Lys Val
225                 230                 235                 240

His Tyr Ile Trp Leu Lys Asn Phe Cys Gly Arg Leu Lys Ser Asp Tyr
                245                 250                 255

Arg Tyr Ser Asn Thr Ile Ile Tyr Asn Asn Phe Pro Trp Pro Thr Val
            260                 265                 270

Gly Asp Lys Gln Glu Gln Asn Ile Ser Glu Thr Ala Gln Gly Ile Leu
        275                 280                 285

Asn Thr Arg Lys Leu Tyr Pro Asp Ser Ser Leu Ala Asp Leu Tyr Asp
            290                 295                 300

Pro Leu Thr Met Pro Val Glu Leu Arg Lys Ala His Glu Ala Asn Asp
305                 310                 315                 320

Lys Ala Val Leu Lys Ala Tyr Gly Leu Ser Pro Lys Ala Thr Glu Gln
                325                 330                 335

Glu Ile Val Glu His Leu Phe Lys Met Tyr Glu Lys Leu Thr Lys Gly
            340                 345                 350

Glu Arg

```
<210> SEQ ID NO 5
<211> LENGTH: 919
<212> TYPE: PRT
<213> ORGANISM: unknown
<220> FEATURE:
<223> OTHER INFORMATION: M. methylotrophus amino acid

<400> SEQUENCE: 5

Met Ala Leu Ser Trp Asn Glu Ile Arg Arg Lys Ala Ile Glu Phe Ser
1               5                   10                  15

Lys Arg Trp Glu Asp Ala Ser Asp Glu Asn Ser Gln Ala Lys Pro Phe
            20                  25                  30

Leu Ile Asp Phe Phe Glu Val Phe Gly Ile Thr Asn Lys Arg Val Ala
        35                  40                  45

Thr Phe Glu His Ala Val Lys Lys Phe Ala Lys Ala His Lys Glu Gln
    50                  55                  60

Ser Arg Gly Phe Val Asp Leu Phe Trp Pro Gly Ile Leu Leu Ile Glu
65                  70                  75                  80

Met Lys Ser Arg Gly Lys Asp Leu Asp Lys Ala Tyr Asp Gln Ala Leu
                85                  90                  95

Asp Tyr Phe Ser Gly Ile Ala Glu Arg Asp Leu Pro Arg Tyr Val Leu
            100                 105                 110

Val Cys Asp Phe Gln Arg Phe Arg Leu Thr Asp Leu Ile Thr Lys Glu
        115                 120                 125

Ser Val Glu Phe Leu Leu Lys Asp Leu Tyr Gln Asn Val Arg Ser Phe
    130                 135                 140

Gly Phe Ile Ala Gly Tyr Gln Thr Gln Val Ile Lys Pro Gln Asp Pro
145                 150                 155                 160

Ile Asn Ile Lys Ala Ala Glu Arg Met Gly Lys Leu His Asp Thr Leu
                165                 170                 175

Lys Leu Val Gly Tyr Glu Gly His Ala Leu Glu Leu Tyr Leu Val Arg
            180                 185                 190

Leu Leu Phe Cys Leu Phe Ala Glu Asp Thr Thr Ile Phe Glu Lys Ser
        195                 200                 205

Leu Phe Gln Glu Tyr Ile Glu Thr Lys Thr Leu Glu Asp Gly Ser Asp
    210                 215                 220

Leu Ala His His Ile Asn Thr Leu Phe Tyr Val Leu Asn Thr Pro Glu
225                 230                 235                 240

Gln Lys Arg Leu Lys Asn Leu Asp Glu His Leu Ala Ala Phe Pro Tyr
                245                 250                 255

Ile Asn Gly Lys Leu Phe Glu Glu Pro Leu Pro Ala Gln Phe Asp
            260                 265                 270

Lys Ala Met Arg Glu Ala Leu Leu Asp Leu Cys Ser Leu Asp Trp Ser
        275                 280                 285

Arg Ile Ser Pro Ala Ile Phe Gly Ser Leu Phe Gln Ser Ile Met Asp
    290                 295                 300

Ala Lys Lys Arg Arg Asn Leu Gly Ala His Tyr Thr Ser Glu Ala Asn
305                 310                 315                 320

Ile Leu Lys Leu Ile Lys Pro Leu Phe Leu Asp Glu Leu Trp Val Glu
                325                 330                 335

Phe Glu Lys Val Lys Asn Asn Lys Asn Lys Leu Leu Ala Phe His Lys
            340                 345                 350

Lys Leu Arg Gly Leu Thr Phe Phe Asp Pro Ala Cys Gly Cys Gly Asn
        355                 360                 365
```

-continued

```
Phe Leu Val Ile Thr Tyr Arg Glu Leu Arg Leu Leu Glu Ile Glu Val
    370                 375                 380
Leu Arg Gly Leu His Arg Gly Gly Gln Gln Val Leu Asp Ile Glu His
385                 390                 395                 400
Leu Ile Gln Ile Asn Val Asp Gln Phe Phe Gly Ile Glu Ile Glu Glu
                405                 410                 415
Phe Pro Ala Gln Ile Ala Gln Val Ala Leu Trp Leu Thr Asp His Gln
                420                 425                 430
Met Asn Met Lys Ile Ser Asp Glu Phe Gly Asn Tyr Phe Ala Arg Ile
            435                 440                 445
Pro Leu Lys Ser Thr Pro His Ile Leu Asn Ala Asn Ala Leu Gln Ile
    450                 455                 460
Asp Trp Asn Asp Val Leu Glu Ala Lys Lys Cys Cys Phe Ile Leu Gly
465                 470                 475                 480
Asn Pro Pro Phe Val Gly Lys Ser Lys Gln Thr Pro Gly Gln Lys Ala
                485                 490                 495
Asp Leu Leu Ser Val Phe Gly Asn Leu Lys Ser Ala Ser Asp Leu Asp
                500                 505                 510
Leu Val Ala Ala Trp Tyr Pro Lys Ala Ala His Tyr Ile Gln Thr Asn
            515                 520                 525
Ala Asn Ile Arg Cys Ala Phe Val Ser Thr Asn Ser Ile Thr Gln Gly
        530                 535                 540
Glu Gln Val Ser Leu Leu Trp Pro Leu Leu Leu Ser Leu Gly Ile Lys
545                 550                 555                 560
Ile Asn Phe Ala His Arg Thr Phe Ser Trp Thr Asn Glu Ala Ser Gly
                565                 570                 575
Val Ala Ala Val His Cys Val Ile Ile Gly Phe Gly Leu Lys Asp Ser
            580                 585                 590
Asp Glu Lys Ile Ile Tyr Glu Tyr Glu Ser Ile Asn Gly Glu Pro Leu
        595                 600                 605
Ala Ile Lys Ala Lys Asn Ile Asn Pro Tyr Leu Arg Asp Gly Val Asp
    610                 615                 620
Val Ile Ala Cys Lys Arg Gln Gln Pro Ile Ser Lys Leu Pro Ser Met
625                 630                 635                 640
Arg Tyr Gly Asn Lys Pro Thr Asp Asp Gly Asn Phe Leu Phe Thr Asp
                645                 650                 655
Glu Glu Lys Asn Gln Phe Ile Thr Asn Glu Pro Ser Ser Glu Lys Tyr
            660                 665                 670
Phe Arg Arg Phe Val Gly Gly Asp Glu Phe Ile Asn Asn Thr Ser Arg
        675                 680                 685
Trp Cys Leu Trp Leu Asp Gly Ala Asp Ile Ser Glu Ile Arg Ala Met
    690                 695                 700
Pro Leu Val Leu Ala Arg Ile Lys Lys Val Gln Glu Phe Arg Leu Lys
705                 710                 715                 720
Ser Ser Ala Lys Pro Thr Arg Gln Ser Ala Ser Thr Pro Met Lys Phe
                725                 730                 735
Phe Tyr Ile Ser Gln Pro Asp Thr Asp Tyr Leu Leu Ile Pro Glu Thr
            740                 745                 750
Ser Ser Glu Asn Arg Gln Phe Ile Pro Ile Gly Phe Val Asp Arg Asn
        755                 760                 765
Val Ile Ser Ser Asn Ala Thr Tyr His Ile Pro Ser Ala Glu Pro Leu
    770                 775                 780
Ile Phe Gly Leu Leu Ser Ser Thr Met His Asn Cys Trp Met Arg Asn
```

```
                785                 790                 795                 800
Val Gly Gly Arg Leu Glu Ser Arg Tyr Arg Tyr Ser Ala Ser Leu Val
                    805                 810                 815

Tyr Asn Thr Phe Pro Trp Ile Gln Pro Asn Glu Lys Gln Ser Lys Ala
                820                 825                 830

Ile Glu Glu Ala Ala Phe Ala Ile Leu Lys Ala Arg Ser Asn Tyr Pro
                    835                 840                 845

Asn Glu Ser Leu Ala Gly Leu Tyr Asp Pro Lys Thr Met Pro Ser Glu
            850                 855                 860

Leu Leu Lys Ala His Gln Lys Leu Asp Lys Ala Val Asp Ser Val Tyr
865                 870                 875                 880

Gly Phe Lys Gly Pro Asn Thr Glu Ile Ala Arg Ile Ala Phe Leu Phe
                    885                 890                 895

Glu Thr Tyr Gln Lys Met Thr Ser Leu Leu Pro Pro Glu Lys Glu Ile
                900                 905                 910

Lys Lys Ser Lys Gly Lys Asn
            915

<210> SEQ ID NO 6
<211> LENGTH: 936
<212> TYPE: PRT
<213> ORGANISM: unknown
<220> FEATURE:
<223> OTHER INFORMATION: GenBank No. gi[15]794682f|_284504.1

<400> SEQUENCE: 6

Met Lys Thr Leu Leu Gln Leu Gln Thr Ala Ala Gln Asn Phe Ala Ala
1               5                   10                  15

Tyr Tyr Lys Asp Gln Thr Asp Glu Arg Arg Glu Lys Asp Thr Phe Asn
                20                  25                  30

Glu Phe Phe Ala Ile Phe Gly Ile Asp Arg Lys Asn Val Ala His Phe
            35                  40                  45

Glu Tyr Pro Val Lys Asp Pro Ala Asp Asn Thr Gln Phe Val Asp Ile
        50                  55                  60

Phe Trp Glu Gly Ile Phe Leu Ala Glu His Lys Ser Ala Asn Lys Asn
65                  70                  75                  80

Leu Thr Lys Ala Lys Glu Gln Ala Glu Arg Tyr Leu Gln Glu Ile Gly
                85                  90                  95

Arg Thr Lys Pro Ser Ala Leu Pro Glu Tyr Tyr Ala Val Ser Asp Phe
                100                 105                 110

Ala His Phe His Leu Tyr Arg Arg Val Pro Glu Glu Gly Ala Glu Asn
            115                 120                 125

Gln Trp Gln Phe Pro Leu Glu Glu Leu Pro Glu Tyr Ile Thr Arg Gly
        130                 135                 140

Val Phe Asp Phe Met Phe Gly Ile Glu Ala Lys Val Arg Gln Ile Gln
145                 150                 155                 160

Glu Glu Ala Asn Ile Gln Ala Ala Thr Ile Gly Arg Leu His Asp
                165                 170                 175

Ala Leu Lys Glu Glu Gly Ile Tyr Glu His Glu Leu Arg Leu Phe
            180                 185                 190

Ile Thr Arg Leu Leu Phe Leu Phe Ala Asp Asp Ser Ala Val Phe
        195                 200                 205

Arg Arg Asn Tyr Leu Phe Gln Asp Phe Leu Glu Asn Cys Lys Glu Ala
        210                 215                 220

Asp Thr Leu Gly Asp Lys Leu Asn Gln Leu Phe Glu Phe Leu Asn Thr
```

-continued

```
              225                 230                 235                 240
Pro Asp Gln Lys Arg Ser Lys Thr Gln Ser Glu Lys Phe Lys Gly Phe
                    245                 250                 255
Glu Tyr Val Asn Gly Leu Phe Lys Glu Arg Leu Arg Thr Phe Asp
            260                 265                 270
Phe Thr Ala Lys Gln His Arg Ala Leu Ile Asp Cys Gly Asn Phe Asp
            275                 280                 285
Trp Arg Asn Ile Ser Pro Glu Ile Phe Gly Thr Leu Phe Gln Ser Val
        290                 295                 300
Met Asp Ala Gln Glu Arg Arg Glu Ala Gly Ala His Tyr Thr Glu Ala
305                 310                 315                 320
Ala Asn Ile Asp Lys Val Ile Asn Gly Leu Phe Leu Glu Asn Leu Arg
                    325                 330                 335
Ala Glu Phe Glu Ala Val Lys Ala Leu Lys Arg Asp Lys Ala Lys Lys
                340                 345                 350
Leu Ala Ala Phe Tyr Gln Lys Ile Gln Asn Leu Gln Phe Leu Asp Pro
            355                 360                 365
Ala Cys Gly Cys Gly Asn Phe Leu Ile Val Ala Tyr Asp Arg Ile Arg
        370                 375                 380
Ala Leu Glu Asp Asp Ile Ile Ala Glu Ala Leu Lys Asp Lys Ala Asp
385                 390                 395                 400
Gly Leu Phe Asp Ser Pro Ser Val Gln Cys Arg Leu Lys Gln Phe His
                    405                 410                 415
Gly Ile Glu Ile Asp Glu Phe Ala Val Leu Ile Ala Arg Thr Ala Met
                420                 425                 430
Trp Leu Lys Asn His Gln Cys Asn Ile Arg Thr Gln Ile Arg Phe Asp
            435                 440                 445
Gly Glu Val Ala Cys His Thr Leu Pro Leu Glu Asp Ala Ala Glu Ile
        450                 455                 460
Ile His Ala Asn Ser Leu Arg Thr Pro Trp Gln Ala Ala Asp Tyr Ile
465                 470                 475                 480
Phe Gly Asn Pro Pro Phe Ile Gly Ser Thr Tyr Gln Thr Lys Glu Gln
                    485                 490                 495
Lys Asn Asp Leu Glu Ser Ile Cys Gly His Ile Lys Gly Tyr Gly Leu
                500                 505                 510
Leu Asp Tyr Val Cys Asn Trp Tyr Val Lys Ala Ala Gly Ile Met Ala
            515                 520                 525
Gln His Pro Gln Val Gln Thr Ala Phe Val Ser Thr Asn Ser Ile Cys
        530                 535                 540
Gln Gly Gln Gln Val Glu Ile Leu Trp Gly Ser Leu Leu Asn Gln Gly
545                 550                 555                 560
Ile Glu Ile His Phe Ala His Arg Thr Phe Gln Trp Thr Ser Gln Ala
                    565                 570                 575
Ala Gly Lys Ala Ala Val His Cys Ile Ile Val Gly Phe Arg Gln Lys
                580                 585                 590
Pro Pro Met Pro Ser Glu Lys Thr Leu Tyr Asp Tyr Pro Asp Ile Lys
            595                 600                 605
Gly Glu Pro Glu Lys His Ala Val Ala Asn Ile Asn Pro Tyr Leu Ile
        610                 615                 620
Asp Ala Pro Asp Leu Ile Ile Ala Lys Arg Ser Arg Pro Ile His Cys
625                 630                 635                 640
Glu Pro Asp Met Val Asn Gly Ser Lys Pro Thr Glu Gly Gly Asn Leu
                    645                 650                 655
```

Ile Leu Ser Thr Ala Glu Lys Asp Ala Leu Ile Ala Ala Glu Pro Leu
              660                 665                 670

Ala Glu Gln Tyr Ile Arg Pro Phe Ile Gly Ala Asp Glu Phe Leu Asn
          675                 680                 685

Gly Lys Thr Arg Trp Cys Leu Trp Phe His Gly Val Ser Asp Val Lys
      690                 695                 700

Arg Asn His Asp Leu Lys Gln Met Pro Gln Val Gln Ala Arg Ile Gln
705                 710                 715                 720

Ala Val Lys Thr Met Arg Glu Ala Ser Ser Asp Lys Gln Thr Gln Lys
              725                 730                 735

Asp Ala Ala Thr Pro Trp Leu Phe Gln Lys Ile Arg Gln Pro Ser Asp
          740                 745                 750

Gly Asn Tyr Leu Ile Ile Pro Ser Val Ser Ser Glu Ser Arg Arg Phe
      755                 760                 765

Ile Pro Ile Gly Tyr Leu Ser Phe Glu Thr Val Val Ser Asn Leu Ala
      770                 775                 780

Phe Ile Leu Pro Asn Ala Thr Leu Tyr His Phe Gly Ile Leu Ser Ser
785                 790                 795                 800

Thr Met His Asn Ala Phe Met Arg Thr Val Ala Gly Arg Leu Lys Ser
              805                 810                 815

Asp Tyr Arg Tyr Ser Asn Thr Val Val Tyr Asn Asn Phe Pro Phe Pro
          820                 825                 830

Glu Ser Cys Arg Leu Pro Ser Glu Asn Asp Arg Pro Asp Pro Leu Arg
      835                 840                 845

Ala Ala Val Glu Ala Ala Gln Thr Val Leu Asp Ala Arg Gly Gln
      850                 855                 860

Tyr Arg Arg Glu Ala Gln Glu Ala Gly Leu Pro Glu Pro Thr Leu Ala
865                 870                 875                 880

Glu Leu Tyr Ala Pro Asp Ala Gly Tyr Thr Ala Leu Asp Lys Ala His
              885                 890                 895

Ala Thr Leu Asp Lys Ala Val Asp Lys Ala Tyr Gly Tyr Lys Thr Gly
          900                 905                 910

Lys Asn Thr Asp Asp Glu Ala Glu Arg Val Ala Phe Leu Phe Glu Leu
      915                 920                 925

Tyr Arg Lys Ala Ala Ala Ile Ala
      930                 935

<210> SEQ ID NO 7
<211> LENGTH: 879
<212> TYPE: PRT
<213> ORGANISM: unknown
<220> FEATURE:
<223> OTHER INFORMATION: GenBank No. gi[16]077744f[]_388558.1

<400> SEQUENCE: 7

Met Ala Leu Ile Asp Leu Glu Asp Lys Ile Ala Glu Ile Val Asn Arg
1               5                   10                  15

Glu Asp His Ser Asp Phe Leu Tyr Glu Leu Leu Gly Val Tyr Asp Val
              20                  25                  30

Pro Arg Ala Thr Ile Thr Arg Leu Lys Lys Gly Asn Gln Asn Leu Thr
          35                  40                  45

Lys Arg Val Gly Glu Val His Leu Lys Asn Lys Val Trp Phe Lys Glu
      50                  55                  60

Ala Lys Lys Gly Lys Leu Phe Asp Ala Leu Ile Asp Ile Glu Gln Gln
65                  70                  75                  80

-continued

```
Val Glu Tyr Leu Ser Ala Lys Pro Arg Tyr Leu Val Thr Asp Tyr
                85                  90                  95

Asp Gly Val Leu Ala Lys Asp Thr Lys Thr Leu Glu Ala Leu Asp Val
            100                 105                 110

Lys Phe Glu Glu Leu Pro Gln Tyr Phe Asp Phe Leu Ala Trp Lys
            115                 120                 125

Gly Ile Glu Lys Val Glu Phe Glu Lys Asn Pro Ala Asp Ile Lys
            130                 135                 140

Ala Ala Glu Arg Phe Ala Arg Ile Tyr Asp Val Leu Arg Lys Glu Asn
145                 150                 155                 160

Asn Ile Ile Glu Thr Asn Arg Gly Leu Asp Leu Phe Leu Ile Arg Leu
                165                 170                 175

Leu Phe Cys Phe Phe Ala Glu Asp Thr Asp Ile Phe Lys Arg Asn Ser
                180                 185                 190

Phe Thr Asn Leu Ile Lys Thr Leu Thr Glu Glu Asp Gly Ser Asn Leu
                195                 200                 205

Asn Lys Leu Phe Ala Asp Leu Phe Ile Val Leu Asp Lys Asn Glu Arg
210                 215                 220

Asp Asp Val Pro Ser Tyr Leu Lys Glu Phe Pro Tyr Val Asn Gly Gln
225                 230                 235                 240

Leu Phe Thr Glu Pro His Thr Glu Leu Glu Phe Ser Ala Lys Ser Arg
                245                 250                 255

Lys Leu Ile Ile Glu Cys Gly Glu Leu Leu Asn Trp Ala Lys Ile Asn
                260                 265                 270

Pro Asp Ile Phe Gly Ser Met Ile Gln Ala Val Ala Ser Glu Glu Ser
                275                 280                 285

Arg Ser Tyr Leu Gly Met His Tyr Thr Ser Val Pro Asn Ile Met Lys
                290                 295                 300

Val Ile Lys Pro Leu Phe Leu Asp Lys Leu Asn Gln Ser Phe Leu Asp
305                 310                 315                 320

Ala Tyr Asp Asp Tyr Thr Lys Leu Glu Asn Leu Leu Thr Arg Ile Gly
                325                 330                 335

Lys Ile Lys Phe Phe Asp Pro Ala Cys Gly Ser Gly Asn Phe Leu Ile
                340                 345                 350

Ile Thr Tyr Lys Glu Leu Arg Arg Met Glu Ile Asn Ile Ile Lys Arg
                355                 360                 365

Leu Gln Glu Leu Leu Gly Glu Tyr Leu Tyr Val Pro Ser Val Thr Leu
                370                 375                 380

Ser Gln Phe Tyr Gly Ile Glu Ile Glu Asp Phe Ala His Asp Val Ala
385                 390                 395                 400

Lys Leu Ser Leu Trp Ile Ala Glu His Gln Met Asn Glu Glu Leu Lys
                405                 410                 415

Asn Glu Val His Asn Ala Val Arg Pro Thr Leu Pro Leu His Thr Ala
                420                 425                 430

Gly Asp Ile Arg Cys Ala Asn Ala Ile Arg Val Glu Trp Thr Glu Val
            435                 440                 445

Cys Pro Ala Gln Gly Ser Glu Val Tyr Val Phe Gly Asn Pro Pro
            450                 455                 460

Tyr Leu Gly Ser Lys Lys Gln Asn Lys Glu His Lys Ser Asp Met Leu
465                 470                 475                 480

Ser Ile Phe Gly Lys Val Lys Asn Gly Lys Met Leu Asp Tyr Ile Ser
                485                 490                 495
```

```
Ala Trp Phe Tyr Phe Gly Ala Lys Tyr Ala Ser Thr Thr Asn Ala Lys
            500                 505                 510
Val Ala Phe Val Ser Thr Asn Ser Val Thr Gln Gly Glu Gln Val Ser
            515                 520                 525
Ile Leu Trp Asn Glu Leu Phe Lys Phe Gly Ile Gln Ile Asn Phe Ala
            530                 535                 540
Tyr Lys Ser Phe Lys Trp Ala Asn Asn Ala Lys Asn Ala Ala Val
545                 550                 555                 560
Ile Val Val Ile Val Gly Phe Gly Pro Leu Asp Thr Lys Val Asn Lys
                565                 570                 575
Tyr Leu Phe Val Asp Glu Thr Lys Lys Leu Val Ser Asn Ile Ser Pro
            580                 585                 590
Tyr Leu Thr Asp Gly Glu Asn Ile Leu Val Ser Ser Arg Thr Lys Pro
            595                 600                 605
Ile Ser Asp Leu Pro Lys Leu His Phe Gly Asn Met Pro Asn Asp Gly
            610                 615                 620
Gly Gly Leu Leu Phe Thr Ile Thr Glu Tyr Thr Asp Ala Ile Asn Lys
625                 630                 635                 640
Tyr Pro Glu Leu Val Pro Tyr Phe Lys Lys Phe Ile Gly Ser Val Glu
                645                 650                 655
Phe Ile Asn Gly Gly Leu Arg Tyr Cys Leu Trp Leu Asn Glu Ala Lys
            660                 665                 670
Tyr Glu Lys Ile Lys Ser Asn Pro Leu Ile Gln Glu Arg Ile Ser Ile
            675                 680                 685
Ser Lys Asn His Arg Glu Lys Ser Thr Asp Lys Gly Thr Asn Lys Leu
            690                 695                 700
Ala Leu Thr Pro Trp Lys Phe Arg Asp Thr His Glu Thr Thr Asn Tyr
705                 710                 715                 720
Ser Ile Val Val Pro Ser Val Ser Ser Glu Asn Arg Phe Tyr Ile Pro
                725                 730                 735
Met Gly Leu Ala Gly Ala Asp Thr Ile Leu Ser Asn Leu Ile Tyr Val
            740                 745                 750
Ile Tyr Asp Ala Glu Ile Tyr Leu Leu Gly Ile Leu Met Ser Arg Met
            755                 760                 765
His Met Thr Trp Val Lys Ala Val Ala Gly Arg Leu Lys Thr Asp Tyr
770                 775                 780
Arg Tyr Ser Ala Gly Leu Cys Tyr Asn Thr Phe Pro Ile Pro Glu Leu
785                 790                 795                 800
Ser Thr Arg Arg Lys Asn Glu Ile Glu Glu Ala Ile Leu Glu Ile Leu
                805                 810                 815
Asp Leu Arg Glu Glu Gln Gly Gly Thr Leu Ala Glu Leu Tyr Asn Pro
            820                 825                 830
Ser Thr Met Pro Ile Glu Leu Lys Val Ala His Glu Lys Leu Asp Gly
            835                 840                 845
Ile Val Glu Arg Ala Tyr Arg Gln Lys Gln Phe Glu Ser Asp Glu Glu
            850                 855                 860
Arg Leu Glu Val Leu Leu Lys Leu Tyr Gln Glu Met Thr Glu Arg
865                 870                 875
```

<210> SEQ ID NO 8
<211> LENGTH: 952
<212> TYPE: PRT
<213> ORGANISM: unknown
<220> FEATURE:
<223> OTHER INFORMATION: GenBank No. gi[99]45797β´G03371.1

<400> SEQUENCE: 8

```
Met Val Met Ala Pro Thr Thr Val Phe Asp Arg Ala Thr Ile Arg His
1               5                   10                  15
Asn Leu Thr Glu Phe Lys Leu Arg Trp Leu Asp Arg Ile Lys Gln Trp
            20                  25                  30
Glu Ala Glu Asn Arg Pro Ala Thr Glu Ser Ser His Asp Gln Gln Phe
        35                  40                  45
Trp Gly Asp Leu Leu Asp Cys Phe Gly Val Asn Ala Arg Asp Leu Tyr
    50                  55                  60
Leu Tyr Gln Arg Ser Ala Lys Arg Ala Ser Thr Gly Arg Thr Gly Lys
65                  70                  75                  80
Ile Asp Met Phe Met Pro Gly Lys Val Ile Gly Glu Ala Lys Ser Leu
                85                  90                  95
Gly Val Pro Leu Asp Asp Ala Tyr Ala Gln Ala Leu Asp Tyr Leu Leu
            100                 105                 110
Gly Gly Thr Ile Ala Asn Ser His Met Pro Ala Tyr Val Val Cys Ser
        115                 120                 125
Asn Phe Glu Thr Leu Arg Val Thr Arg Leu Asn Arg Thr Tyr Val Gly
    130                 135                 140
Asp Ser Ala Asp Trp Asp Ile Thr Phe Pro Leu Ala Glu Ile Asp Glu
145                 150                 155                 160
His Ile Glu Gln Leu Ala Phe Leu Ala Asp Tyr Glu Thr Ser Ala Tyr
                165                 170                 175
Arg Glu Glu Glu Lys Ala Ser Leu Glu Ala Ser Arg Leu Met Val Glu
            180                 185                 190
Leu Phe Arg Ala Met Asn Gly Asp Asp Val Asp Glu Ala Val Gly Asp
        195                 200                 205
Asp Ala Pro Thr Thr Pro Glu Glu Glu Asp Glu Arg Val Met Arg Thr
    210                 215                 220
Ser Ile Tyr Leu Thr Arg Ile Leu Phe Leu Leu Phe Gly Asp Asp Ala
225                 230                 235                 240
Gly Leu Trp Asp Thr Pro His Leu Phe Ala Asp Phe Val Arg Asn Glu
                245                 250                 255
Thr Thr Pro Glu Ser Leu Gly Pro Gln Leu Asn Glu Leu Phe Ser Val
            260                 265                 270
Leu Asn Thr Ala Pro Glu Lys Arg Pro Lys Arg Leu Pro Ser Thr Leu
        275                 280                 285
Ala Lys Phe Pro Tyr Val Asn Gly Ala Leu Phe Ala Glu Pro Leu Ala
    290                 295                 300
Ser Glu Tyr Phe Asp Tyr Gln Met Arg Glu Ala Leu Leu Ala Ala Cys
305                 310                 315                 320
Asp Phe Asp Trp Ser Thr Ile Asp Val Ser Val Phe Gly Ser Leu Phe
                325                 330                 335
Gln Leu Val Lys Ser Lys Glu Ala Arg Arg Ser Asp Gly Glu His Tyr
            340                 345                 350
Thr Ser Lys Ala Asn Ile Met Lys Thr Ile Gly Pro Leu Phe Leu Asp
        355                 360                 365
Glu Leu Arg Ala Glu Ala Asp Lys Leu Val Ser Ser Pro Ser Thr Ser
    370                 375                 380
Val Ala Ala Leu Glu Arg Phe Arg Asp Ser Leu Ser Glu Leu Val Phe
385                 390                 395                 400
Ala Asp Met Ala Cys Gly Ser Gly Asn Phe Leu Leu Leu Ala Tyr Arg
```

-continued

```
                405                 410                 415
Glu Leu Arg Arg Ile Glu Thr Asp Ile Ile Val Ala Ile Arg Gln Arg
            420                 425                 430
Arg Gly Glu Thr Gly Met Ser Leu Asn Ile Glu Trp Glu Gln Lys Leu
            435                 440                 445
Ser Ile Gly Gln Phe Tyr Gly Ile Glu Leu Asn Trp Trp Pro Ala Lys
            450                 455                 460
Ile Ala Glu Thr Ala Met Phe Leu Val Asp His Gln Ala Asn Lys Glu
465                 470                 475                 480
Leu Ala Asn Ala Val Gly Arg Pro Pro Glu Arg Leu Pro Ile Lys Ile
                485                 490                 495
Thr Ala His Ile Val His Gly Asn Ala Leu Gln Leu Asp Trp Ala Asp
                500                 505                 510
Ile Leu Ser Ala Ser Ala Ala Lys Thr Tyr Ile Phe Gly Asn Pro Pro
            515                 520                 525
Phe Leu Gly His Ala Thr Arg Thr Ala Glu Gln Ala Gln Glu Leu Arg
            530                 535                 540
Asp Leu Trp Gly Thr Lys Asp Ile Ser Arg Leu Asp Tyr Val Thr Gly
545                 550                 555                 560
Trp His Ala Lys Cys Leu Asp Phe Phe Lys Ser Arg Glu Gly Arg Phe
                565                 570                 575
Ala Phe Val Thr Thr Asn Ser Ile Thr Gln Gly Asp Gln Val Pro Arg
                580                 585                 590
Leu Phe Gly Pro Ile Phe Lys Ala Gly Trp Arg Ile Arg Phe Ala His
            595                 600                 605
Arg Thr Phe Ala Trp Asp Ser Glu Ala Pro Gly Lys Ala Ala Val His
            610                 615                 620
Cys Val Ile Val Gly Phe Asp Lys Glu Ser Gln Pro Arg Pro Arg Leu
625                 630                 635                 640
Trp Asp Tyr Pro Asp Val Lys Gly Glu Pro Val Ser Val Glu Val Gly
                645                 650                 655
Gln Ser Ile Asn Ala Tyr Leu Val Asp Gly Pro Asn Val Leu Val Asp
                660                 665                 670
Lys Ser Arg His Pro Ile Ser Ser Glu Ile Ser Pro Ala Thr Phe Gly
            675                 680                 685
Asn Met Ala Arg Asp Gly Gly Asn Leu Leu Val Glu Val Asp Glu Tyr
            690                 695                 700
Asp Glu Val Met Ser Asp Pro Val Ala Ala Lys Tyr Val Arg Pro Phe
705                 710                 715                 720
Arg Gly Ser Arg Glu Leu Met Asn Gly Leu Asp Arg Trp Cys Leu Trp
                725                 730                 735
Leu Val Asp Val Ala Pro Ser Asp Ile Ala Gln Ser Pro Val Leu Lys
                740                 745                 750
Lys Arg Leu Glu Ala Val Lys Ser Phe Arg Ala Asp Ser Lys Ala Ala
            755                 760                 765
Ser Thr Arg Lys Met Ala Glu Thr Pro His Leu Phe Gly Gln Arg Ser
            770                 775                 780
Gln Pro Asp Thr Asp Tyr Leu Cys Leu Pro Lys Val Val Ser Glu Arg
785                 790                 795                 800
Arg Ser Tyr Phe Thr Val Gln Arg Tyr Pro Ser Asn Val Ile Ala Ser
                805                 810                 815
Asp Leu Val Phe His Ala Gln Asp Pro Asp Gly Leu Met Phe Ala Leu
            820                 825                 830
```

Ala Ser Ser Ser Met Phe Ile Thr Trp Gln Lys Ser Ile Gly Gly Arg
        835                 840                 845

Leu Lys Ser Asp Leu Arg Phe Ala Asn Thr Leu Thr Trp Asn Thr Phe
    850                 855                 860

Pro Val Pro Glu Leu Asp Glu Lys Thr Arg Gln Arg Ile Ile Lys Ala
865                 870                 875                 880

Gly Lys Lys Val Leu Asp Ala Arg Ala Leu His Pro Glu Arg Ser Leu
                885                 890                 895

Ala Glu His Tyr Asn Pro Leu Ala Met Ala Pro Glu Leu Ile Lys Ala
            900                 905                 910

His Asp Ala Leu Asp Arg Glu Val Asp Lys Ala Phe Gly Ala Pro Arg
        915                 920                 925

Lys Leu Thr Thr Val Arg Gln Arg Gln Glu Leu Leu Phe Ala Asn Tyr
    930                 935                 940

Glu Lys Leu Ile Ser His Gln Pro
945                 950

<210> SEQ ID NO 9
<211> LENGTH: 168
<212> TYPE: PRT
<213> ORGANISM: unknown
<220> FEATURE:
<223> OTHER INFORMATION: GenBank No. gi[23]451826β´N32874.1

<400> SEQUENCE: 9

Pro Ala Asp Glu Arg Ser Gln Met Asp Ala Gly Gly Lys Pro Val Glu
1               5                   10                  15

Gly Gly Asn Leu Leu Phe Ala Glu Glu Lys Gln Arg Leu Val Glu
            20                  25                  30

Gly Asn Val Asp Val Val Lys Phe Leu Lys Arg Val Tyr Gly Ala Ser
        35                  40                  45

Glu Tyr Ile Arg Gly Glu Val Arg Phe Cys Leu Trp Ile Ser Asp Ser
    50                  55                  60

Gln Glu Gln Glu Ala Lys Ser Asn Ser Asp Ile Asn Cys Lys Leu Asn
65                  70                  75                  80

Ala Val Ala Ala Phe Arg Leu Lys Ser Pro Lys Ala Ala Thr Lys Lys
                85                  90                  95

Gly Ala Ala Trp Pro His Lys Phe Glu Glu Val Lys Gln Ile Gly Asn
            100                 105                 110

Glu Val Val Thr Ile Val Pro Lys Val Ser Ser Glu Ser Arg Glu Tyr
        115                 120                 125

Leu Pro Val Gly Leu Leu Pro Arg Gly Ser Ile Val Thr Asp Leu Ala
    130                 135                 140

Phe Ala Leu Tyr Asp Ala Pro Leu Trp Asn Met Ala Leu Ile Ala Ser
145                 150                 155                 160

Arg Leu His Leu Val Trp Ile Gly
                165

<210> SEQ ID NO 10
<211> LENGTH: 909
<212> TYPE: PRT
<213> ORGANISM: unknown
<220> FEATURE:
<223> OTHER INFORMATION: GenBank No. gb[23]110638β00096791.1

<400> SEQUENCE: 10

Met Asn Pro Val Glu Ile Glu Glu Ala Val Ser Asp Leu Ala Arg Ala

-continued

```
1               5                   10                  15

Pro Tyr Asp Ala Ser Glu Phe Pro Phe Gln Phe Leu Ala Ala Phe Gly
                20                  25                  30

Asn Lys Gln Thr Thr Leu Gln Arg Leu Arg Ala Gly Asn Ser Asn Gln
                35                  40                  45

Ser Asp Leu Pro Gly Ala Val Leu Gln Arg Asn His Ile His Ile Ala
            50                  55                  60

Thr Cys Asp Ala Gly Asn Val Asp Arg Thr Leu Ala Ala Leu Arg Lys
65                      70                  75                  80

Ser Pro Lys Thr Ala Ser Gln Lys Ala Arg Phe Ile Leu Ala Thr Asp
                    85                  90                  95

Gly Val Ala Phe Gln Ala Glu Asp Met Ala Ser Gly Glu Thr Val Ala
                100                 105                 110

Cys Asn Tyr Ala Ala Phe Pro Asp Lys Phe Ala Phe Phe Leu Pro Leu
                115                 120                 125

Ala Gly Ile Thr Thr Val Gln Gln Ile Arg Glu Ser Ser Phe Asp Ile
            130                 135                 140

Lys Ala Thr Gly Arg Leu Asn Lys Leu Tyr Val Glu Leu Leu Lys Asp
145                     150                 155                 160

Asn Pro Asp Trp Ala Ser Arg Ser Glu Asp Met Asn His Phe Met Ala
                    165                 170                 175

Arg Leu Ile Phe Cys Phe Phe Ala Glu Asp Thr Asp Ile Phe Val Gly
                180                 185                 190

Glu Gly Leu Phe Ser Arg Thr Val Glu Thr Met Ser Ala Arg Asp Ala
                195                 200                 205

Ser Asp Thr His Met Val Ile Ala Glu Ile Phe Arg Ala Met Asp Thr
            210                 215                 220

Arg Leu Ala Asp Arg Ala Ala Ala Gly Ile Lys Ser Trp Ala Asp Val
225                     230                 235                 240

Phe Pro Tyr Val Asn Gly Gln Leu Phe Ser Gly Ser Thr Glu Cys Pro
                    245                 250                 255

Arg Phe Ser Lys Ile Ala Arg Ser Tyr Leu Leu His Ile Gly Ser Leu
                260                 265                 270

Asp Trp Gln Lys Ile Asn Pro Asp Ile Phe Gly Ser Met Ile Gln Ala
            275                 280                 285

Val Ala Asp Asp Glu Glu Arg Gly Ala Leu Gly Met His Tyr Thr Ser
        290                 295                 300

Val Pro Asn Ile Leu Lys Val Leu Asn Pro Leu Phe Leu Asp Asp Leu
305                 310                 315                 320

Arg Ala Lys Leu Glu Glu Ala Gly Asp Asn Ser Arg Lys Leu Leu Asn
                    325                 330                 335

Leu Arg Asn Arg Met Ala Lys Ile Arg Val Phe Asp Pro Ala Cys Gly
                340                 345                 350

Ser Gly Asn Phe Leu Val Ile Ala Tyr Lys Gln Met Arg Glu Leu Glu
                355                 360                 365

Ala Glu Ile Asn Arg Arg Gly Glu Ala Asp Arg Arg Ser Asp Ile
        370                 375                 380

Pro Leu Thr Asn Phe Arg Gly Ile Glu Leu Arg Asn Phe Pro Ala Glu
385                 390                 395                 400

Ile Ala Arg Leu Ala Leu Ile Ile Ala Glu Tyr Gln Cys Asp Val Leu
                    405                 410                 415

Tyr Arg Gly Gln Lys Glu Ala Leu Ala Glu Phe Leu Pro Leu Asp Ser
                420                 425                 430
```

-continued

```
Gln Asn Trp Ile Thr Cys Gly Asn Ala Leu Arg Leu Asp Trp Leu Ser
        435                 440                 445

Ile Cys Pro Thr Gly Thr Ala Val Lys Leu Gln Ala Asn Asp Leu
450                 455                 460

Phe Glu Met Pro Leu Asp Gln Ala Glu Ile Asp Phe Glu Asn Glu Gly
465                 470                 475                 480

Gly Glu Thr Tyr Ile Cys Gly Asn Pro Tyr Leu Gly Ala Lys Lys
                485                 490                 495

Lys Ser Ser Asp Gln Ile Glu Asp Met Lys Arg Val Gly Leu Asp Lys
                500                 505                 510

Ala Gln Leu Leu Asp Tyr Val Ser Ala Phe Ile Val Arg Gly Leu Pro
        515                 520                 525

Leu Val Ala Gln Gln Arg Cys Asp Met Ala Leu Val Ser Thr Ser Ser
        530                 535                 540

Ile Cys Gln Gly Glu Gln Val Ser Leu Ile Trp Pro Arg Ile Leu Lys
545                 550                 555                 560

Ser Ala Asn Val Lys Phe Ala Tyr Arg Pro Phe Arg Trp Ser Asn Ser
                565                 570                 575

Ala Ala Asn Asn Ala Gly Val Tyr Cys Thr Ile Ile Gly Leu Thr Gly
                580                 585                 590

Ser Glu Val Ser Asn Lys Lys Leu Phe Gly Gly Ser Val Val Glu
        595                 600                 605

Cys Ser Ser Ile Ala Pro Tyr Leu Val Pro Gly Pro Glu Ile Ile Cys
610                 615                 620

Ala Pro Arg Gln Ser Ser Ile Ser Gly Phe Ala Arg Met Val Met Gly
625                 630                 635                 640

Ser Asn Pro Val Asp Gly Lys Arg Leu Ile Phe Glu Gln Asp Glu Lys
                645                 650                 655

Glu Ser Val Val Ala Ala Asp Pro Arg Ser Glu Arg Phe Phe Lys Arg
                660                 665                 670

Tyr Gly Gly Thr Gln Glu Leu Val Asn Gly Val Asp Arg Trp Cys Leu
        675                 680                 685

Trp Ile Asn Asp Asp Gln Val Asp Asp Ala Lys Ala Ile Ala Glu Ile
        690                 695                 700

Ala Lys Val Leu Glu Ser Cys Arg Ser Tyr Arg Gln Gly Ala Gly Arg
705                 710                 715                 720

Asp Ala Gln Lys Ala Ala Asn Arg Pro His Ser Phe Cys Tyr Arg Thr
                725                 730                 735

Phe Gln Glu Asn Ile Gly Ile His Val Gly Leu Thr Ile Gly Asn Gly
                740                 745                 750

Leu Ser His Val Pro Ala Asp Leu Lys Ser Ser Gly Phe Val Ser Ser
        755                 760                 765

His Thr Ala Tyr Met Ile Tyr Gly Trp His Pro Val Glu Phe Ala Leu
        770                 775                 780

Leu Asn Ser Arg Leu Met Leu Val Trp Thr Glu Thr Val Gly Gly Arg
785                 790                 795                 800

Leu Gly Asn Gly Met Arg Phe Ser Asn Thr Ile Val Tyr Asn Thr Phe
                805                 810                 815

Pro Val Pro Ser Leu Thr Asp Gln Asn Lys Ala Asp Leu Thr Arg Cys
                820                 825                 830

Ala Glu Asp Ile Leu Leu Ala Arg Glu Ser His Phe Pro Ala Thr Ile
        835                 840                 845
```

```
Ala Asp Leu Tyr Asp Pro Glu Thr Met Pro Glu Ser Leu Arg Ala Ala
    850                 855                 860

His Asp Arg Asn Asp Glu Val Leu Glu Arg Ile Tyr Ile Gly Arg Arg
865                 870                 875                 880

Phe Arg Asn Asp Thr Glu Arg Leu Glu Lys Leu Phe Glu Leu Tyr Thr
                885                 890                 895

Lys Met Thr Gly Gly Arg Ser Ser Glu Gly Gly Ala Ala
            900                 905

<210> SEQ ID NO 11
<211> LENGTH: 1048
<212> TYPE: PRT
<213> ORGANISM: unknown
<220> FEATURE:
<223> OTHER INFORMATION: GenBank No. gi[20]803963[em]b[CA]D31540.1

<400> SEQUENCE: 11

Met Ser Leu Gly Ala Ala Gly Leu Thr Pro Ile Thr Pro Ala Ala Phe
1               5                   10                  15

Ile Lys Lys Trp Arg Lys Ser Glu Leu Gly Glu Arg Gln Ala Ala Gln
            20                  25                  30

Glu His Phe Leu Asp Ile Cys Ser Leu Val Gly His Pro Ser Pro Ser
        35                  40                  45

Asp Glu Asp Pro Thr Gly Ala Phe Phe Ala Phe Glu Lys Gly Ala Asn
50                  55                  60

Lys Leu Gly Gly Gly Lys Gly Phe Ala Asp Val Trp Lys Lys Gly His
65                  70                  75                  80

Phe Ala Trp Glu Tyr Lys Arg Lys Gly Asn Leu Asp Glu Ala Leu
                85                  90                  95

Leu Gln Leu Met Arg Tyr Ala Pro Ala Leu Leu Ser Pro Pro Leu His
            100                 105                 110

Ile Val Cys Asp Ile Glu Arg Leu Arg Ile His Thr Ala Trp Thr Asn
            115                 120                 125

Thr Val Pro Ser Thr Tyr Val Ile Thr Leu Asp Asp Leu Ala Glu Pro
    130                 135                 140

Ser Ala Arg Glu Met Leu His Asn Val Phe Phe Ser Pro Glu Lys Leu
145                 150                 155                 160

Arg Pro Thr Arg Thr Arg Ala Ala Val Thr Lys Glu Ala Ala Asp Lys
                165                 170                 175

Phe Ser Ala Ile Ala Leu Arg Val Gln Gly Arg Gly Thr Pro Asp Glu
            180                 185                 190

Ile Ala His Phe Val Asn Gln Leu Val Phe Cys Phe Ala Gln Ser
            195                 200                 205

Val Ser Leu Leu Pro Asp Gly Leu Phe Thr Lys Leu Leu Lys Arg Ser
    210                 215                 220

Ala Arg Ala Pro Glu Arg Ala Met Ser Tyr Leu Asp Lys Leu Phe Glu
225                 230                 235                 240

Ala Met Glu Arg Gly Gly Glu Phe Asp Leu Thr Asp Ile Thr Trp Phe
                245                 250                 255

Asn Gly Gly Leu Phe Asp Gly Arg Arg Ala Leu Arg Leu Asp Asp Gly
            260                 265                 270

Asp Ile Gly Leu Leu Val Ala Ala Asp Ser Leu Asp Trp Gly Leu Ile
            275                 280                 285

Asp Pro Thr Ile Phe Gly Thr Leu Phe Glu Arg Phe Leu Asp Pro Glu
    290                 295                 300
```

-continued

```
Lys Arg Ala Gln Ile Gly Ala His Tyr Thr Asp Pro Glu Lys Ile Met
305                 310                 315                 320

Arg Leu Val Asp Pro Val Ile Leu Arg Pro Leu Arg Gln Glu Trp Glu
            325                 330                 335

Gln Ala Arg Arg Glu Ile Val Glu Leu Leu Asn Gly Asn Arg Lys Pro
        340                 345                 350

Pro Met Arg Arg Gln Gln Ser Arg Arg Met Lys Arg Glu Glu Ala Ala
    355                 360                 365

Ala Glu Val Arg Ser Arg Phe Thr Glu Arg Leu Arg Lys Leu Arg Ile
370                 375                 380

Leu Asp Pro Ala Cys Gly Ser Gly Asn Phe Leu Tyr Leu Ala Leu Gln
385                 390                 395                 400

Gly Val Lys Asp Ile Glu His Arg Ala Asn Leu Asp Cys Glu Met Leu
            405                 410                 415

Gly Met Pro Ala Gln Leu Pro Leu Val Gly Pro Glu Ile Leu Arg Gly
        420                 425                 430

Ile Glu Ile Asn Met Met Ala Ala Glu Leu Ala Arg Thr Thr Ile Trp
    435                 440                 445

Ile Gly Asp Ile Gln Trp Gln Ile Lys Asn Gly Ile Arg Ser Lys Ser
450                 455                 460

Ile Pro Ile Leu Arg Lys Leu Asp Ala Ile Glu Arg Arg Asp Ala Leu
465                 470                 475                 480

Val Arg Gln Ala Gln Asp Val Asp Thr Ala Arg Asp Ala Gln Gly Asp
            485                 490                 495

Leu Leu Ala Ala Leu Gln Pro Val Ser Glu Asp Ala Glu Ala Glu Trp
        500                 505                 510

Pro Glu Ala Glu Phe Ile Val Gly Asn Pro Pro Phe Val Gly Val Arg
    515                 520                 525

Leu Met Arg Gln Ala Leu Gly Asp Pro Thr Val Asp Arg Leu Phe Asp
530                 535                 540

Val Tyr Asp Gly Arg Val Ser Arg Glu Ala Asp Leu Val Cys Tyr Trp
545                 550                 555                 560

Val Glu Lys Ser Arg Ala Ala Val Ala Ala Asp Arg Thr Arg Arg Val
            565                 570                 575

Gly Leu Val Thr Thr Asn Ser Ile Arg Gly Gly Ala Asn Arg Arg Val
        580                 585                 590

Leu Asp Arg Ile Ile Ala Glu Ser Arg Leu Phe Glu Ala Trp Ser Asp
    595                 600                 605

Glu Pro Trp Val Val Asp Gly Ala Ala Val Arg Val Ser Leu Ile Cys
610                 615                 620

Phe Gly His Gly Glu Asp Pro Leu Cys Leu Asp Gly Arg Thr Val Ala
625                 630                 635                 640

Gln Ile Asn Ala Asp Leu Thr Ala Gly Val Thr Asp Leu Thr Lys Ala
            645                 650                 655

Arg Arg Leu Ser Glu Asn Gln Asn Val Ala Phe Met Gly Asp Thr Lys
        660                 665                 670

Gly Gly Ala Phe Asp Val Pro Gly Ser Leu Ala Arg Ala Trp Leu Ser
    675                 680                 685

Met Pro Met Asn Pro Asn Gly Arg Pro Asn Ser Asp Val Leu Arg Pro
690                 695                 700

Trp Arg Asn Gly Met Asp Val Ala Arg Gly Arg Asp Met Trp Ile
705                 710                 715                 720

Val Asp Phe Gly Trp Glu Met Ser Glu Gln Glu Ala Ala Leu Tyr Glu
```

```
                    725                 730                 735
Ala Pro Phe Gln His Ile Arg Glu His Val Phe Pro Glu Arg Ser Lys
                740                 745                 750
Asn Arg Arg Asp Ala Tyr Arg Glu Arg Trp Trp Arg His Val Glu Pro
                755                 760                 765
Arg Pro Ala Phe His Ala Ser Leu Gln Gly His Ser Arg Tyr Met Ala
                770                 775                 780
Thr Pro Arg Val Ala Lys His Arg Thr Phe Val Trp Leu Asp Gln Ala
785                 790                 795                 800
Ile Val Pro Asp Ser Arg Ile Phe Ala Phe Ser Arg Ser Asp Val
                    805                 810                 815
Phe Phe Gly Ile Leu His Ser Arg Phe His Glu Ala Trp Ser Phe Gly
                820                 825                 830
Thr Cys Ser Trp His Gly Val Gly Asn Asp Pro Thr Tyr Asn Ser Ala
            835                 840                 845
Gly Val Phe Glu Thr Phe Pro Phe Pro Glu Gly Leu Thr Pro Asp Ile
        850                 855                 860
Pro Ala Val Arg Tyr Glu Lys Asp Ser Arg Ala Ile Ala Ile Ser Lys
865                 870                 875                 880
Ala Ala Lys Arg Leu Asp Asp Ile Arg Asn Ala Trp Leu Asn Pro Ser
                885                 890                 895
Asp Leu Val Gln Ile Lys Pro Glu Val Val Pro Gly Tyr Pro Asp Arg
                900                 905                 910
Ile Leu Pro Lys Asp Ile Ala Ser Asp Ala Ile Leu Arg Asp Arg Thr
            915                 920                 925
Leu Thr Asn Leu Tyr Asn Arg Arg Pro Gln Trp Leu Val Asp Ala His
        930                 935                 940
Ser Asp Leu Asp Ala Ala Val Ala Gly Ala Tyr Gly Trp Pro Ala Asp
945                 950                 955                 960
Ile Ser Glu Asp Glu Ala Leu Ala Asn Leu Leu Glu Leu Asn Leu Ala
                965                 970                 975
Arg Glu Ala Phe Asn Glu His Ala Lys Ser Gly Leu Lys Thr Arg Lys
                980                 985                 990
Pro Arg Arg Arg Pro Thr Pro Glu  Glu Val Arg Arg Ala  Pro Gln Met
            995                 1000                1005
Lys Leu  Pro Ile Ala Gly  Gly Arg Lys Ser Val  Val Gly Pro Gln
        1010                1015                1020
Gln Leu  Thr Thr Lys Asp  Arg Glu Asn Gln Pro Thr  Ser Ala Glu
        1025                1030                1035
Arg Pro  Arg Asn Thr Lys  Arg Arg Thr Ser
        1040                1045

<210> SEQ ID NO 12
<211> LENGTH: 959
<212> TYPE: PRT
<213> ORGANISM: unknown
<220> FEATURE:
<223> OTHER INFORMATION: GenBank No. gi[16]125079f[]_419643.1

<400> SEQUENCE: 12

Asp Leu Cys Arg Met Leu Glu Val Pro Thr Pro Ala Glu Asp Asp Pro
1               5                   10                  15

Leu Gly Glu Arg Tyr Cys Phe Glu Arg Gly Ala Ala Lys Thr Gly Gly
                20                  25                  30

Gly Asp Gly Trp Ala Asp Val Trp Arg Lys Gly Cys Phe Gly Trp Glu
```

```
                35                  40                  45
Tyr Lys Gly Lys His Lys Asn Leu Asp Ala Ala Leu Arg Gln Leu Gln
 50                  55                  60
Ala Tyr Ala Leu Asp Leu Gln Asn Pro Pro Tyr Leu Val Val Ser Asp
 65                  70                  75                  80
Met Glu Arg Ile Ile Val His Thr Asn Trp Thr Asn Thr Ile Ser Arg
                 85                  90                  95
Lys Ile Glu Phe Thr Leu Asp Asp Leu His Glu Pro Glu Lys Leu Ala
                100                 105                 110
Met Leu Arg Gln Val Phe Asp Gly Ser Asp Ser Leu Lys Pro Lys Ile
                115                 120                 125
Ser Pro Gln Glu Leu Thr Ala Lys Val Ala Gln Arg Phe Gly Asp Leu
130                 135                 140
Gly Arg Arg Leu Gln Glu Arg Gly His His Pro Arg Asp Val Ala His
145                 150                 155                 160
Phe Leu Asn Arg Val Val Phe Cys Met Phe Ala Glu Asp Ala Lys Leu
                165                 170                 175
Leu Pro Glu Gly Leu Phe Thr Arg Leu Thr Arg Ser Met Gln Met Arg
                180                 185                 190
Pro Pro Ala Glu Ala Ala Pro Gln Phe Asp Ala Leu Phe Ala Met Met
                195                 200                 205
Arg Ala Gly Gly Met Phe Gly Ala Asp Ile Val His Trp Phe Asn Gly
210                 215                 220
Gly Leu Phe Asp Glu Lys Pro Ala Leu Pro Leu Glu Arg Ala Asp Ile
225                 230                 235                 240
Lys Leu Ile His Asp Thr Ala Ala Glu His Asp Trp Ser Asp Leu Asp
                245                 250                 255
Pro Ser Val Phe Gly Asn Met Phe Glu Glu Ala Leu Lys Ala Thr Arg
                260                 265                 270
Glu Arg Ala Ala Leu Gly Ala His Tyr Thr Asp Arg Glu Lys Ile Leu
                275                 280                 285
Lys Ile Ile Asp Pro Val Ile Thr Trp Pro Leu Met Ala Gln Trp Glu
290                 295                 300
Thr Ala Leu Ala Glu Ile Arg Ala Ala Leu Asp Ala Arg Ala Ala Ala
305                 310                 315                 320
Glu Ala Glu Arg Lys Ala Val Leu Glu Ala Ala Glu Ala Met Arg
                325                 330                 335
Ala Asp Pro Val Lys Ala Lys Ala Gly Glu Ala Ala Arg Arg Lys Thr
                340                 345                 350
Leu Thr Ala Ile Ala Lys Arg Ser Asp Ala Ala Leu Gly Gln Ala Lys
                355                 360                 365
Asp Arg Leu Glu Ala Phe Leu Ser Arg Leu Ala Ala Phe Arg Val Leu
                370                 375                 380
Asp Pro Ala Cys Gly Ser Gly Asn Phe Leu Tyr Val Ala Leu His Ala
385                 390                 395                 400
Leu Lys Asp Ile Glu Arg Arg Ala Leu Val Asp Ala Glu Arg Leu Gly
                405                 410                 415
Leu Glu Val Pro Thr Pro Arg Val Gly Leu Ala Cys Val Arg Gly Ile
                420                 425                 430
Glu Ile Glu Glu Tyr Ala Ala Glu Leu Ala Arg Val Thr Leu Trp Ile
                435                 440                 445
Gly Asp Leu Gln Trp His Ala Lys Asn Asn Tyr Arg Gly Phe Ala Glu
450                 455                 460
```

-continued

```
Pro Ile Leu Ser Ser Leu Asp Gln Ile Glu Cys Arg Asp Ala Leu Leu
465                 470                 475                 480

Asn Ala Asp Gly Thr Glu Ala Gln Trp Pro Ala Val Asp Val Ile Val
                485                 490                 495

Gly Asn Pro Pro Phe Leu Gly Ser Lys Arg Leu Arg Asp Gly Leu Gly
            500                 505                 510

Asn Asp Tyr Val Glu Arg Leu Phe Ser Thr Tyr Arg Gly Lys Val Pro
        515                 520                 525

Ala Glu Ala Asp Phe Val Ala Tyr Trp Ile Ala Lys Ala Trp Glu Leu
530                 535                 540

Val Gln Ala Gln Gln Gly Arg Arg Ala Gly Leu Val Thr Thr Asn Ser
545                 550                 555                 560

Val Arg Gly Gly Ala Ser Arg Lys Val Leu Asp Pro Ile Ala Asp Ala
                565                 570                 575

Gly Ala Leu Met Glu Ala Trp Ala Asp Glu Pro Trp Ala Leu Glu Gly
            580                 585                 590

Ala Ala Val Arg Val Ser Met Phe Gly Phe Gly Asp Gly Phe Ala Glu
        595                 600                 605

Arg Arg Leu Glu Gly Arg Lys Ala Glu His Leu His Ser Asp Phe Arg
610                 615                 620

Gly Ala Ser Thr Asp Val Thr Lys Ala Leu Arg Leu Lys Glu Asn Ala
625                 630                 635                 640

Ser Ile Ala Phe Met Gly Asp Thr Lys Gly Gly Ala Phe Asp Val Ser
                645                 650                 655

Gly Glu Ile Ala Arg Glu Trp Leu Arg Leu Pro Leu Asn Pro Asn Gly
            660                 665                 670

Arg Pro Asn Ser Asp Val Leu Lys Pro Trp Arg Asn Ala Met Asp Met
        675                 680                 685

Thr Arg Arg Ser Ser Asp Lys Trp Ile Ile Asp Phe Gly Trp Thr Met
690                 695                 700

Ser Glu Ala Asp Ala Ala Leu Phe Glu Thr Pro Phe Arg His Val Leu
705                 710                 715                 720

Leu His Val Lys Pro Glu Arg Asp Arg Asn Asn Arg Glu Met Tyr Arg
                725                 730                 735

Leu Asn Trp Trp Lys His Val Glu Pro Arg Gln Gly Leu Met Lys Arg
            740                 745                 750

Val Pro Ala Leu Ser Arg Leu Leu Val Thr Pro Glu Val Ser Lys His
        755                 760                 765

Arg Leu Phe Ile Trp Leu Asp Ala Arg Val Leu Pro Asp His Lys Leu
770                 775                 780

Gln Val Val Thr Leu Asp Asp Cys Ser Phe Gly Val Leu His Ser
785                 790                 795                 800

Arg Phe His Glu Val Trp Ala Leu Ala Ala Gly Ser Trp His Gly Ser
                805                 810                 815

Gly Asn Asp Pro Arg Tyr Thr Ile Ser Thr Thr Phe Glu Thr Phe Pro
            820                 825                 830

Phe Pro Glu Gly Leu Thr Pro Asn Ile Ala Ala Val Asp Tyr Glu Gly
        835                 840                 845

Asp Pro Arg Ala Gln Ala Ile Ala Ala Ala Ala Glu Leu Asn Arg
850                 855                 860

Leu Arg Glu Ala Trp Leu Asn Pro Pro Asp Leu Val Arg Ile Glu Pro
865                 870                 875                 880
```

-continued

```
Glu Val Val Pro Gly Tyr Pro Asp Arg Val Leu Pro Val Ser Pro Glu
                885                 890                 895
Ala Gly Ala Glu Leu Lys Lys Arg Thr Leu Thr Asn Leu Tyr Asn Gln
            900                 905                 910
Arg Pro Ala Trp Leu Asp Met Ala His Gln Arg Leu Asp Ala Ala Val
        915                 920                 925
Ala Ala Ala Tyr Gly Trp Pro Asp Gly Leu Thr Asp Asp Glu Ile Leu
    930                 935                 940
Glu Arg Leu Phe Ala Leu Asn Gln Glu Arg Ala Ala Ala Gly Arg
945                 950                 955
```

<210> SEQ ID NO 13
<211> LENGTH: 909
<212> TYPE: PRT
<213> ORGANISM: unknown
<220> FEATURE:
<223> OTHER INFORMATION: GenBank No. gi[15]807788f[]_285443.1

<400> SEQUENCE: 13

```
Met His Pro Gln Glu Phe Ala Asp Thr Trp Ser Arg Arg Ala Leu Lys
1               5                   10                  15
Ala Thr Glu Arg Asp Ser Tyr Val Gln His Trp Leu Asp Leu Cys Gln
            20                  25                  30
Leu Leu His His Glu Ala Pro Gly Ala Asp Pro Asp Tyr Lys Phe Glu
        35                  40                  45
Arg Arg Val Thr Lys Val Gly Thr Lys Asp Lys Gly Phe Ala Asp Val
    50                  55                  60
Phe Lys Lys Ala His Phe Ile Thr Glu Tyr Lys Arg Pro Gly Ser Asp
65                  70                  75                  80
Leu Gly Ala Ala Leu Gln Gln Ala Thr Leu Tyr Ser Arg Asp Leu Gly
                85                  90                  95
Asn Pro Pro Leu Leu Leu Thr Ser Asp Phe Gln Arg Ile Glu Ile Asn
            100                 105                 110
Thr Ala Phe Thr Gly Thr Ser Pro Lys Ser Tyr Leu Ile Thr Leu Asp
        115                 120                 125
Asp Ile Ala Glu Asn Arg Val Val Gly Gly Asn Asp Val Pro Ala Leu
    130                 135                 140
Gln Ile Leu His Ser Ala Leu His Gln Pro Tyr Asp Leu Asp Pro Arg
145                 150                 155                 160
Leu Phe Arg Glu Arg Ile Thr Thr Asp Ala Thr Arg Gln Val Gly Leu
                165                 170                 175
Val Ala Arg Arg Leu Gly Glu Arg Glu Gly Arg Thr Arg Ala Ala His
            180                 185                 190
Met Met Met Arg Val Val Phe Ala Leu Phe Ala Glu Asp Thr Gly Met
        195                 200                 205
Leu Glu Arg Gly Ile Val Thr Arg Leu Leu Glu Arg Ala Arg Ala Pro
    210                 215                 220
Pro Gly Glu Asp Gln Leu Tyr Phe Gln Asp Leu Phe Gly Ala Met Lys
225                 230                 235                 240
Gly Gly Gly Glu Phe Trp Gly Thr Asp Ile Arg His Phe Asn Gly Gly
                245                 250                 255
Leu Phe Asp Ser Glu Asp Ala Leu Leu Thr Ser Glu Asp Ala Ala
            260                 265                 270
Ala Leu Ile Ile Ala Ala Lys Leu Asp Trp Ser Glu Val Glu Pro Ser
        275                 280                 285
```

-continued

```
Ile Phe Gly Thr Leu Phe Glu Asn Ser Leu Asp Val Asp Thr Arg Ser
    290                 295                 300

Arg Arg Gly Ala His Tyr Thr Ser Val Asn Asp Ile Glu Arg Ile Val
305                 310                 315                 320

Asp Arg Val Val Met Glu Pro Leu Trp Ala Glu Trp Asp Ala Leu Arg
                325                 330                 335

Leu Ser Leu Pro Glu Leu Lys Lys Asn Val Arg Leu Glu Arg Leu Phe
            340                 345                 350

Ala Phe Gln Asp Arg Leu Thr Ala Val Arg Ile Leu Asp Pro Ala Cys
        355                 360                 365

Gly Ser Gly Asn Phe Leu Phe Val Ala Leu Lys Lys Leu Leu Asp Leu
    370                 375                 380

Glu Tyr Gln Val Arg Met Ala Ala Val Met Asn Asp Ile Gly Glu Phe
385                 390                 395                 400

Glu Met Pro Pro Leu Val His Pro Gln Gln Met Leu Gly Ile Glu Ile
                405                 410                 415

Glu Thr Phe Ala His Glu Leu Ala Ser Ile Thr Leu Trp Met Gly Tyr
            420                 425                 430

Phe Gln Trp Lys Arg Ala His Gly Gly His Trp Glu Thr Pro Ile Leu
        435                 440                 445

Gln Arg Leu Asp Asn Ile Gln Asn Arg Asp Ala Leu Leu Asn Pro Asp
    450                 455                 460

Gly Thr Glu Ala Thr Trp Pro Arg Ala Asp Phe Ile Val Gly Asn Pro
465                 470                 475                 480

Pro Phe Leu Gly Asp Lys Met Met Arg Ser Gln Leu Gly Glu Ala Tyr
                485                 490                 495

Thr Thr Gln Leu Arg Glu Thr Phe Lys Asp Arg Leu Pro Gly Gln Ser
            500                 505                 510

Asp Leu Val Cys Tyr Trp Pro Glu Lys Ala Arg Ala Leu Ile Glu Ala
        515                 520                 525

Gly Val Thr Thr Arg Ala Gly Phe Val Thr Thr Asn Ser Ile Arg Gly
    530                 535                 540

Gly Lys Asn Arg Val Val Leu Glu Arg Ile Lys Ala Thr Gly Asp Leu
545                 550                 555                 560

Phe Met Ala Trp Pro Asp Glu Pro Trp Gln Gln Asn Gly Ala Ala Val
                565                 570                 575

Arg Val Ser Leu Phe Gly Phe Asp Asn Gly Thr Glu Thr Leu Arg Thr
            580                 585                 590

Leu Asn Asp Gly His Val Gly Val Ile Asn Ala Asp Leu Asn Ala Gly
        595                 600                 605

Thr Asp Val Lys Gln Ala Gln Lys Leu Pro Glu Asn Ala Gly Val Ser
    610                 615                 620

Phe Ile Gly Thr Gln Lys Gly Gly Ala Phe Asp Ile Pro Gly Asp Leu
625                 630                 635                 640

Ala Arg Ser Trp Leu Ser Val Pro Asn Pro Asp Arg Val Ser Asn Ala
                645                 650                 655

Asp Val Leu Lys Pro Trp Val Asn Gly Met Asp Leu Thr Arg Arg Pro
            660                 665                 670

Ser Gly Arg Trp Ile Ile Asp Phe Ala Gln Met Asp Glu Gly Glu Ala
        675                 680                 685

Arg Gln Tyr Leu Gln Pro Met Ala Tyr Val Glu Gln Lys Ile Arg Pro
    690                 695                 700

Glu Arg Ala Thr Asn Ser Asp Arg Pro Ser Arg Glu Arg Trp Trp Leu
```

-continued

```
                705                 710                 715                 720

His Gln Arg Ser Arg Pro Glu Leu Arg Glu Ala Thr Ile Glu Leu Asp
                        725                 730                 735

Arg Phe Ile Gly Ile Pro Arg Val Ala Lys His Leu Leu Pro Val Trp
                        740                 745                 750

Leu Pro Glu Gly Thr Leu Pro Asp Ser Gln Val Val Ile Ala Arg
                        755                 760                 765

Asp Asp Asp Phe Ile Phe Gly Val Leu Ala Ser Thr Ile His Arg Ser
                770                 775                 780

Trp Ala Arg Met Gln Gly Thr Tyr Met Gly Val Gly Asn Asp Leu Arg
        785                 790                 795                 800

Tyr Thr Pro Ser Thr Cys Phe Glu Thr Phe Pro Val Pro Ala Pro Thr
                        805                 810                 815

Asp Glu Gln Arg Ala Glu Ile Glu Lys Trp Ala Lys Tyr Ile Val Gln
                        820                 825                 830

Leu Arg Glu His Leu Leu Asn Gln Asp Ala Lys Gly Thr Leu Thr Gly
                        835                 840                 845

Ile Tyr Asn Gln Leu Glu Lys Leu Arg Asn Ser Pro Asp Ala Ala His
                850                 855                 860

Pro Val Ser Ala Leu Ala Thr Ala His Asp Lys Leu Asp Gln Ala Val
        865                 870                 875                 880

Ala Thr Ala Tyr Gly Trp Glu Trp Pro Leu Asn Glu Asp Gln Val Leu
                        885                 890                 895

Glu Arg Leu Leu Ala Leu Asn Leu Glu Arg Cys Pro Ala
                        900                 905
```

<210> SEQ ID NO 14
<211> LENGTH: 955
<212> TYPE: PRT
<213> ORGANISM: unknown
<220> FEATURE:
<223> OTHER INFORMATION: GenBank No. gi[15]807258f[]_295988.1
<220> FEATURE:
<221> NAME/KEY: misc_feature
<222> LOCATION: (920)..(920)
<223> OTHER INFORMATION: Xaa can be any naturally occurring amino acid

<400> SEQUENCE: 14

```
Met Pro Gln Thr Glu Thr Ala Gln Arg Met Glu Asp Phe Val Ala Tyr
1               5                   10                  15

Trp Arg Thr Leu Lys Gly Asp Glu Lys Gly Glu Ser Gln Val Phe Leu
                20                  25                  30

Asp Arg Leu Phe Gln Ala Phe Gly His Ala Gly Tyr Lys Glu Ala Gly
            35                  40                  45

Ala Glu Leu Glu Tyr Arg Val Ala Lys Gln Gly Gly Lys Lys Phe
        50                  55                  60

Ala Asp Leu Leu Trp Arg Pro Arg Val Leu Ile Glu Met Lys Lys Arg
65                  70                  75                  80

Gly Glu Lys Leu Ala Asn His Tyr Gln Gln Ala Phe Asp Tyr Trp Leu
                85                  90                  95

Lys Leu Val Pro Asp Arg Pro Arg Tyr Ala Val Leu Cys Asn Phe Asp
                100                 105                 110

Glu Leu Trp Val Tyr Asp Phe Asn Gln Gln Leu Asp Glu Pro Met Asp
            115                 120                 125

Arg Leu Arg Ile Glu Glu Leu Pro Glu Arg Tyr Thr Val Leu Asn Phe
        130                 135                 140
```

-continued

```
Met Phe Glu Gln Glu Arg Ala Pro Leu Phe Gly Asn Asn Arg Val Asp
145                 150                 155                 160

Val Thr Arg Glu Ala Ala Asp Ser Val Ala Lys Val Leu Asn Ser Val
                165                 170                 175

Ile Ala Arg Gly Glu Asp Arg Ala Arg Ala Gln Arg Phe Leu Leu Gln
            180                 185                 190

Cys Val Met Ala Met Phe Ala Glu Asp Phe Glu Leu Ile Pro Arg Gly
        195                 200                 205

Phe Phe Thr Glu Leu Ala Asp Asp Ala Arg Ala Gly Arg Gly Ser Ser
    210                 215                 220

Phe Asp Leu Phe Gly Gly Leu Phe Arg Gln Met Asn Thr Ser Glu Arg
225                 230                 235                 240

Ala Arg Gly Gly Arg Phe Ala Pro Ile Pro Tyr Phe Asn Gly Gly Leu
                245                 250                 255

Phe Arg Ala Val Asp Pro Ile Glu Leu Asn Arg Asp Glu Leu Tyr Leu
            260                 265                 270

Leu His Lys Ala Ala Leu Glu Asn Asn Trp Ala Arg Ile Gln Pro Gln
        275                 280                 285

Ile Phe Gly Val Leu Phe Gln Ser Ser Met Asp Lys Lys Glu Gln His
    290                 295                 300

Ala Lys Gly Ala His Tyr Thr Ser Glu Ala Asp Ile Met Arg Val Val
305                 310                 315                 320

Leu Pro Thr Ile Val Thr Pro Phe Gln Arg Gln Ile Glu Ala Ala Thr
                325                 330                 335

Thr Gln Lys Glu Leu Arg Ala Ile Leu Asp Glu Leu Ala Ser Phe Gln
            340                 345                 350

Val Leu Asp Pro Ala Cys Gly Ser Gly Asn Phe Leu Tyr Val Ala Tyr
        355                 360                 365

Arg Glu Leu Arg Arg Leu Glu Ala Arg Ala Leu Leu Arg Leu Arg Asp
    370                 375                 380

Leu Ser Ala Pro Gly Thr Ala Leu Pro Pro Ala Arg Val Ser Ile Arg
385                 390                 395                 400

Gln Met His Gly Leu Glu Tyr Asp Pro Phe Gly Val Glu Leu Ala Lys
                405                 410                 415

Val Thr Leu Thr Leu Ala Lys Glu Leu Ala Ile Arg Glu Met His Asp
            420                 425                 430

Leu Leu Gly Asn Thr Gly Leu Asp Phe Asp Gln Pro Leu Pro Leu Asp
        435                 440                 445

Asn Leu Asp Asp Arg Ile Val Gln Gly Asp Ala Leu Phe Thr Pro Trp
    450                 455                 460

Pro Arg Val Asp Ala Ile Val Gly Asn Pro Pro Phe Gln Ser Lys Asn
465                 470                 475                 480

Lys Leu Gln Arg Glu Met Gly Ala Ala Tyr Val Lys Lys Leu Arg Ala
                485                 490                 495

His Tyr Pro Asp Val Pro Gly Arg Ala Asp Tyr Cys Val Tyr Trp Ile
            500                 505                 510

Arg Lys Ala His Asp Gln Leu Gly Ser Gly Gln Arg Ala Gly Leu Val
        515                 520                 525

Gly Thr Asn Thr Ile Arg Gln Asn Asp Ser Arg Val Gly Gly Leu Asp
    530                 535                 540

Tyr Val Val Gln His Gly Gly Thr Ile Thr Asp Ala Val Gly Thr Gln
545                 550                 555                 560

Val Trp Ser Gly Asp Ala Ala Val His Val Ser Ile Val Asn Trp Val
```

-continued

```
                565                 570                 575
Lys Gly Pro Ala Glu Gly Pro Lys His Leu Ala Trp Gln Val Gly Asp
            580                 585                 590
His Arg Thr Ser Pro Trp Gln Ser Thr Glu Leu Pro Val Ile Asn Ser
        595                 600                 605
Ala Leu Ser Ala Gly Thr Asp Val Thr Gln Ala Gln Lys Leu Arg Val
    610                 615                 620
Asn Met Asn Ser Gly Ala Cys Tyr Gln Gly Gln Thr His Gly His Lys
625                 630                 635                 640
Gly Phe Leu Leu Asp Gly Leu Glu Ala Gly Gln Met Leu Ser Ala Glu
                645                 650                 655
Arg Lys Asn Ala Glu Val Ile Phe Pro Tyr Leu Thr Gly Asp Glu Leu
            660                 665                 670
Leu Arg Thr Ser Pro Pro His Pro Thr Arg Tyr Val Ile Asp Phe Gln
        675                 680                 685
Pro Arg Asp Val Phe Gly Ala Arg Ala Tyr Lys Leu Pro Phe Ala Arg
    690                 695                 700
Ile Glu Arg Glu Val Leu Pro Thr Arg Gln Ala Ala Ala Glu Glu
705                 710                 715                 720
Glu Ala Arg Asn Ala Glu Val Leu Ala Ala Asn Pro Lys Ala Lys Thr
                725                 730                 735
Asn Lys His His Arg Asn Phe Leu Asn Gln Trp Trp Ala Leu Ser Tyr
            740                 745                 750
Gly Arg Ser Glu Met Ile Glu Lys Ile Ser Ser Leu Ser Arg Tyr Ile
        755                 760                 765
Val Cys Ser Arg Val Thr Lys Arg Gln Val Phe Glu Phe Leu Asp Asn
    770                 775                 780
Gly Ile Arg Pro Ser Asp Gly Leu Gln Ile Phe Ala Phe Glu Asp Asp
785                 790                 795                 800
Tyr Ser Phe Gly Val Ile Gln Ser Ser Val His Trp Gln Trp Leu Ile
                805                 810                 815
Ala Arg Gly Gly Thr Leu Thr Ala Arg Leu Met Tyr Thr Ser Asp Thr
            820                 825                 830
Val Phe Asp Thr Phe Pro Trp Pro Asp Pro Thr Leu Ala Gln Val Arg
        835                 840                 845
Ala Val Ala Ala Ala Val Lys Leu Arg Glu Leu Arg Asn Lys Val
    850                 855                 860
Met Arg Glu Gln Gly Trp Ser Leu Arg Asp Leu Tyr Arg Thr Leu Asp
865                 870                 875                 880
Met Pro Gly Lys Asn Pro Leu Arg Asp Ala Gln Glu Arg Leu Asp Ala
                885                 890                 895
Ala Val Ser Ala Ala Tyr Gly Leu Pro Ala Gly Ala Asp Met Leu Asp
            900                 905                 910
Phe Leu Leu Ala Leu Asn Ala Xaa Val Ala Ala Ala Glu Ala Arg Gly
        915                 920                 925
Ala Ala Val Thr Gly Pro Gly Leu Pro Ala Gly Leu Asn Thr Ala Asp
    930                 935                 940
Phe Val Thr Ala Asp Ala Val Arg Pro Leu Gly
945                 950                 955

<210> SEQ ID NO 15
<211> LENGTH: 14
<212> TYPE: PRT
<213> ORGANISM: unknown
```

```
<220> FEATURE:
<223> OTHER INFORMATION: first 14 amino terminal residues of MmeI

<400> SEQUENCE: 15

Ala Leu Ser Trp Asn Glu Ile Arg Arg Lys Ala Ile Glu Phe
1               5                   10

<210> SEQ ID NO 16
<211> LENGTH: 29
<212> TYPE: PRT
<213> ORGANISM: unknown
<220> FEATURE:
<223> OTHER INFORMATION: first 29 residues of the 25kD peptide
<220> FEATURE:
<221> NAME/KEY: MISC_FEATURE
<222> LOCATION: (20)..(20)
<223> OTHER INFORMATION: X = Xaa (any amino acid)
<220> FEATURE:
<221> NAME/KEY: MISC_FEATURE
<222> LOCATION: (21)..(21)
<223> OTHER INFORMATION: X = Xaa (any amino acid)
<220> FEATURE:
<221> NAME/KEY: MISC_FEATURE
<222> LOCATION: (23)..(23)
<223> OTHER INFORMATION: X = Xaa (any amino acid)
<220> FEATURE:
<221> NAME/KEY: MISC_FEATURE
<222> LOCATION: (25)..(25)
<223> OTHER INFORMATION: X = Xaa (any amino acid)

<400> SEQUENCE: 16

Met Lys Ile Ser Asp Glu Phe Gly Asn Tyr Phe Ala Arg Ile Pro Leu
1               5                   10                  15

Lys Ser Thr Xaa Xaa Ile Xaa Glu Xaa Asn Ala Leu Gln
            20                  25

<210> SEQ ID NO 17
<211> LENGTH: 40
<212> TYPE: PRT
<213> ORGANISM: unknown
<220> FEATURE:
<223> OTHER INFORMATION: first 40 amino acid residues obtained from the
      14 kD fragment
<220> FEATURE:
<221> NAME/KEY: MISC_FEATURE
<222> LOCATION: (36)..(36)
<223> OTHER INFORMATION: X=Xaa (any amino acid)

<400> SEQUENCE: 17

Met Asp Ala Lys Lys Arg Arg Asn Leu Gly Ala His Tyr Thr Ser Glu
1               5                   10                  15

Ala Asn Ile Leu Lys Leu Ile Lys Pro Leu Leu Leu Asp Glu Leu Trp
                20                  25                  30

Val Val Phe Xaa Lys Val Lys Asn
                35                  40

<210> SEQ ID NO 18
<211> LENGTH: 25
<212> TYPE: PRT
<213> ORGANISM: unknown
<220> FEATURE:
<223> OTHER INFORMATION: first 25 residues of the 7.5 kD peptide

<400> SEQUENCE: 18

Met Lys Ser Arg Gly Lys Asp Leu Asp Lys Ala Tyr Asp Gln Ala Leu
1               5                   10                  15

Asp Tyr Phe Ser Gly Ile Ala Glu Arg
                20                  25
```

<210> SEQ ID NO 19
<211> LENGTH: 8
<212> TYPE: PRT
<213> ORGANISM: unknown
<220> FEATURE:
<223> OTHER INFORMATION: 25 kD fragment primer

<400> SEQUENCE: 19

Asp Glu Phe Gly Asn Tyr Phe Ala
1               5

<210> SEQ ID NO 20
<211> LENGTH: 20
<212> TYPE: DNA
<213> ORGANISM: unknown
<220> FEATURE:
<223> OTHER INFORMATION: forward primer
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: Y = T or C
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: Y = T or C
<220> FEATURE:
<221> NAME/KEY: misc_feature
<222> LOCATION: (15)..(15)
<223> OTHER INFORMATION: Y = T or C
<220> FEATURE:
<221> NAME/KEY: misc_feature
<222> LOCATION: (18)..(18)
<223> OTHER INFORMATION: Y = T or C

<400> SEQUENCE: 20
garttyggna aytayttygc                                              20

<210> SEQ ID NO 21
<211> LENGTH: 20
<212> TYPE: DNA
<213> ORGANISM: unknown
<220> FEATURE:
<223> OTHER INFORMATION: reverse primer
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: R = A or G
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: R = A or G
<220> FEATURE:
<221> NAME/KEY: misc_feature
<222> LOCATION: (15)..(15)
<223> OTHER INFORMATION: Y = T or C
<220> FEATURE:
<221> NAME/KEY: misc_feature

```
<222> LOCATION: (18)..(18)
<223> OTHER INFORMATION: R = A or G

<400> SEQUENCE: 21
aartarttnc craaytcrtc                                                    20

<210> SEQ ID NO 22
<211> LENGTH: 6
<212> TYPE: PRT
<213> ORGANISM: unknown
<220> FEATURE:
<223> OTHER INFORMATION: 14 kD fragment primer

<400> SEQUENCE: 22

Met Asp Ala Lys Lys Arg
1               5

<210> SEQ ID NO 23
<211> LENGTH: 17
<212> TYPE: DNA
<213> ORGANISM: unknown
<220> FEATURE:
<223> OTHER INFORMATION: forward primer
<220> FEATURE:
<221> NAME/KEY: misc_feature
<222> LOCATION: (6)..(6)
<223> OTHER INFORMATION: Y = T or C
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: R = A or G
<220> FEATURE:
<221> NAME/KEY: misc_feature
<222> LOCATION: (15)..(15)
<223> OTHER INFORMATION: R = A or G

<400> SEQUENCE: 23
atggaygcna araarcg                                                       17

<210> SEQ ID NO 24
<211> LENGTH: 17
<212> TYPE: DNA
<213> ORGANISM: unknown
<220> FEATURE:
<223> OTHER INFORMATION: reverse primer
<220> FEATURE:
<221> NAME/KEY: misc_feature
<222> LOCATION: (6)..(6)
<223> OTHER INFORMATION: Y = T or C
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: R = A or G
<220> FEATURE:
<221> NAME/KEY: misc_feature
<222> LOCATION: (15)..(15)
<223> OTHER INFORMATION: R = A or G

<400> SEQUENCE: 24
atggaygcna araarag                                                       17

<210> SEQ ID NO 25
<211> LENGTH: 20
```

```
<212> TYPE: DNA
<213> ORGANISM: unknown
<220> FEATURE:
<223> OTHER INFORMATION: reverse primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: Y = T or C
<220> FEATURE:
<221> NAME/KEY: misc_feature
<222> LOCATION: (9)..(9)
<223> OTHER INFORMATION: Y = T or C
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: R = A or G

<400> SEQUENCE: 25
cgncgyttyt tngcrtccat                                              20

<210> SEQ ID NO 26
<211> LENGTH: 7
<212> TYPE: PRT
<213> ORGANISM: unknown
<220> FEATURE:
<223> OTHER INFORMATION: 7.5 kD fragment primer

<400> SEQUENCE: 26

Asp Lys Ala Tyr Asp Gln Ala
1               5

<210> SEQ ID NO 27
<211> LENGTH: 20
<212> TYPE: DNA
<213> ORGANISM: unknown
<220> FEATURE:
<223> OTHER INFORMATION: forward primer
<220> FEATURE:
<221> NAME/KEY: misc_feature
<222> LOCATION: (3)..(3)
<223> OTHER INFORMATION: Y = T or C
<220> FEATURE:
<221> NAME/KEY: misc_feature
<222> LOCATION: (6)..(6)
<223> OTHER INFORMATION: R = A or G
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: Y = T or C
<220> FEATURE:
<221> NAME/KEY: misc_feature
<222> LOCATION: (14)..(14)
<223> OTHER INFORMATION: Y = T or C
<220> FEATURE:
<221> NAME/KEY: misc_feature
<222> LOCATION: (17)..(17)
<223> OTHER INFORMATION: R = A or G

<400> SEQUENCE: 27
gayaargcnt aygaycargc                                              20
```

<210> SEQ ID NO 28
<211> LENGTH: 20
<212> TYPE: DNA
<213> ORGANISM: unknown
<220> FEATURE:
<223> OTHER INFORMATION: reverse primer
<220> FEATURE:
<221> NAME/KEY: misc_feature
<222> LOCATION: (3)..(3)
<223> OTHER INFORMATION: Y = T or C
<220> FEATURE:
<221> NAME/KEY: misc_feature
<222> LOCATION: (6)..(6)
<223> OTHER INFORMATION: R = A or G
<220> FEATURE:
<221> NAME/KEY: misc_feature
<222> LOCATION: (9)..(9)
<223> OTHER INFORMATION: R = A or G
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: Y = T or C
<220> FEATURE:
<221> NAME/KEY: misc_feature
<222> LOCATION: (18)..(18)
<223> OTHER INFORMATION: R = A or G

<400> SEQUENCE: 28
gcytgrtcrt angcyttrtc                                                    20

<210> SEQ ID NO 29
<211> LENGTH: 26
<212> TYPE: DNA
<213> ORGANISM: unknown
<220> FEATURE:
<223> OTHER INFORMATION: primer IP 1

<400> SEQUENCE: 29
gttggatccc gcacagattg ctcagg                                             26

<210> SEQ ID NO 30
<211> LENGTH: 30
<212> TYPE: DNA
<213> ORGANISM: unknown
<220> FEATURE:
<223> OTHER INFORMATION: primer IP 2

<400> SEQUENCE: 30
gttggatcct acgttaatct gaataagatg                                         30

<210> SEQ ID NO 31
<211> LENGTH: 28
<212> TYPE: DNA
<213> ORGANISM: unknown
<220> FEATURE:
<223> OTHER INFORMATION: primer IP 3

<400> SEQUENCE: 31
gttggatcct gttaatctga aacgctgg                                           28

<210> SEQ ID NO 32
<211> LENGTH: 29
<212> TYPE: DNA
<213> ORGANISM: unknown
<220> FEATURE:
<223> OTHER INFORMATION: primer IP 4

-continued

```
<400> SEQUENCE: 32
gttggatcct tataccaaaa tgtgaggtc                                29

<210> SEQ ID NO 33
<211> LENGTH: 20
<212> TYPE: DNA
<213> ORGANISM: unknown
<220> FEATURE:
<223> OTHER INFORMATION: primer IP 5

<400> SEQUENCE: 33
ttcagaaata cgagcgatgc                                          20

<210> SEQ ID NO 34
<211> LENGTH: 20
<212> TYPE: DNA
<213> ORGANISM: unknown
<220> FEATURE:
<223> OTHER INFORMATION: primer IP 6

<400> SEQUENCE: 34
gtcaagccat aaacaccatc                                          20

<210> SEQ ID NO 35
<211> LENGTH: 20
<212> TYPE: DNA
<213> ORGANISM: unknown
<220> FEATURE:
<223> OTHER INFORMATION: primer IP 7

<400> SEQUENCE: 35
gagggtcaga aaggaagctg                                          20

<210> SEQ ID NO 36
<211> LENGTH: 20
<212> TYPE: DNA
<213> ORGANISM: unknown
<220> FEATURE:
<223> OTHER INFORMATION: primer IP 8

<400> SEQUENCE: 36
gtccaactaa ccctttatgg                                          20

<210> SEQ ID NO 37
<211> LENGTH: 20
<212> TYPE: DNA
<213> ORGANISM: unknown
<220> FEATURE:
<223> OTHER INFORMATION: primer IP 9

<400> SEQUENCE: 37
ttcctagtgc tgaacctttg                                          20

<210> SEQ ID NO 38
<211> LENGTH: 20
<212> TYPE: DNA
<213> ORGANISM: unknown
<220> FEATURE:
<223> OTHER INFORMATION: primer IP 10

<400> SEQUENCE: 38
gttgcgttac ttgaaatgac                                          20

<210> SEQ ID NO 39
<211> LENGTH: 20
```

```
<212> TYPE: DNA
<213> ORGANISM: unknown
<220> FEATURE:
<223> OTHER INFORMATION: primer IP 11

<400> SEQUENCE: 39
ccaaaatgga acttgtttcg                                              20

<210> SEQ ID NO 40
<211> LENGTH: 20
<212> TYPE: DNA
<213> ORGANISM: unknown
<220> FEATURE:
<223> OTHER INFORMATION: primer IP 12

<400> SEQUENCE: 40
gtgagtgcgc cctgaattag                                              20

<210> SEQ ID NO 41
<211> LENGTH: 21
<212> TYPE: DNA
<213> ORGANISM: unknown
<220> FEATURE:
<223> OTHER INFORMATION: primer S1

<400> SEQUENCE: 41
gcttcatttc atcctctgtg c                                            21

<210> SEQ ID NO 42
<211> LENGTH: 21
<212> TYPE: DNA
<213> ORGANISM: unknown
<220> FEATURE:
<223> OTHER INFORMATION: primer S2

<400> SEQUENCE: 42
taaccgccaa aattaatcgt g                                            21

<210> SEQ ID NO 43
<211> LENGTH: 20
<212> TYPE: DNA
<213> ORGANISM: unknown
<220> FEATURE:
<223> OTHER INFORMATION: primer S3

<400> SEQUENCE: 43
ccactattca ttacaacacc                                              20

<210> SEQ ID NO 44
<211> LENGTH: 43
<212> TYPE: DNA
<213> ORGANISM: unknown
<220> FEATURE:
<223> OTHER INFORMATION: 20 nucleotides that matched the M.
      methyltrophus DNA sequence

<400> SEQUENCE: 44
gttctgcagt taaggataac atatggcttt aagctggaac gag                    43

<210> SEQ ID NO 45
<211> LENGTH: 37
<212> TYPE: DNA
<213> ORGANISM: unknown
<220> FEATURE:
<223> OTHER INFORMATION: 22 nucleotides that matched the M.
      methylotrophus DNA sequence
```

```
<400> SEQUENCE: 45
gttggatccg tcgacattaa ttaattttttg cccttag                              37

<210> SEQ ID NO 46
<211> LENGTH: 48
<212> TYPE: DNA
<213> ORGANISM: unknown
<220> FEATURE:
<223> OTHER INFORMATION: oligonucleotide 1

<400> SEQUENCE: 46
gtttgaagac tccgacgcga tggccagcga tcggcgcctc agcttttg                  48

<210> SEQ ID NO 47
<211> LENGTH: 48
<212> TYPE: DNA
<213> ORGANISM: unknown
<220> FEATURE:
<223> OTHER INFORMATION: oligonucleotide 2

<400> SEQUENCE: 47
caaaagctga ggcgccgatc gctggccatc gcgtcggagt cttcaaac                  48

<210> SEQ ID NO 48
<211> LENGTH: 48
<212> TYPE: DNA
<213> ORGANISM: unknown
<220> FEATURE:
<223> OTHER INFORMATION: oligonucleotide 3
<220> FEATURE:
<221> NAME/KEY: misc_feature
<222> LOCATION: (15)..(15)
<223> OTHER INFORMATION: A = 6-methyladenine

<400> SEQUENCE: 48
gtttgaagac tccgacgcga tggccagcga tcggcgcctc agcttttg                  48

<210> SEQ ID NO 49
<211> LENGTH: 48
<212> TYPE: DNA
<213> ORGANISM: unknown
<220> FEATURE:
<223> OTHER INFORMATION: oligonucleotide 4
<220> FEATURE:
<221> NAME/KEY: misc_feature
<222> LOCATION: (38)..(38)
<223> OTHER INFORMATION: A = 6-methyladenine

<400> SEQUENCE: 49
caaaagctga ggcgccgatc gctggccatc gcgtcggagt cttcaaac                  48

<210> SEQ ID NO 50
<211> LENGTH: 8
<212> TYPE: PRT
<213> ORGANISM: unknown
<220> FEATURE:
<223> OTHER INFORMATION: single internal CnBr digestion fragment

<400> SEQUENCE: 50

Gly Arg Gly Arg Gly Val Gly Val
1               5
```